US009102724B2

(12) United States Patent
Cummings et al.

(10) Patent No.: US 9,102,724 B2
(45) Date of Patent: Aug. 11, 2015

(54) ANTI-FZD10 MONOCLONAL ANTIBODIES AND METHODS FOR THEIR USE

(75) Inventors: W. Jason Cummings, Bellevue, WA (US); Munehisa Yabuki, Seattle, WA (US); John B. Leppard, Mukilteo, WA (US); Christi L. Wood, Snohomish, WA (US); Nancy Maizels, Seattle, WA (US); Daniel S. Allison, Lake Forest Park, WA (US); Larry W. Tjoelker, Kirkland, WA (US)

(73) Assignee: Omeros Corporation, Seattle, WA (US)

( * ) Notice: Subject to any disclaimer, the term of this patent is extended or adjusted under 35 U.S.C. 154(b) by 0 days.

(21) Appl. No.: 13/571,151

(22) Filed: Aug. 9, 2012

(65) Prior Publication Data

US 2013/0095104 A1    Apr. 18, 2013

Related U.S. Application Data

(60) Provisional application No. 61/523,102, filed on Aug. 12, 2011, provisional application No. 61/548,110, filed on Oct. 17, 2011.

(51) Int. Cl.
    *C07K 16/28* (2006.01)
    *C07K 16/30* (2006.01)
    *A61K 45/06* (2006.01)
    *A61K 47/48* (2006.01)

(52) U.S. Cl.
    CPC ............... *C07K 16/28* (2013.01); *A61K 45/06* (2013.01); *A61K 47/48469* (2013.01); *A61K 47/48561* (2013.01); *C07K 16/2863* (2013.01); *C07K 16/2896* (2013.01); *C07K 2317/23* (2013.01); *C07K 2317/24* (2013.01); *C07K 2317/732* (2013.01); *C07K 2317/76* (2013.01); *C07K 2317/92* (2013.01)

(58) Field of Classification Search
    CPC ............... A61K 47/48561; A61K 47/48569; A61K 47/48623; C07K 16/28; C07K 16/2896; C07K 2317/23; C07K 2317/24; C07K 2317/732; C07K 2317/76; C07K 2317/92
    See application file for complete search history.

(56) References Cited

U.S. PATENT DOCUMENTS

| | | | |
|---|---|---|---|
| 4,946,778 | A | 8/1990 | Ladner et al. |
| 5,091,513 | A | 2/1992 | Huston et al. |
| 5,132,405 | A | 7/1992 | Huston et al. |
| 5,208,020 | A | 5/1993 | Chari et al. |
| 6,528,624 | B1 | 3/2003 | Idusogie et al. |
| 6,538,124 | B1 | 3/2003 | Idusogie et al. |
| 6,765,087 | B1 | 7/2004 | Casterman et al. |
| 6,838,254 | B1 | 1/2005 | Hamers et al. |
| 7,297,775 | B2 | 11/2007 | Idusogie et al. |
| 7,317,091 | B2 | 1/2008 | Lazar et al. |
| 7,364,731 | B2 | 4/2008 | Idusogie et al. |
| 7,657,380 | B2 | 2/2010 | Lazar et al. |
| 7,662,925 | B2 | 2/2010 | Lazar et al. |
| 7,740,847 | B2 | 6/2010 | Allan et al. |
| 2008/0131435 | A1 | 6/2008 | Stavenhagen et al. |
| 2008/0138344 | A1 | 6/2008 | Stavenhagen et al. |
| 2009/0092599 | A1 | 4/2009 | Lazar et al. |
| 2009/0226421 | A1 | 9/2009 | Parren et al. |
| 2010/0093033 | A1 | 4/2010 | Maizels et al. |
| 2010/0104574 | A1 | 4/2010 | Gurney et al. |

FOREIGN PATENT DOCUMENTS

| | | |
|---|---|---|
| WO | WO 94/13804 | 6/1994 |
| WO | WO 2004/063351 A2 | 7/2004 |
| WO | WO 2005/004912 A1 | 1/2005 |
| WO | WO 2006/079372 A1 | 8/2006 |
| WO | WO 2006/088494 A2 | 8/2006 |
| WO | WO 2006/105338 A2 | 10/2006 |
| WO | WO 2007/024249 A2 | 3/2007 |
| WO | Wo 2007/148417 A1 | 12/2007 |
| WO | WO 2008/061020 A2 | 5/2008 |
| WO | WO 2009/029315 A2 | 3/2009 |

OTHER PUBLICATIONS

Paul, Fundamental Immunology, 3rd Edition, 1993, pp. 292-295.*
Rudikoff et al., Proc. Nat'l Acad. Sci. USA 1982; 79:1979-83.*
Brown et al., J. Immunol. May 1996; 156(9):3285-91.*
MacCallum et al., (J Mol Biol. 1996; 262:732-745.*
Maizels, N., "Immunoglobulin gene diversification,"*Annu. Rev. Genet.* 39:23-46 (2005).
Cummings, W. Jason, et al., "Chromatic structure regulates gene conversion," *PLoS Biology* 5(10):e246 (2007).
Yabuki, M., et al., "The MRE11-RAD50-NBS1 complex accelerates somatic hypermutation and gene conversion of immunoglobulin variable regions," *Nature Immunology* 6(7):730-736 (2005).
Barbas, S., et al., "Human autoantibody recognition of DNA," *Proc. Natl. Acad. Sci. USA* 92:2529-2533 (1995).
McLane, K., et al., "Transplantation of a 17-amino acid α-helical DNA-binding domain into an antibody molecule confers sequence-dependent DNA recognition," *Proc. Natl. Acad. Sci. USA* 92:5214-5218 (1995).
Klimka, A., et al., "Human anti-CD30 recombinant antibodies by guided phage antibody selection using cell panning," *Br. J. Cancer* 83(2):252-260 (2000).
Rader, C., et al., "A phage display approach for rapid antibody humanization: Designed combinatorial V gene libraries," *Proc. Natl. Acad. Sci. USA* 95:8910-8915 (1998).
Cumbers, S. J., et al., "Generatin and interative affinity maturation of antibodies in vitro using hypermutating B-cell lines," *Nature Biotechnology* 20:1129-1134 (2002).

(Continued)

*Primary Examiner* — Sheela J Huff
*Assistant Examiner* — Jessica H Roark
(74) *Attorney, Agent, or Firm* — Tinika J. Quinton; Marcia S. Kelbon

(57) ABSTRACT

The present invention relates generally to anti-FZD10 antibodies and to methods of using anti-FZD10 antibodies. In particular, the anti-FZD10 antibodies described herein are useful for altering one or more of survival, replication, differentiation and epithelial-to-mesenchymal cell transition of embryonic stem cells and/or for the treatment of diseases, such as a variety of cancers, associated with expression of FZD10, including as stand-alone therapies and in combination therapies with other agents.

19 Claims, 10 Drawing Sheets

(56) References Cited

OTHER PUBLICATIONS

Buerstedde, J.-M., et al., "Light chain gene conversion continues at high rate in an ALV-induced cell line," *The EMBO Journal* 9(3):921-927 (1990).
Yabuki, M., et al., "E2A acts in cis in $G_1$ phase of cell cycle to promote Ig gene diversification,"*J Immunol* 182:408-415 (2009).
Marks, J.D., et al., "By-passing immunization: Building high affinity human antibodies cy chain shuffling," *Biotechnology* 10:779-783 (1992).
Beibor, S.H.W., et al., "Guided selection of a pan carcinoma specific antibody reveals similar binding characteristics yet structural divergence between the original murine antibody and its human equivalent,"*J. Mol. Biol.* 296:833-849 (2000).
Tsurushita, N., et al., "Humanization of a chicken anti-IL-12 monoclonal antibody," *J Immunological Methods* 295:9-19 (2004).
Seo, H., et al., "Rapid generation of specific antibodies by enhanced homologous recomibation," *Nature Biotechnology* 23(6):731-735 (2005).
Barbas, S.M., et al., "Recognition of DNA by synthetic antibodies," *J. Am. Chem. Soc.* 116:2161-2162 (1994).
Cummings, W.J., et al., "Genetic variation stimulated by epigenetic modification," *PLos ONE* 3(12):e4075 (2007).
Culp, P.A., et al., "Antibodies to TWEAK receptor inhibit human tumor growth through dual mechanisms," *Clin Cancer Res* 16:497-508 (2010).
Nagayama, S. et al., "Therapeutic potential of antibodies against FZD10, a cell-surface protein, for synovial sarcomas," *Oncogene* 24:6201-6212 (2005).
Fukukawa, C., et al., "Radioimmunotherapy of human synovial sarcoma using a monoclonal antibody against FZD10," *Cancer Sci* 99(2):432-440 (2008).
Barbas III, C.F., et al., "In vitro evolution of a neutralizing human antibody to human immunodeficiency virus type 1 to enhance affinity and broaden strain corss-reactivity," *Proc, Natl. Acad. Sci. USA* 91:3809-3813 (1994).
Carter, P., et al., "Humanization of an anti-p185$^{HER2}$ antibody for human cancer therapy," *Proc. Natl, Acad. Sci.* 89:4285-4289 (1992).
Co, M.S., et al., "Humanized antibodies for antiviral therapy," *Proc. Natl. Acad. Sci. USA* 88:2869-2873 (1991).
Filmus, J., et al., "Glypicans," *Genome Biology* 9:224 (2008).
Gorman, S.D., et al., "Reshaping a therapeutic CD4 antibody," *Proc. Natl. Acac. Sci. USA* 88: 4181-4185 (1991).
Gram, H., et al.., "In vitro selection and affinity maturation of antibodies from a naïve combinatorial immunoglobulin library," *Proc. Natl. Acad. Sci. USA* 89:3576-3580 (1992).
Holliger, P., et al., ""Diabodies": Small bivalent and bispecific antibody fragments," *Proc. Natl. Acad. Sci. USA* 90:6444-6448 (1993).
Ill, C.R., et al., "Design and construction of a hybrid immunoglobulin domain with properties of both heavy and light chain variable regions," *Protein Engineering* 10(8):949-957 (1997).
Inbar, D., et al., "Localization of antibody-combining sites within the variable portions of heavy and light chains," *Proc. Natl. Acad. Sci. USA* 69(9):2659-2662 (1972).
Katoh, M., "Networking of WNT, FGF, Notch, BMP, and Hedgehog signaling pathways during carcinogenesis," *Stem Cell Rev* 3:30-38 (2007).
LoBuglio, A.F., et al., "Mouse/human chimeric monoclonal antibody in man: kinetics and immune response," *Proc. Natl/Acad. Sci. USA* 86:4220-4224 (1989).
Martin, F., et al., "The affinity-selection of a minibody polypeptide inhibitor of human interleukin-6," *The EMBO Journal* 13(22):5303-5309 (1994).
Petrocca, F., et al., "Promise and challenge of RNA interference-based therapy for cancer," *J Clinical Oncology* 29(6):747-754 (2010).
Queen, C., et al., "A humanized antibody that binds to the interleukin 2 receptor," *Proc. Natl. Acad. Sci. USA* 86:10029-10033 (1989).
Ridgway, J.B.B., et al., "Knobs-into-holes engineering of antibody $C_H3$ domains for heavy chain heterodimerization," *Protein Engineering* 9(7):617-621 (1996).

Robinett, C.C., et al., "In vivo localization of DNA sequences and visualization of large-scale chromatic organization using lac operator/repressor recognition," *The Journal of Cell Biology*135(6):1685-1700 (1996).
Sato, K., et al., "Reshaping a human antibody to inhibit the interleukin 6-dependent tumor cell growth," *Cancer Research* 53:851-856 (1993).
Traunecker, A., et al., "Bispecific single chain molecules (Janusins) target cytotoxic lymphocytes on HIV infected cells," *The EMBO Journal* 10(12):3655-3659 (1991).
Wei, J., et al., "Canonical Wnt signaling induces skin fibrosis and subcutaneous lipoatrophy: a novel mouse model for scleroderma?" *Arthritis Rheum* 63(6):1707-1717 (2011).
Almagro, J.C., et al., "Humanization of antibodies," *Fronteirs in Bioscience* 13:1619-1633 (2008).
Foote, J., et al., "Antibody framework residues affecting the conformation of the hypervariable loops," *J Mol Biol* 224:487-499 (1992).
Shi, Q., et al., "siRNA therapy for cancer and non-lethal diseases such as arthritis and osteoporosis," *Expert Opin. Biol. Ther*, 11(1):5-16 (2011).
Wang, X., et al., "Small interfering RNA for effective cancer therapies," *Mini-Reviews in Medicinal Chemistry* 11:114-124 (2011).
Schier, R., et al., "Isolation of picomolar affinity anti-c-erbB-2 single-chain Fv by molecular evolution of the complementarity determining regions in the center of the antibody binding site," *J. Mo. Biol.* 263:551-567 (1996).
Portolano, S., et al., "Lack of promiscuity in autoantigen-specific h and L chain combinations as revealed by human H and L chain "roulette"," *The Journal of Immunology* 150(3):880-887 (1993).
Clackson, T., et al., "Making antibody fragments using phage display libraries," *Nature* 352:624-628 (1991).
Riechmann, L., et al., "Reshaping human antibodies for therapy," *Nature* 332:323-327 (1988).
Verhoeyen, M., et al., "Reshaping human antibodies: Grafting an antilysozyme activity," *Science* 239:1534-1536 (1988).
Kettleborough, C.A., et al., "Humanization of a mouse monoclonal antibody by CDR-grafting: the importance of framework residues on loop conformation," *Protein Engineering* 4(7):773-873 (1991).
Maeda., H., et al., "Construction of reshaped human antibodies with HIV-neutralizing activity," *Hum Antibod Hybridomas* 2:124-134 (1991).
Co, M.S., et al., "Chimeric and humanized antibodies with specificity for the CD33 antigen," *The Journal of Immunology* 148(4):1149-1154 (1992).
Stemmer, W.P.C., "Rapid evolution of a protein in vitro by DNA shuffling," *Nature* 370:389-391 (1994).
Ward, E.S., et al., "Binding activities of a repertoire of single immunoglobulin variable domains secreted from *Escherichia coli*," *Nature* 341:544-546 (1989).
Hochman, J., et al., "Folding and interaction of subunits at the antibody combining sites," *Biochemistry* 15(12):2706-2710 (1976).
Ehrlich, P.H., et al., "Isolatin of an active heavy-chain variable domain from homogenous rabbit antibody by cathepsin B digestion of the aminoethylated heavy chain," *Biochemistry* 19:4091-4096 (1980).
Holliger, P., et al., "Engineering bispecific antibodies," *Current Opinion in Biotechnology* 4:446-449 (1993).
Tempest, P.R., et al., "Reshaping a human monoclonal antibody to inhibit human respiratory syncytial virus infection in vivo," *Biotechnology* 9:266-271 (1991).
Nijening, J.E., et al., "Using large-scale RNAi screens to identify novel drug targets for cancer," *IDrugs* 13(11):772-777 (2010).
Traunecker, A., et al., "Janusin: New molecular design for bispecific reagents," *Int. J. Cancer* 7:51-52 (1992).
Venter, J.C., et al., "The sequence of the human genome," *Science* 291:1304-1352 (2001).
Wang, Y., et al., "Protein chemistry and structure: A large family of putative transmembrane receptors homologous to the product of the *Drosophila* tissue polarity gene frizzled," *J Biol Chem* 271:4468-4476 (1996).
Vinson, C.R., et l., "A *Drosophila* tissue polarity locus enclodes a protein containing seven potential transmembrane domains," *Nature* 338:263-264 (1989).

(56) References Cited

OTHER PUBLICATIONS

Hlubek, F., et al., "Wnt/FZD signaling and colorectal cancer morphogenesis," *Front Biosci* 12:458-470 (2007).
Bhanot, P., et al., "A new member of the frizzled family from *Drosophila* functions as a wingless receptor," *Nature* 382:225-230 (1996).
Carron, C., et al., "Frizzled receptor dimerization is sufficient to activate the Wnt/β-catenin pathway," *Journal of Cell Science* 116:2541-2550 (2003).
Koike, J., et al., "Molecular cloning of Frizzled-10, a novel member of the Frizzled gene family," *Biochem Biophys Res Comm* 262:39-43 (1999).
Roa, T.P., et al., "An updated overview on Wnt signaling pathways: A prelude for more," *Circulation Research* 106:1798-1806 (2010).
Nagayama, S., et al., "Genome-wide analysis of gene expression in synovial sarcomas using a cDNA microarray," *Cancer Research* 62:5859-5866 (2002).
Kirikoshi, H., et al., "Expression profiles of 10 members of Frizzled gene family in human gastric cancer," *Int J Oncol* 19(4):767-71 (2001).
Nagayama, S., et al., "Inverse correlation of the up-regulation of FZD10 expression and the activation of β-catenin in synchronous colorectal tumors," *Cancer Sci* 100(3):405-412 (2009).
Schulte, G., "International union of basic and clinical pharmacology. LXXX. The class frizzled receptors," *Pharmacological Reviews* 62:632-667 (2010).
Kyrgidis, A., et al., "Melanoma: Stein cells, sun exposure and hallmarks for carcinogenesis, molecular concepts and future clinical implications," *J Carcinogenesis* 9:3-17 (2010).
Davies, D.R., et al., "Antibody-antigen complexes" *Annu Rev Biochem* 59:439-73 (1990).
Radaev, S., et al., "Protein structure and folding : The structure of a human type III fcγ receptor in complex with Fc," *Biol Chem* 276:16469-16477 (2001).
Cartron, G., et al., "Therapeutic activity of humanized anti-CD20 monoclonal antibody and polymorphism ub IgG Fc receptor Fc γRIIIa gene," *Blood* 99:754-758 (2002).
Lehrnbecher, T., et al., "Variant genotypes of the low-affinity Fcγ receptors in two control populations and review of low-affinity Fc γ receptor polymorphisms in control and disease populations," *Blood* 94:4220-4232 (1999).
Raghavan, M., et al., "Fc receptors and their interactions with immunoglobulins," *Annu Rev Cell Dev Biol* 12:181-220 (1996).
Pode-Shakked, N., et al,, "Resistance or sensitivity of Wilms' tumor to anti-FZD7 antibody highlights the Wnt pathway as a possible therapeutic target," *Oncogene* 30:1664-1680 (2011).
Gradle, D., et al., "The Wnt/Wg signal transducer β-catenin controls fibronectin expression," *Mol Cell Biol* 19(8):5576-5587 (1999).
Luria, S.E., et al., "Mutations of bacteria from virus sensitivity to virus resistance," *Genetics* 28:491-511 (1943).
Geetha-Loganathan, P., et al., "Expression of Wnt signaling pathway genes during chicken craniofacial development," *Developmental Dynamics* 238:1150-1165 (2009).
Flavell, D.J., et al., "Anti-CD7 antibody and immunotoxin treatment of human CD7+ T'cell leukaemia is significantly less effective in NOD/LtSz-scid mice than in CB.17 scid mice," *Br J Cancer* 83(12):1755-1761 (2000).
Daniels, T.R., et al., "Conjugation of an anti-transferrin receptor IgG3-avidin fusion protein with biotinylated saporin results in significant enhancement of its cells cytotoxicity against malignant hematopoietic cells," *Molecular Cancer Therapeutics* 6:2995-3008 (2007).
Lazar, G.A., et al., "Engineered antibody Fc variants with enhanced effector function," *PNAS* 103(11):4005-4010 (2006).
Stavenhagen, J.B., et al., "Fc optimization of therapeutic antibodies enhances their ability to kill tumor cells In vitro and controls tumor expansion In vivo via low-affinity activating Fcγ receptors," *cancer Research* 67:8882-8890 (2007).
Park, C.Y., et al., "Cancer stem cell-directed therapies: Recent data from the laboratory and clinic," *Molecular Therapy* 17(2):219-230 (2009).
Curtin, J.C., et al., "Drug discovery approaches to target Wnt signaling in cancer stem cells," *Oncotarget* 1:563-566 (2010).
DeAlmeida, V.I., et al., "The soluble Wnt receptor firzzled8CDR-hFc inhibits the growth of teratocarcinomas in vivo," *Cancer Res* 67:5371-5379 (2007).
Ettenberg, S.A., et al., "Inhibition of tumorigenesis is driven by different Wnt proteins requires blockade of distinct ligand-binding regions by LRP6 antibodies," *PNAS* 107(35):15473-15478 (2010).
Fukukawa, C., et al., "Activation of the non-canonical Dvl-Rac1-JNK pathway by frizzled homologue 10 in human synovial sarcoma," *Oncogene* 28:1110-1120 (2009).
He, B., et al., "A monoclonal antibody against Wnt-1 induces apoptosis in human cancer cells," *Neoplasia* 6(1):7-14 (2004).
Hu, J., et al., "Blockade of Wnt signaling inhibits angiogenesis and tumor growth in hepatocellular carcinoma," *Cancer Res* 69:6951-6959 (2009).
Ravetch, J., et al., "IgG Fc receptors," *Annu Rev Immunol* 19:275-90 (2001).
Jefferis, R., et al., "Interaction sites on human IgG-Fc for FcγR: current models," *Immunology Letters* 82:57-65 (2002).
Ghetie, V., et al., "Multiple roles for the major histocompatibility complex classI-related receptor FcRn,"*Annu Rev Immunol* 18:739-766 (2000).
You, L., et al., "An anti-Wnt-2 monoclonal antibody induces apoptosis in malignant melanoma cells and inhibits tumor growth," *Cancer Res* 64:5385-5389 (2004).
Snow, G.E., et al., "Wnt pathway reprogramming during human embryonal carcinoma differentiation and potential for therapeutic targeting," *BMC Cancer* 9:383-395 (2009).
Guggar, M., et al., "GPR87 is an overexpressed G-protein coupled receptor in squamous cell carcinoma of the lung," *Disease Markers* 24:41-50 (2008).
Uematsu, K., et al., "Wnt pathway activation in mesothelioma: Evidence of disheveled overexpression and transcriptional activity of β-catenin," *Cancer Res* 63:4547-4551 (2003).
Kemp, C.R., et al., "Expression of Frizzled5, Frizzled7, and Frizzled10 during early mouse development and interactions with canonical Wnt signaling," *Developmental Dynamics* 236:2011-2019 (2007).
Hayashi, K., et al., "WNT's in the neonatal mouse uterus: Potential regulation of endometrial gland development," *Biology of Reproduction* 84:308-319 (2011).
Kawakami, Y., et al., "Involvement of frizzled-10 in Wnt-7a signaling during chick limb development," *Develop Growth Differ* 42:561-569 (2000).
Garcia-Morales, C., et al., "Frizzled-10 promotes sensory neuron development in *Xenopus* embryos," *Developmental Biology* 335:143-155 (2009).
Nasevicius, A., et al., "Sequence, expression, and location of Zebrafish frizzled 10," *Mechanaisms of Devlopment* 92:311-314 (2000).
Li, Z., et al., "Functional and transcriptional characterization of human embryonic stem cell-derived endothelial cells for treatment of myocardial infarction," *PLoS ONE* 4(12):e8443 (2009).
Xie, C,-X., et al., "Smooth muscle cell differentiation in vitro: Models and underlying molecular mechanisms," *Arterioscler Thromb Vase Biol* 31(7):1485-1494 (2011).
Ramkisoensing, A.A., et al., "Human embryonic and fetal mesenchymal stem cells differentiate toward three different cardiac lineages in contrast to their adult counterparts," *PLoS ONE* 6(9):e24164 (2011).
Cao, F., et al., "Transcriptional and functional profiling of human embryonic stem cell-derived cardiomyocytes," *PLoS ONE* 3(10):e3474 (2008).
Sondermann, P., et al., "Molecular basis for immune complex recognition: A comparison of Fc-receptor structures," *J Mol Biol* 309:737-749 (2001).

(56) References Cited

OTHER PUBLICATIONS

Hu, C.-H., et al., "Human umbilical cord-derived endothelial progenitor cells promote growth cytokines-mediated neorevascularization in rat myocardial infarction," *Chin Med J* 122(5):548-555 (2009).

Hanahan, D., et al., "Hallmarks of cancer: The next generation," *Cell* 144:646-674 (2011).

Hanahan, D., et al., "The hallmarks of cancer," *Cell* 100:57-70 (2000).

Cavallo, F., et al., "2011: the immune hallmarks of cancer," *Cancer Immunol Immunother* 60:319-326 (2011).

Quadros, E.V., et al., "Targeted delivery of saporin toxin by monoclonal antibody to the transcobalamin receptor, TCbIR/CD320," *Molecular Cancer Therapeutics* 9:3033-3040 (2010).

Polito, L., et al., "ATG-saporin-S6 immunotoxin: a new potent and selective drug to eliminate activated lymphocytes and lymphoma cells," *Br J Haematol* 147:710-718 (2009).

DeNardo, G.L., et al., "Comparison of 1,4,7,10-tetraazacyclododecane-N,N',N",N'"-tetraacetic acid (DOTA)—peptide-ChL6, a novel immunoconjugate with catabolizable linker, to 2-iminothiolane-2-[p-(bromoacetamido)benzyl]-DOTA-ChL6 in breast cancer xenografts, *Clinical Cancer Research* 4:2483-2490 (1998).

Chien, A.J., et al., "WNTS and WNT receptors as therapeutic tools and targets in human disease processes," *Front Biosci* 12:448-457 (2007).

Sondermann, P., et al., "The 3.2-Å crystal structure of the human IgG1 Fc fragment-FcγRIII complex," *Nature* 406:267-273 (2000).

Gazzano-Santoro, H., et al., "A non-radioactive complement-dependent cytotoxicity assay for anti-CD20 monoclonal antibody," *J Immunol Methods* 202:163-171 (1997).

Gazit, A., et al., "Human frizzled 1 interacts with transforming Wnts to transduce a TCF dependent transcriptional response," *Oncogene* 18:5959-5966 (1999).

He, T.-C., et al., "Identification of c-*MYC* as a target of the APC pathway," *Science* 281:1509-1512 (1989).

Köhler, G., et al., "Derivation of specific antibody-producing tissue culture and tumor lines by cell fusion," *Eur J Immunol* 6:511-519 (1976).

Kuroda, K., et al., "Saproin toxin-conjugated monoclonal antibody targeting prostate-specific membrane antigen has potent anticancer activity," *The Prostate* 70:1286-1294 (2010).

Yip, W.L., et al., "Targeted delivery and enhanced cytotoxicity of cetuximab-saporin by photochemical internalization in EGFR-positive cancer cells," *Molecular Pharmaceutics* 4(2):241-251 (2007).

Zimmerman, K., et al., "A triglycine linker improves tumor uptake and biodistribution of 67-cu-labeled anti-neuroblastoma MAb chCE7 F(ab')$_2$ fragments," *Nuclear Medicine & Biology* 26:943-950 (1999).

Kawai, A., et al., "Establishment and characterization of a biphasic synovial sarcoma cell line, SYO-1," *Cancer Letters* 204:105-113, (2004).

Nunnally, A.P., et al., "Analysis of *Fz10* expression in mouse embryos," *Dev Genes Evol* 214:144-148 (2004).

Yan, Y., et al., "Expression of Frizzled10 in mouse central nervous system," *Gene Expression Patterns* 9:173-177 (2009).

Peterson, J.J., et al., "Enzymatic cleavage of peptide-linked rafiolabels from immunoconjugates," *Bioconjugate Chemistry* 10(4):553-557, (1999).

Hanaoka, H., et al., "Radioimmunotherapy of solid tumors targeting a cell-surface protein, FZD10: therapeutic efficacy largely depends on radiosensitivity," *Ann Nucl Med* 23:479-485 (2009).

Hu, C.-H., et al., "Expanded human cord blood-derived endothelial progenitor cells salvage infacted myocardium in rats with acute myocardial infarction," *Clin Exp Pharmacol Physiol* 37:551-556 (2010).

Tetsu, O., et al., "β-Catenin regulates expression of cyclin D1 in colon carcinoma cells," *Nature* 398:422-426 (1999).

Terasaki, H., et al., "Frizzled-10, up-regulated in primary colorectal cancer, is a positive regulator of the WNT-β-catenin—TCF signaling pathway," *International Journal of Molecular Medicine* 9(2):107-112 (2002).

\* cited by examiner

Figure 4

Both antibodies have the same highly diversified parental heavy chain...

```
        1
DTLacO  AVTLDESGGGLQTPGGALSLVCKASGFTFSSNAMGWVRQAPGKGLEWVAGIDDDGSGTRYAPAVKG
B9      ............................FN.F....E.....................YPN.GS...

65                                                            125
DTLacO  RATISRDNGQSTLRLQLNNLRAEDTGTYYCTKCAYS-SGCDYEGGYIDAWGHGTEVIVSS
B9      ...............................F.A.SG.GG.WGG.IADD..........
```

SEQ ID NO: 13
SEQ ID NO: 1

...but have distinct light chain CDR1s:

```
           1
DTLacO    ALTQPASVSANLGGTVKITCSG-GGSYAGSYYYGWYQQKSPGSAPVTVIYDNDKRPS
Parent:  A5     ..................... ...............A......L..Y.N....
Progeny: L9.3   .............P.E..... ...-D...........A......L..Y.N....
         L32.2  .............P.E..... ...SDS.........A......L..Y.N....

107
DTLacO   DIPSRFSGSLSGSTNTLTITGVRADDEAVYFCGSADNSGAAFGAGTTLTVL
         A5     ...................................................
         L9.3   ...................................................
         L32.2  ...................................................
```

SEQ ID NO: 17
SEQ ID NO: 2
SEQ ID NO: 3
SEQ ID NO: 4

Figure 7
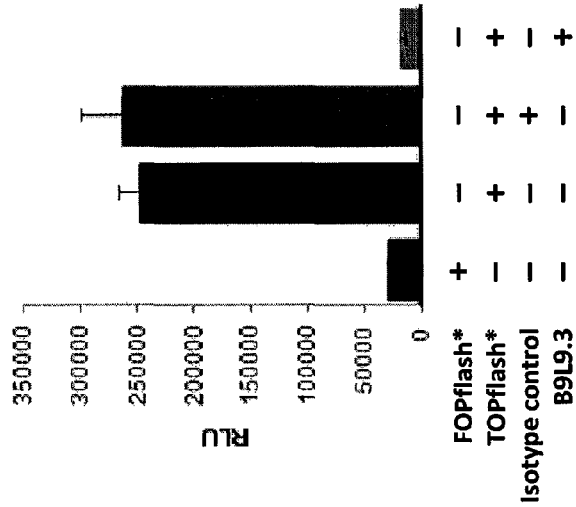
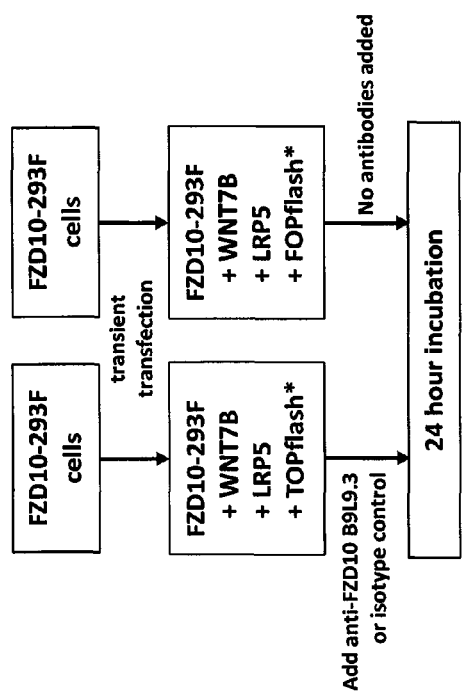

```
               1         2         3         4         5          6
      1234567890123456789012345678901234567890123456789012a345678901234 5
cB9L9.3H  AVTLDESGGGLQTPGGALSLVCKASGFTFSSFNMFWVRQEPGKGLEWVAGIDDDGSYPNYGSAVKG   SEQ ID NO: 1
hB9L9.3H  EVQLVESGGGLVQPGGSLRLSCAASGFTFSSFNMFWVRQAPGKGLEWVAGIDDDGSYPNYGSAVKG   SEQ ID NO: 39
     HIII EVQLVESGGGLVQPGGSLRLSCAASGFTFS-----WVRQAPGKGLEWVS-----------------   SEQ ID NO: 40

7         8         9        100        110
      67890123456789012abc345678901234567890abcdefghi123456789 0123
cB9L9.3H  RATISRDNGQSTLRLQLNNLRAEDTGTYFCAKSGYGGSWGGYIADDIDAWGHGTEVIVSS
hB9L9.3H  RATISRDNSKNTLYLQMNSLRAEDTAVYYCAKSGYGGSWGGYIADDIDAWGQGTLVTVSS
     HIII RFTISRDNSKNTLYLQMNSLRAEDTAVYYCAR----------------WGQGTLVTVSS
```

VL

```
             1         2         3         4         5
      1234567891234567890123456789ab8901234567 89a012345678901234 56
cB9L9.3L  **ALTQPASVSANPGETVKITCSGDGSYAGSYYYGWYQQKAPGSAPVTLIYYNNKRPS          SEQ ID NO: 3
hB9L9.3L  **ELTQPPSVSVSPGQTARITCSGDGSYAGSYYYGWYQQK*PGQAPVTLIYYNNKRPS          SEQ ID NO: 37
     LIII SYELTQPPSVSVSPGQTARITC-----------WYQQK*PGQAPVLVIY-------           SEQ ID NO: 38

6         7         8         9        100
      789012345678901234567890123456789012345 6a
cB9L9.3L  DIPSRFSGSLSGSTNTLTITGVRADDEAVYFCGSADNSGAAFGAGTTLTVL
hB9L9.3L  GIPERFSGSLSGSTNTLTISGVQAEDEADYYCGSADNSGAAFGGGTKLTVL
     LIII GIPERFSGSGSNSGNTATLTISGVQAEDEADYYC-------FGGGTKLTVL
```

ID NO:28.

SEQUENCE LISTING

<160> NUMBER OF SEQ ID NOS: 40

<210> SEQ ID NO 1
<211> LENGTH: 126
<212> TYPE: PRT
<213> ORGANISM: Gallus gallus

<400> SEQUENCE: 1

Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser Ser Phe
            20                  25                  30

Asn Met Phe Trp Val Arg Gln Glu Pro Gly Lys Gly Leu Glu Trp Val
        35                  40                  45

Ala Gly Ile Asp Asp Gly Ser Tyr Pro Asn Tyr Gly Ser Ala Val
    50                  55                  60

Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Gly Thr Tyr Phe Cys
                85                  90                  95

Ala Lys Ser Gly Tyr Gly Gly Ser Trp Gly Gly Tyr Ile Ala Asp Asp
            100                 105                 110

Ile Asp Ala Trp Gly His Gly Thr Glu Val Ile Val Ser Ser
        115                 120                 125

<210> SEQ ID NO 2
<211> LENGTH: 107
<212> TYPE: PRT
<213> ORGANISM: Gallus gallus

<400> SEQUENCE: 2

Ala Leu Thr Gln Pro Ala Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
            20                  25                  30

Gly Trp Tyr Gln Gln Lys Ala Pro Gly Ser Ala Pro Val Thr Leu Ile
        35                  40                  45

Tyr Tyr Asn Asn Lys Arg Pro Ser Asp Ile Pro Ser Arg Phe Ser Gly
    50                  55                  60

Ser Leu Ser Gly Ser Thr Asn Thr Leu Thr Ile Thr Gly Val Arg Ala
65                  70                  75                  80

Asp Asp Glu Ala Val Tyr Phe Cys Gly Ser Ala Asp Asn Ser Gly Ala
                85                  90                  95

Ala Phe Gly Ala Gly Thr Thr Leu Thr Val Leu
            100                 105

<210> SEQ ID NO 3
<211> LENGTH: 107
<212> TYPE: PRT
<213> ORGANISM: Gallus gallus

<400> SEQUENCE: 3

Ala Leu Thr Gln Pro Ala Ser Val Ser Ala Asn Pro Gly Glu Thr Val
1               5                   10                  15

Lys Ile Thr Cys Ser Gly Asp Gly Ser Tyr Ala Gly Ser Tyr Tyr Tyr
                20                  25                  30

Gly Trp Tyr Gln Gln Lys Ala Pro Gly Ser Ala Pro Val Thr Leu Ile
            35                  40                  45

Tyr Tyr Asn Asn Lys Arg Pro Ser Asp Ile Pro Ser Arg Phe Ser Gly
        50                  55                  60

Ser Leu Ser Gly Ser Thr Asn Thr Leu Thr Ile Thr Gly Val Arg Ala
65              70                  75                  80

Asp Asp Glu Ala Val Tyr Phe Cys Gly Ser Ala Asp Asn Ser Gly Ala
                85                  90                  95

Ala Phe Gly Ala Gly Thr Thr Leu Thr Val Leu
            100                 105

<210> SEQ ID NO 4
<211> LENGTH: 108
<212> TYPE: PRT
<213> ORGANISM: Gallus gallus

<400> SEQUENCE: 4

Ala Leu Thr Gln Pro Ala Ser Val Ser Ala Asn Pro Gly Glu Thr Val
1               5                   10                  15

Lys Ile Thr Cys Ser Gly Ser Asp Ser Ser Tyr Ala Gly Ser Tyr Tyr
                20                  25                  30

Tyr Gly Trp Tyr Gln Gln Lys Ala Pro Gly Ser Ala Pro Val Thr Leu
            35                  40                  45

Ile Tyr Tyr Asn Asn Lys Arg Pro Ser Asp Ile Pro Ser Arg Phe Ser
        50                  55                  60

Gly Ser Leu Ser Gly Ser Thr Asn Thr Leu Thr Ile Thr Gly Val Arg
65              70                  75                  80

Ala Asp Asp Glu Ala Val Tyr Phe Cys Gly Ser Ala Asp Asn Ser Gly
                85                  90                  95

Ala Ala Phe Gly Ala Gly Thr Thr Leu Thr Val Leu
            100                 105

<210> SEQ ID NO 5
<211> LENGTH: 5
<212> TYPE: PRT
<213> ORGANISM: Gallus gallus

<400> SEQUENCE: 5

Ser Phe Asn Met Phe
1               5

<210> SEQ ID NO 6
<211> LENGTH: 17
<212> TYPE: PRT
<213> ORGANISM: Gallus gallus

<400> SEQUENCE: 6

Gly Ile Asp Asp Asp Gly Ser Tyr Pro Asn Tyr Gly Ser Ala Val Lys
1               5                   10                  15

Gly

<210> SEQ ID NO 7
<211> LENGTH: 17
<212> TYPE: PRT

<213> ORGANISM: Gallus gallus

<400> SEQUENCE: 7

Ser Gly Tyr Gly Gly Ser Trp Gly Gly Tyr Ile Ala Asp Asp Ile Asp
1               5                   10                  15

Ala

<210> SEQ ID NO 8
<211> LENGTH: 13
<212> TYPE: PRT
<213> ORGANISM: Gallus gallus

<400> SEQUENCE: 8

Ser Gly Gly Gly Ser Tyr Ala Gly Ser Tyr Tyr Tyr Gly
1               5                   10

<210> SEQ ID NO 9
<211> LENGTH: 13
<212> TYPE: PRT
<213> ORGANISM: Gallus gallus

<400> SEQUENCE: 9

Ser Gly Asp Gly Ser Tyr Ala Gly Ser Tyr Tyr Tyr Gly
1               5                   10

<210> SEQ ID NO 10
<211> LENGTH: 14
<212> TYPE: PRT
<213> ORGANISM: Gallus gallus

<400> SEQUENCE: 10

Ser Gly Ser Asp Ser Ser Tyr Ala Gly Ser Tyr Tyr Tyr Gly
1               5                   10

<210> SEQ ID NO 11
<211> LENGTH: 7
<212> TYPE: PRT
<213> ORGANISM: Gallus gallus

<400> SEQUENCE: 11

Tyr Asn Asn Lys Arg Pro Ser
1               5

<210> SEQ ID NO 12
<211> LENGTH: 9
<212> TYPE: PRT
<213> ORGANISM: Gallus gallus

<400> SEQUENCE: 12

Gly Ser Ala Asp Asn Ser Gly Ala Ala
1               5

<210> SEQ ID NO 13
<211> LENGTH: 125
<212> TYPE: PRT
<213> ORGANISM: Gallus gallus

<400> SEQUENCE: 13

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Asn
            20                  25                  30

Ala Met Gly Trp Val Arg Gln Ala Pro Gly Lys Gly Leu Glu Trp Val

```
            35                  40                  45
Ala Gly Ile Asp Asp Gly Ser Gly Thr Arg Tyr Ala Pro Ala Val
 50                  55                  60

Lys Gly Arg Ala Thr Ile Ser Arg Asp Asn Gly Gln Ser Thr Leu Arg
 65                  70                  75                  80

Leu Gln Leu Asn Asn Leu Arg Ala Glu Asp Thr Gly Thr Tyr Tyr Cys
                 85                  90                  95

Thr Lys Cys Ala Tyr Ser Ser Gly Cys Asp Tyr Glu Gly Gly Tyr Ile
                100                 105                 110

Asp Ala Trp Gly His Gly Thr Glu Val Ile Val Ser Ser
            115                 120                 125

<210> SEQ ID NO 14
<211> LENGTH: 5
<212> TYPE: PRT
<213> ORGANISM: Gallus gallus

<400> SEQUENCE: 14

Ser Asn Ala Met Gly
 1               5

<210> SEQ ID NO 15
<211> LENGTH: 17
<212> TYPE: PRT
<213> ORGANISM: Gallus gallus

<400> SEQUENCE: 15

Gly Ile Asp Asp Asp Gly Ser Gly Thr Arg Tyr Ala Pro Ala Val Lys
 1               5                  10                  15

Gly

<210> SEQ ID NO 16
<211> LENGTH: 16
<212> TYPE: PRT
<213> ORGANISM: Gallus gallus

<400> SEQUENCE: 16

Cys Ala Tyr Ser Ser Gly Cys Asp Tyr Glu Gly Gly Tyr Ile Asp Ala
 1               5                  10                  15

<210> SEQ ID NO 17
<211> LENGTH: 107
<212> TYPE: PRT
<213> ORGANISM: Gallus gallus

<400> SEQUENCE: 17

Ala Leu Thr Gln Pro Ala Ser Val Ser Ala Asn Leu Gly Gly Thr Val
 1               5                  10                  15

Lys Ile Thr Cys Ser Gly Gly Ser Tyr Ala Gly Ser Tyr Tyr Tyr
             20                  25                  30

Gly Trp Tyr Gln Gln Lys Ser Pro Gly Ser Ala Pro Val Thr Val Ile
             35                  40                  45

Tyr Asp Asn Asp Lys Arg Pro Ser Asp Ile Pro Ser Arg Phe Ser Gly
 50                  55                  60

Ser Leu Ser Gly Ser Thr Asn Thr Leu Thr Ile Thr Gly Val Arg Ala
 65                  70                  75                  80

Asp Asp Glu Ala Val Tyr Phe Cys Gly Ser Ala Asp Asn Ser Gly Ala
                 85                  90                  95

Ala Phe Gly Ala Gly Thr Thr Leu Thr Val Leu
```

<210> SEQ ID NO 18
<211> LENGTH: 7
<212> TYPE: PRT
<213> ORGANISM: Gallus gallus

<400> SEQUENCE: 18

Asp Asn Asp Lys Arg Pro Ser
 1               5

<210> SEQ ID NO 19
<211> LENGTH: 378
<212> TYPE: DNA
<213> ORGANISM: Gallus gallus

<400> SEQUENCE: 19

```
gccgtgacgt tggacgagtc cggggcggc ctccagacgc ccggaggagc gctcagcctc    60
gtctgcaagg cctccgggtt caccttcagc agcttcaaca tgttctgggt gcgacaggag   120
cccggcaaag ggctggagtg ggtcgctggt attgatgatg atggtagtta cccaaactac   180
gggtcggcgg tgaagggccg tgccaccatc tcgagggaca cgggcagag cacactgagg    240
ctgcagctga caaacctcag ggctgaggac accggcacct acttctgcgc caaaagtggt   300
tatggtggta gttggggtgg ttatattgct gatgatatcg acgcatgggg ccacgggacc   360
gaagtcatcg tctcctcc                                                378
```

<210> SEQ ID NO 20
<211> LENGTH: 322
<212> TYPE: DNA
<213> ORGANISM: Gallus gallus

<400> SEQUENCE: 20

```
gcgctgactc agcctgcctc ggtgtcagca aacccaggag aaaccgtcaa gatcacctgc    60
tccggggtg gcagctatgc tggaagttac tattatggct ggtaccagca gaaggcacct   120
ggcagtgccc ctgtcactct gatctattac aacaacaaga ccctcggaca tcccttca    180
cgattctccg gttccctatc cggctccaca aacacattaa ccatcactgg ggtccgagcc   240
gatgacgagg ctgtctattt ctgtgggagt gcagacaaca gtggtgctgc atttggggcc   300
gggacaaccc tgacagtact tg                                            322
```

<210> SEQ ID NO 21
<211> LENGTH: 322
<212> TYPE: DNA
<213> ORGANISM: Gallus gallus

<400> SEQUENCE: 21

```
gcgctgactc agcctgcctc ggtgtcagca aacccaggag aaaccgtcaa gatcacctgc    60
tccggggatg gcagctatgc tggaagttac tattatggct ggtaccagca gaaggcacct   120
ggcagtgccc ctgtcactct gatctattac aacaacaaga ccctcggaca tcccttca    180
cgattctccg gttccctatc cggctccaca aacacattaa ccatcactgg ggtccgagcc   240
gatgacgagg ctgtctattt ctgtgggagt gcagacaaca gtggtgctgc atttggggcc   300
gggacaaccc tgacagtact tg                                            322
```

<210> SEQ ID NO 22
<211> LENGTH: 325
<212> TYPE: DNA

<213> ORGANISM: Gallus gallus

<400> SEQUENCE: 22

```
gcgctgactc agcctgcctc ggtgtcagca aacccaggag aaaccgtcaa gatcacctgc      60
tccgggagtg acagcagcta tgctggaagt tactattatg ctggtacca gcagaaggca     120
cctggcagtg cccctgtcac tctgatctat acaacaaca agagaccctc ggacatccct     180
tcacgattct ccggttccct atccggctcc acaaacacat taaccatcac tggggtccga    240
gccgatgacg aggctgtcta tttctgtggg agtgcagaca acagtggtgc tgcatttggg    300
gccgggacaa ccctgacagt acttg                                          325
```

<210> SEQ ID NO 23
<211> LENGTH: 375
<212> TYPE: DNA
<213> ORGANISM: Gallus gallus

<400> SEQUENCE: 23

```
gccgtgacgt tggacgagtc cggggggcggc ctccagacgc ccggggagc gctcagcctc      60
gtctgcaagg cctccgggtt caccttcagc agtaacgcca tgggttgggt gcgacaggcg    120
cccggcaagg ggctggagtg gtcgctggt attgatgatg atggtagtgg cacaagatac     180
gcgccggcgg tgaagggccg tgccaccatc tcgagggaca cgggcagag cacactgagg    240
ctgcagctga caacctcag ggctgaggac accggcacct actactgcac gaaatgtgct    300
tacagtagtg gttgtgatta tgaaggtggt tatatcgacg catgggcca cgggaccgaa    360
gtcatcgtct cctcc                                                     375
```

<210> SEQ ID NO 24
<211> LENGTH: 322
<212> TYPE: DNA
<213> ORGANISM: Gallus gallus

<400> SEQUENCE: 24

```
gcgctgactc agccggcctc ggtgtcagca aacctgggag gaaccgtcaa gatcacctgc      60
tccgggggtg gcagctatgc tggaagttac tattatggct ggtaccagca gaagtctcct    120
ggcagtgccc ctgtcactgt gatctatgac aacgacaaga gaccctcgga catcccttca    180
cgattctccg gttccctatc cggctccaca aacacattaa ccatcactgg ggtccgagcc    240
gatgacgagg ctgtctattt ctgtgggagt gcagacaaca gtggtgctgc atttggggcc    300
gggacaaccc tgaccgtcct ag                                             322
```

<210> SEQ ID NO 25
<211> LENGTH: 5
<212> TYPE: PRT
<213> ORGANISM: Artificial Sequence
<220> FEATURE:
<223> OTHER INFORMATION: Glycine-serine polymer linker

<400> SEQUENCE: 25

Gly Ser Gly Gly Ser
 1               5

<210> SEQ ID NO 26
<211> LENGTH: 5
<212> TYPE: PRT
<213> ORGANISM: Artificial Sequence
<220> FEATURE:
<223> OTHER INFORMATION: Glycine-serine polymer linker -continued

```
<400> SEQUENCE: 26

Gly Gly Gly Gly Ser
1               5

<210> SEQ ID NO 27
<211> LENGTH: 4
<212> TYPE: PRT
<213> ORGANISM: Artificial Sequence
<220> FEATURE:
<223> OTHER INFORMATION: Glycine-serine polymer linker

<400> SEQUENCE: 27

Gly Gly Gly Ser
1

<210> SEQ ID NO 28
<211> LENGTH: 581
<212> TYPE: PRT
<213> ORGANISM: Homo sapiens

<400> SEQUENCE: 28

Met Gln Arg Pro Gly Pro Arg Leu Trp Leu Val Leu Gln Val Met Gly
1               5                   10                  15

Ser Cys Ala Ala Ile Ser Ser Met Asp Met Glu Arg Pro Gly Asp Gly
                20                  25                  30

Lys Cys Gln Pro Ile Glu Ile Pro Met Cys Lys Asp Ile Gly Tyr Asn
            35                  40                  45

Met Thr Arg Met Pro Asn Leu Met Gly His Glu Asn Gln Arg Glu Ala
        50                  55                  60

Ala Ile Gln Leu His Glu Phe Ala Pro Leu Val Glu Tyr Gly Cys His
65                  70                  75                  80

Gly His Leu Arg Phe Phe Leu Cys Ser Leu Tyr Ala Pro Met Cys Thr
                85                  90                  95

Glu Gln Val Ser Thr Pro Ile Pro Ala Cys Arg Val Met Cys Glu Gln
            100                 105                 110

Ala Arg Leu Lys Cys Ser Pro Ile Met Glu Gln Phe Asn Phe Lys Trp
        115                 120                 125

Pro Asp Ser Leu Asp Cys Arg Lys Leu Pro Asn Lys Asn Asp Pro Asn
130                 135                 140

Tyr Leu Cys Met Glu Ala Pro Asn Asn Gly Ser Asp Glu Pro Thr Arg
145                 150                 155                 160

Gly Ser Gly Leu Phe Pro Pro Leu Phe Arg Pro Gln Arg Pro His Ser
                165                 170                 175

Ala Gln Glu His Pro Leu Lys Asp Gly Gly Pro Gly Arg Gly Gly Cys
            180                 185                 190

Asp Asn Pro Gly Lys Phe His His Val Glu Lys Ser Ala Ser Cys Ala
        195                 200                 205

Pro Leu Cys Thr Pro Gly Val Asp Val Tyr Trp Ser Arg Glu Asp Lys
210                 215                 220

Arg Phe Ala Val Val Trp Leu Ala Ile Trp Ala Val Leu Cys Phe Phe
225                 230                 235                 240

Ser Ser Ala Phe Thr Val Leu Thr Phe Leu Ile Asp Pro Ala Arg Phe
                245                 250                 255

Arg Tyr Pro Glu Arg Pro Ile Ile Phe Leu Ser Met Cys Tyr Cys Val
            260                 265                 270

Tyr Ser Val Gly Tyr Leu Ile Arg Leu Phe Ala Gly Ala Glu Ser Ile
        275                 280                 285
```

```
Ala Cys Asp Arg Asp Ser Gly Gln Leu Tyr Val Ile Gln Glu Gly Leu
            290                 295                 300

Glu Ser Thr Gly Cys Thr Leu Val Phe Leu Val Leu Tyr Tyr Phe Gly
305                 310                 315                 320

Met Ala Ser Ser Leu Trp Trp Val Val Leu Thr Leu Thr Trp Phe Leu
                325                 330                 335

Ala Ala Gly Lys Lys Trp Gly His Glu Ala Ile Glu Ala Asn Ser Ser
            340                 345                 350

Tyr Phe His Leu Ala Ala Trp Ala Ile Pro Ala Val Lys Thr Ile Leu
            355                 360                 365

Ile Leu Val Met Arg Arg Val Ala Gly Asp Glu Leu Thr Gly Val Cys
370                 375                 380

Tyr Val Gly Ser Met Asp Val Asn Ala Leu Thr Gly Phe Val Leu Ile
385                 390                 395                 400

Pro Leu Ala Cys Tyr Leu Val Ile Gly Thr Ser Phe Ile Leu Ser Gly
                405                 410                 415

Phe Val Ala Leu Phe His Ile Arg Arg Val Met Lys Thr Gly Gly Glu
            420                 425                 430

Asn Thr Asp Lys Leu Glu Lys Leu Met Val Arg Ile Gly Leu Phe Ser
            435                 440                 445

Val Leu Tyr Thr Val Pro Ala Thr Cys Val Ile Ala Cys Tyr Phe Tyr
450                 455                 460

Glu Arg Leu Asn Met Asp Tyr Trp Lys Ile Leu Ala Ala Gln His Lys
465                 470                 475                 480

Cys Lys Met Asn Asn Gln Thr Lys Thr Leu Asp Cys Leu Met Ala Ala
                485                 490                 495

Ser Ile Pro Ala Val Glu Ile Phe Met Val Lys Ile Phe Met Leu Leu
            500                 505                 510

Val Val Gly Ile Thr Ser Gly Met Trp Ile Trp Thr Ser Lys Thr Leu
            515                 520                 525

Gln Ser Trp Gln Gln Val Cys Ser Arg Arg Leu Lys Lys Ser Arg
530                 535                 540

Arg Lys Pro Ala Ser Val Ile Thr Ser Gly Ile Tyr Lys Lys Ala
545                 550                 555                 560

Gln His Pro Gln Lys Thr His His Gly Lys Tyr Glu Ile Pro Ala Gln
                565                 570                 575

Ser Pro Thr Cys Val
            580

<210> SEQ ID NO 29
<211> LENGTH: 212
<212> TYPE: PRT
<213> ORGANISM: Artificial Sequence
<220> FEATURE:
<223> OTHER INFORMATION: Humanized L9.3 light chain with human lambda
      light chain constant region

<400> SEQUENCE: 29

Glu Leu Thr Gln Pro Pro Ser Val Ser Val Ser Pro Gly Gln Thr Ala
1               5                   10                  15

Arg Ile Thr Cys Ser Gly Asp Gly Ser Tyr Ala Gly Ser Tyr Tyr Tyr
                20                  25                  30

Gly Trp Tyr Gln Gln Lys Pro Gly Gln Ala Pro Val Thr Leu Ile Tyr
            35                  40                  45

Tyr Asn Asn Lys Arg Pro Ser Gly Ile Pro Glu Arg Phe Ser Gly Ser
```

```
                50                  55                  60
Leu Ser Gly Ser Thr Asn Thr Leu Thr Ile Ser Gly Val Gln Ala Glu
 65                  70                  75                  80

Asp Glu Ala Asp Tyr Tyr Cys Gly Ser Ala Asp Asn Ser Gly Ala Ala
                 85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Glu Glu Leu Gln Ala Asn
            115                 120                 125

Lys Ala Thr Leu Val Cys Leu Ile Ser Asp Phe Tyr Pro Gly Ala Val
        130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210
```

```
<210> SEQ ID NO 30
<211> LENGTH: 696
<212> TYPE: DNA
<213> ORGANISM: Artificial Sequence
<220> FEATURE:
<223> OTHER INFORMATION: Coding sequence for humanized L9.3 light chain

<400> SEQUENCE: 30
atggcctgga ttcctctact tctccccctc ctcactctct gcacaggatc cgaggccgag    60
ttgacgcagc cccccgtcagt ctcggtgagc cccggacaaa cagcaaggat tacttgttcg   120
ggggatggct catatgctgg ttcctactat tacgggtggt atcaacagaa accggggcag   180
gcccctgtga ccctcatcta ctacaacaat aagcgcccat caggaatccc cgaacggttt   240
agcggttcgc ttagcggatc gacgaatacg ctcactatct ccggagtaca ggcggaggac   300
gaagccgact attactgcgg gtccgcggat aactcgggag cggcattcgg gggtggcacc   360
aagctgacag tcttgggtca gcccaaggct gccccctcgg tcaccctgtt cccgccctcc   420
tctgaggagc ttcaagccaa caaggccaca ctggtgtgtc tcataagtga cttctacccg   480
ggagccgtga cagtggcctg gaaggcagat agcagccccg tcaaggcggg agtggagacc   540
accacaccct ccaaacaaag caacaacaag tacgcggcca gcagctatct gagcctgacg   600
cctgagcagt ggaagtccca cagaagctac agctgccagg tcacgcatga agggagcacc   660
gtggagaaga cagtggcccc tacagaatgt tcatag                              696
```

```
<210> SEQ ID NO 31
<211> LENGTH: 456
<212> TYPE: PRT
<213> ORGANISM: Artificial Sequence
<220> FEATURE:
<223> OTHER INFORMATION: Humanized B9 heavy chain with human IgG1
      constant region

<400> SEQUENCE: 31

Glu Val Gln Leu Val Glu Ser Gly Gly Gly Leu Val Gln Pro Gly Gly
 1               5                  10                  15
```

-continued

Ser Leu Arg Leu Ser Cys Ala Ala Ser Gly Phe Thr Phe Ser Ser Phe
            20                  25                  30

Asn Met Phe Trp Val Arg Gln Ala Pro Gly Lys Gly Leu Glu Trp Val
        35                  40                  45

Ala Gly Ile Asp Asp Gly Ser Tyr Pro Asn Tyr Gly Ser Ala Val
 50                  55                  60

Lys Gly Arg Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ser Gly Tyr Gly Gly Ser Trp Gly Gly Tyr Ile Ala Asp Asp
            100                 105                 110

Ile Asp Ala Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Asp Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Glu Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly Lys
    450                 455

<210> SEQ ID NO 32
<211> LENGTH: 1428
<212> TYPE: DNA
<213> ORGANISM: Artificial Sequence
<220> FEATURE:
<223> OTHER INFORMATION: Coding sequence for humanized B9 heavy chain

<400> SEQUENCE: 32

| | | | | | |
|---|---|---|---|---|---|
| atggagttcg | gcctgagctg | gctgttcctg | gtggccatcc | ttaagggcgt | gcagtgcgag | 60 |
| gtacagctcg | tggaatcagg | tggagggctt | gtccaacccg | gagggtcctt | gcgcctgtcg | 120 |
| tgtgcggcct | ccggtttcac | gttttccagc | ttcaatatgt | tttgggtccg | gcaggcaccg | 180 |
| ggtaaaggt | tggaatgggt | agcgggaatc | gatgatgacg | gctcgtatcc | taattacggg | 240 |
| tcagctgtga | aggacgagc | caccatcagc | agagataact | cgaagaacac | actctacctt | 300 |
| caaatgaact | cactgagggc | agaggacacg | gcggtgtact | actgcgccaa | gtcgggatat | 360 |
| gggggctcat | ggggaggcta | tattgcggac | gacatcgatg | cgtggggaca | gggacattg | 420 |
| gtcactgtga | gctcggctag | caccaagggc | ccatcggtct | tccccctggc | acctcctcc | 480 |
| aagagcacct | ctgggggcac | agcggccctg | ggctgcctgg | tcaaggacta | cttccccgaa | 540 |
| ccggtgacgg | tgtcgtggaa | ctcaggcgcc | ctgaccagcg | gcgtgcacac | cttcccggct | 600 |
| gtcctacagt | cctcaggact | ctactccctc | agcagcgtgg | tgaccgtgcc | ctccagcagc | 660 |
| ttgggcaccc | agacctacat | ctgcaacgtg | aatcacaagc | ccagcaacac | caaggtggac | 720 |
| aagaaagttg | agcccaaatc | ttgtgacaaa | actcacacat | gcccaccgtg | cccagcacct | 780 |
| gaactcctgg | ggggaccgga | cgtcttcctc | ttccccccaa | aacccaagga | caccctcatg | 840 |
| atctcccgga | cccctgaggt | cacatgcgtg | gtggtggacg | tgagccacga | agaccctgag | 900 |
| gtcaagttca | actggtacgt | ggacggcgtg | gaggtgcata | atgccaagac | aaagccgcgg | 960 |
| gaggagcagt | acaacagcac | gtaccgtgtg | gtcagcgtcc | tcaccgtcct | gcaccaggac | 1020 |
| tggctgaatg | gcaaggagta | caagtgcaag | gtctccaaca | aagccctccc | agccccccgag | 1080 |
| gagaaaacca | tctccaaagc | caaagggcag | ccccgagaac | cacaggtgta | caccctgccc | 1140 |
| ccatcccggg | atgagctgac | caagaaccag | gtcagcctga | cctgcctggt | caaaggcttc | 1200 |
| tatcccagcg | acatcgccgt | ggagtgggag | agcaatgggc | agccggagaa | caactacaag | 1260 |
| accacgcctc | ccgtgctgga | ctccgacggc | tccttcttcc | tctacagcaa | gctcaccgtg | 1320 |
| gacaagagca | ggtggcagca | ggggaacgtc | ttctcatgct | ccgtgatgca | tgaggctctg | 1380 |
| cacaaccact | acacacagaa | gagcctctcc | ctgtctccgg | gtaaatga | | 1428 |

<210> SEQ ID NO 33
<211> LENGTH: 993
<212> TYPE: DNA
<213> ORGANISM: Homo sapiens

<400> SEQUENCE: 33

| | | | | | |
|---|---|---|---|---|---|
| gctagcacca | agggcccatc | ggtcttcccc | ctggcaccct | cctccaagag | cacctctggg | 60 |
| ggcacagcgg | ccctgggctg | cctggtcaag | gactacttcc | ccgaaccggt | gacggtgtcg | 120 |
| tggaactcag | gcgccctgac | cagcggcgtg | cacaccttcc | cggctgtcct | acagtcctca | 180 |
| ggactctact | ccctcagcag | cgtggtgacc | gtgccctcca | gcagcttggg | cacccagacc | 240 |

-continued

```
tacatctgca acgtgaatca caagcccagc aacaccaagg tggacaagaa agttgagccc      300
aaatcttgtg acaaaactca cacatgccca ccgtgcccag cacctgaact cctgggggga      360
ccgtcagtct tcctcttccc cccaaaaccc aaggacaccc tcatgatctc ccggacccct      420
gaggtcacat gcgtggtggt ggacgtgagc cacgaagacc ctgaggtcaa gttcaactgg      480
tacgtggacg gcgtggaggt gcataatgcc aagacaaagc cgcgggagga gcagtacaac      540
agcacgtacc gtgtggtcag cgtcctcacc gtcctgcacc aggactggct gaatggcaag      600
gagtacaagt gcaaggtctc caacaaagcc ctcccagccc ccatcgagaa aaccatctcc      660
aaagccaaag gcagccccg agaaccacag gtgtacaccc tgcccccatc ccgggatgag       720
ctgaccaaga accaggtcag cctgacctgc ctggtcaaag gcttctatcc cagcgacatc      780
gccgtggagt gggagagcaa tgggcagccg gagaacaact acaagaccac gcctcccgtg      840
ctggactccg acggctcctt cttcctctac agcaagctca ccgtggacaa gagcaggtgg      900
cagcagggga acgtcttctc atgctccgtg atgcatgagg ctctgcacaa ccactacaca      960
cagaagagcc tctccctgtc tccgggtaaa tga                                   993
```

<210> SEQ ID NO 34
<211> LENGTH: 330
<212> TYPE: PRT
<213> ORGANISM: Homo sapiens

<400> SEQUENCE: 34

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 35
<211> LENGTH: 321
<212> TYPE: DNA
<213> ORGANISM: Homo sapiens

<400> SEQUENCE: 35
ggtcagccca aggctgcccc ctcggtcacc ctgttcccgc cctcctctga ggagcttcaa      60
gccaacaagg ccacactggt gtgtctcata agtgacttct acccgggagc cgtgacagtg     120
gcctggaagg cagatagcag ccccgtcaag gcgggagtgg agaccaccac accctccaaa     180
caaagcaaca acaagtacgc ggccagcagc tatctgagcc tgacgcctga gcagtggaag     240
tcccacagaa gctacagctg ccaggtcacg catgaaggga gcaccgtgga agacagtgt     300 gcccctacag aatgttcata g                                              321

<210> SEQ ID NO 36
<211> LENGTH: 106
<212> TYPE: PRT
<213> ORGANISM: Homo sapiens

<400> SEQUENCE: 36

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
            85                  90                  95

Glu Lys Thr Val Ala Pro Thr Glu Cys Ser
            100                 105

<210> SEQ ID NO 37
<211> LENGTH: 106
<212> TYPE: PRT
<213> ORGANISM: Artificial Sequence
<220> FEATURE:
<223> OTHER INFORMATION: Humanized L9.3 light chain variable region

<400> SEQUENCE: 37

Glu Leu Thr Gln Pro Pro Ser Val Ser Val Ser Pro Gly Gln Thr Ala

```
                 1               5                  10                 15
Arg Ile Thr Cys Ser Gly Asp Gly Ser Tyr Ala Gly Ser Tyr Tyr Tyr
                20                 25                 30

Gly Trp Tyr Gln Gln Lys Pro Gly Gln Ala Pro Val Thr Leu Ile Tyr
        35                 40                 45

Tyr Asn Asn Lys Arg Pro Ser Gly Ile Pro Glu Arg Phe Ser Gly Ser
    50                 55                 60

Leu Ser Gly Ser Thr Asn Thr Leu Thr Ile Ser Gly Val Gln Ala Glu
65                 70                 75                 80

Asp Glu Ala Asp Tyr Tyr Cys Gly Ser Ala Asp Asn Ser Gly Ala Ala
                85                 90                 95

Phe Gly Gly Gly Thr Lys Leu Thr Val Leu
                100                105

<210> SEQ ID NO 38
<211> LENGTH: 108
<212> TYPE: PRT
<213> ORGANISM: Artificial Sequence
<220> FEATURE:
<223> OTHER INFORMATION: Human V lambda subgroup III consensus sequence
      with CDR amino acids denoted by Xaa
<220> FEATURE:
<221> NAME/KEY: VARIANT
<222> LOCATION: 23, 24, 25, 26, 27, 28, 29, 30, 31, 32, 33, 34, 35, 51,
      52, 53, 54, 55, 56, 57, 90, 91, 92, 93, 94, 95, 96, 97, 98
<223> OTHER INFORMATION: Xaa = Any Amino Acid

<400> SEQUENCE: 38

Ser Tyr Glu Leu Thr Gln Pro Pro Ser Val Ser Val Ser Pro Gly Gln
1               5                  10                 15

Thr Ala Arg Ile Thr Cys Xaa Xaa Xaa Xaa Xaa Xaa Xaa Xaa Xaa
                20                 25                 30

Xaa Xaa Xaa Trp Tyr Gln Gln Lys Pro Gly Gln Ala Pro Val Leu Val
        35                 40                 45

Ile Tyr Xaa Xaa Xaa Xaa Xaa Xaa Gly Ile Pro Glu Arg Phe Ser
    50                 55                 60

Gly Ser Asn Ser Gly Asn Thr Ala Thr Leu Thr Ile Ser Gly Val Gln
65                 70                 75                 80

Ala Glu Asp Glu Ala Asp Tyr Tyr Cys Xaa Xaa Xaa Xaa Xaa Xaa
                85                 90                 95

Xaa Xaa Phe Gly Gly Gly Thr Lys Leu Thr Val Leu
                100                105

<210> SEQ ID NO 39
<211> LENGTH: 126
<212> TYPE: PRT
<213> ORGANISM: Artificial Sequence
<220> FEATURE:
<223> OTHER INFORMATION: Humanized B9 heavy chain variable region

<400> SEQUENCE: 39

Glu Val Gln Leu Val Glu Ser Gly Gly Gly Leu Val Gln Pro Gly Gly
1               5                  10                 15

Ser Leu Arg Leu Ser Cys Ala Ala Ser Gly Phe Thr Phe Ser Ser Phe
                20                 25                 30

Asn Met Phe Trp Val Arg Gln Ala Pro Gly Lys Gly Leu Glu Trp Val
        35                 40                 45

Ala Gly Ile Asp Asp Gly Ser Tyr Pro Asn Tyr Gly Ser Ala Val
    50                 55                 60
```

```
Lys Gly Arg Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Gly Tyr Gly Gly Ser Trp Gly Gly Tyr Ile Ala Asp Asp
            100                 105                 110

Ile Asp Ala Trp Gly Gln Gly Thr Leu Val Thr Val Ser Ser
            115                 120                 125

<210> SEQ ID NO 40
<211> LENGTH: 126
<212> TYPE: PRT
<213> ORGANISM: Artificial Sequence
<220> FEATURE:
<223> OTHER INFORMATION: Human VH subgroup III consensus sequence with
      CDR amino acids denoted by Xaa
<220> FEATURE:
<221> NAME/KEY: VARIANT
<222> LOCATION: 31, 32, 33, 34, 35, 50, 51, 52, 53, 54, 55, 56, 57, 58,
      59, 60, 61, 62, 63, 64, 65, 66, 99, 100, 101, 102, 103, 104,
      105, 106, 107, 108, 109, 110, 111, 112, 113, 114, 115
<223> OTHER INFORMATION: Xaa = Any Amino Acid

<400> SEQUENCE: 40

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Xaa Xaa
                 20                  25                  30

Xaa Xaa Xaa Trp Val Arg Gln Ala Pro Gly Lys Gly Leu Glu Trp Val
            35                  40                  45

Ser Xaa Xaa Xaa Xaa Xaa Xaa Xaa Xaa Xaa Xaa Xaa Xaa Xaa Xaa Xaa
     50                  55                  60

Xaa Xaa Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Xaa Xaa Xaa Xaa Xaa Xaa Xaa Xaa Xaa Xaa Xaa Xaa Xaa Xaa
            100                 105                 110

Xaa Xaa Xaa Trp Gly Gln Gly Thr Leu Val Thr Val Ser Ser
            115                 120                 125
```

ANTI-FZD10 MONOCLONAL ANTIBODIES AND METHODS FOR THEIR USE

CROSS-REFERENCE TO RELATED APPLICATION

This application claims the benefit under 35 U.S.C. §119 (e) of U.S. Provisional Patent Application Nos. 61/523,102, filed Aug. 12, 2011; and 61/548,110, filed Oct. 17, 2011; which applications are incorporated herein by reference in their entirety.

SEQUENCE LISTING

The Sequence Listing associated with this application is provided in text format in lieu of a paper copy, and is hereby incorporated by reference into the specification. The name of the text file containing the Sequence Listing is 980087_404_SEQUENCE_LISTING.txt. The text file is about 35 KB, was created on Aug. 9, 2012, and is being submitted electronically via EFS-Web.

BACKGROUND

1. Technical Field

The presently disclosed invention embodiments relate generally to anti-FZD10 antibodies and to methods of using anti-FZD10 antibodies. In particular, the anti-FZD10 antibodies and the methods described herein are useful for the treatment of diseases associated with expression (typically overexpression) of FZD10, such as a variety of cancers, and for the identification of treatment regimens that comprise administration of anti-FZD10 antibodies alone or in combination with other agents. In addition, the methods are useful for regulating the growth and differentiation of stem cells, such as embryonic, pluripotent, and cancer stem cells, with therapeutic implications in tissue regeneration and transplantation as well as cancer.

2. Description of the Related Art

Frizzled antigens are a family of G protein coupled receptor-like cell surface receptors that mediate biological signal transduction and that have binding sites for Wnt protein ligands, which are secreted molecules that act as selective upregulators of specific gene expression. Members of the Frizzled and Wnt families of receptor-ligand pairs regulate embryonic development, and may also play a role in cellular proliferation and in determining the ultimate fate of cells during embryogenesis. Most frizzled receptors are functionally coupled to the β-catenin or "canonical" Wnt signaling pathway, in which Wnt ligand binding to a cell surface frizzled receptor leads sequentially to the activation of cytoplasmic dishevelled proteins, inhibition of intracellular GSK-3 kinase, nuclear accumulation of β-catenin and, through interaction of β-catenin in the nucleus with TCF or LEF transcription factors, transcriptional activation of Wnt target genes. Other Wnt signaling pathways involving protein kinase C (PKC) and calcium flux have been described for some Frizzled and Wnt family members, but it is not yet clear if these all represent distinct pathways or if any one or more of them may be integrated with the canonical Wnt signaling pathway.

There are 19 Wnt and 10 Frizzled (Fz or FZD) genes identified thus far in the human genome database (Venter et al., *Science* 291:1304-1351 (2001)). There are also five secreted Frizzled forms. Each Fz gene encodes an integral membrane protein with a large N-terminal extracellular portion, seven putative transmembrane domains, and a cytoplasmic tail (Wang et al., *J. Biol. Chem.* 271, 4468-4476 (1996); Vinson et al., *Nature (London)* 338, 263-264 (1989)). Near the $NH_2$ terminus of the extracellular portion is a cysteine-rich domain (CRD) that is well conserved among other members of the FZ family (Wang et al., *J. Biol. Chem.* 271, 4468-4476 (1996)). The CRD, comprised of 110 amino acid residues, including ten invariant cysteines, is the putative binding site for Wnt ligands (Bhanot et al., *Nature (London)* 382, 225-230 (1996). Frizzled receptors can dimerize in the cell membrane, and dimerization is correlated with activation of the Wnt/β-catenin pathway (Carron et al., *Journal of Cell Science*, 116:2541-2550 (2003)).

A human Fz gene family member, Frizzled-10 (FZD10), has been cloned and characterized (Koike et al., *Biochem Biophys Res Commun.* 262(1):39-43 (1999)). Analysis of the FZD10 nucleotide sequence showed that the human FZD10 gene encodes a seven-transmembrane-receptor of 581 amino acids, including an amino-terminal cysteine-rich domain and a carboxy-terminal Ser/Thr-Xxx-Val motif. FZD10-encoding mRNA (4.0 kb) was detected in placenta, fetal kidney, fetal lung and brain. In adult brain, FZD10 mRNA was abundant in the cerebellum. The FZD10 gene was mapped to human chromosome 12q24.33. FZD10 shares 65.7% amino-acid identity with Frizzled-9 (FZD9). FZD10 and FZD9 constitute a subfamily among the Frizzled genes. FZD10 is the receptor for the Wnt ligand proteins WNT7a and WNT7b. There is 93% identity between mouse and human FZD10. A human FZD10 (also known as FZ10, CD350, FzE7, hFZ10, frizzled homologue 10, FZ-10) amino acid sequence is set forth in SEQ ID NO:28.

In normal tissues, expression levels of the FZD10 protein are very low or absent (e.g., not detectable by conventional means) in vital organs, and present at low levels in superficial mucosa of the stomach and colon, in kidney proximal and distal tubules, in endometrial stroma and in placenta. Readily detectable FZD10 expression, however, has been shown in various cancers, such as synovial sarcoma (92%; Nagayama et al., 2002 *Cancer Res.* 62:5859), gastric carcinoma (40%; Kirikoshi et al., 2001 *Int. J. Oncol.* 19:767) and colorectal carcinoma (25%; Nagayama et al., 2009 *Cancer Sci.* 100: 405). Specific siRNA knockdown of FZD10 expression resulted in synovial sarcoma cell growth inhibition in vitro, and polyclonal anti-FZD10 antibodies were shown to mediate as antibody dependent cell-mediated cytotoxicity (ADCC) against FZD10-overexpressing synovial sarcoma cells in vitro, and to inhibit synovial sarcoma xenograft tumor growth in vivo. (Nagayama et al., 2005 *Oncogene* 24:6201). A radiolabeled anti-FZD10 monoclonal antibody was internalized by antigen-bearing tumor cells and dramatically suppressed synovial sarcoma xenograft tumor growth in vivo. (Fukukawa et al., 2008 *Cancer Sci.* 99:437).

Wnt-FZD pathways are thus activated in many cancers, yet the FZD receptors have yet to be effectively developed as therapeutic targets. Clearly there is a need for anti-FZD10 monoclonal antibodies that are amenable to clinical development. The presently described invention embodiments address this need and offer other related advantages.

BRIEF SUMMARY

In certain embodiments according to the present disclosure, there is provided a composition comprising an isolated anti-FZD10 antibody which comprises an isolated antibody, or an antigen-binding fragment thereof, that binds to human FZD10, and which comprises a heavy chain variable region comprising the VHCDR1, VHCDR2 and VHCDR3 amino acid sequences set forth in SEQ ID NOs:5, 6 and 7, respectively, and a light chain variable region comprising the VLCDR1, VLCDR2 and VLCDR3 amino acid sequences set forth in: SEQ ID NOs:9, 11, 12, respectively, or SEQ ID NOs:10, 11, 12, respectively. In one embodiment, the isolated antibody, or an antigen-binding fragment thereof, comprises a heavy chain variable region which comprises the VHCDR1, VHCDR2 and VHCDR3 amino acid sequences set forth in SEQ ID NOs:5, 6, and 7, respectively, and the antibody comprises a light chain variable region which comprises the VLCDR1, VLCDR2 and VLCDR3 amino acid sequences set forth in SEQ ID NOs:9, 11, and 12, respectively. In another embodiment the light chain variable region comprises the amino acid sequence set forth in SEQ ID NO:3. In yet another embodiment the heavy chain variable region comprises the amino acid sequence set forth in SEQ ID NO:1.

In certain embodiments, an isolated antibody, or an antigen-binding fragment thereof as described herein comprises a heavy chain variable region which comprises the VHCDR1, VHCDR2 and VHCDR3 amino acid sequences set forth in SEQ ID NOs:5, 6, and 7, respectively, and comprises a light chain variable region comprising the VLCDR1, VLCDR2 and VLCDR3 amino acid sequences set forth in SEQ ID NOs:10, 11, and 12, respectively. In certain embodiments, an isolated antibody, or an antigen-binding fragment thereof as described herein comprises a light chain variable region comprising the VLCDR1, VLCDR2 and VLCDR3 amino acid sequences set forth in SEQ ID NOs:10, 11, and 12, respectively and the heavy chain variable region of the antibody comprises the amino acid sequence set forth in SEQ ID NO:1.

In another embodiment, the isolated antibody, or an antigen-binding fragment thereof as described herein comprises a heavy chain variable region which comprises the VHCDR1, VHCDR2 and VHCDR3 amino acid sequences set forth in SEQ ID NOs:5, 6, and 7, respectively, and comprises a light chain variable region comprising the amino acid sequence set forth in SEQ ID NO:4. In certain embodiments, the isolated antibodies described herein, or antigen-binding fragments thereof, are humanized. In one embodiment, a humanized antibody as described herein comprises a light chain variable domain comprising the amino acid sequence set forth in SEQ ID NO:37.

In one embodiment, an isolated antibody or antigen-binding fragment thereof, comprises a light chain variable domain comprising the amino acid sequence set forth in SEQ ID NO:37 and further comprises a heavy chain variable domain that comprises an amino acid sequence having at least 95% identity to the amino acid sequence of SEQ ID NO:39, or that comprises the amino acid sequence set forth in SEQ ID NO:39. In one embodiment, an isolated antibody or antigen-binding fragment thereof, comprises a light chain variable domain comprising the amino acid sequence set forth in SEQ ID NO:37 and further comprises a heavy chain variable domain that comprises an amino acid sequence having at least 95% identity to the amino acid sequence of SEQ ID NO:39, or that comprises the amino acid sequence set forth in SEQ ID NO:39 and further comprises a human lambda light chain constant region comprising the amino acid sequence set forth in SEQ ID NO:36.

In one embodiment, an isolated antibody or antigen-binding fragment thereof, comprises a light chain variable domain comprising the amino acid sequence set forth in SEQ ID NO:37 and further comprises a heavy chain variable domain that comprises an amino acid sequence having at least 95% identity to the amino acid sequence of SEQ ID NO:39, or that comprises the amino acid sequence set forth in SEQ ID NO:39 and further comprising a human IgG1 constant region comprising the amino acid sequence set forth in SEQ ID NO:34. In certain embodiments, a humanized antibody, or antigen-binding fragment thereof, as described herein comprises a light chain comprising the amino acid sequence set forth in SEQ ID NO:29 and a heavy chain comprising the amino acid sequence set forth in SEQ ID NO:31.

In one embodiment, the isolated antibody, or an antigen-binding fragment thereof, that binds to human FZD10 comprises a heavy chain variable region comprising the amino acid sequence set forth in SEQ ID NO:1. In certain embodiments, the isolated antibody has a heavy chain variable region comprising the amino acid sequence set forth in SEQ ID NO:1 and further comprises a light chain variable region comprising an amino acid sequence having at least 95% identity to the amino acid sequence set forth in SEQ ID NO:3, or further comprises a light chain variable region comprising the amino acid sequence set forth in SEQ ID NO:3. In certain embodiments, the isolated antibody has a heavy chain variable region comprising the amino acid sequence set forth in SEQ ID NO:1 and further comprises a light chain variable region comprising an amino acid sequence having at least 95% identity to the amino acid sequence set forth in SEQ ID NO:4, or further comprises a light chain variable region comprising the amino acid sequence set forth in SEQ ID NO:4. In certain embodiments, the isolated antibody has a heavy chain variable region comprising the amino acid sequence set forth in SEQ ID NO:1 and further comprises a light chain variable region comprising an amino acid sequence having at least 95% identity to the amino acid sequence set forth in SEQ ID NO:2, or further comprises a light chain variable region comprising the amino acid sequence set forth in SEQ ID NO:2.

In another embodiment, the isolated antibody, or an antigen-binding fragment thereof, that binds to human FZD10 comprises a light chain variable region comprising any one of the amino acid sequences set forth in SEQ ID NOs:2, 3, and 4. In one embodiment, the isolated antibody comprises a light chain variable region comprises SEQ ID NO:2 and further comprises a heavy chain variable region comprising an amino acid sequence having at least 95% identity to the amino acid sequence of SEQ ID NO:1. In one embodiment, the isolated antibody comprises a light chain variable region comprises SEQ ID NO:3 and further comprises a heavy chain variable region comprising an amino acid sequence having at least 95% identity to the amino acid sequence of SEQ ID NO:1. In one embodiment, the isolated antibody comprises a light chain variable region comprising SEQ ID NO:4 and further comprises a heavy chain variable region comprising an amino acid sequence having at least 95% identity to the amino acid sequence of SEQ ID NO:1.

In certain embodiments there is provided an isolated antibody that competes with the herein described anti-FZD10 antibody for binding to FZD10. In one embodiment, the isolated antibody binds to FZD10, wherein the antibody binds to FZD10 with a $K_D$ equal to or lower than 0.22 nM. In certain embodiments, the antibodies described herein that bind to FZD10 are single chain antibodies, ScFvs, univalent antibodies lacking a hinge region, or minibodies. In other embodiments, the antibodies, or an antigen-binding fragments thereof may be Fab or a Fab' fragments. In another embodiment, the isolated antibody, or an antigen-binding fragment thereof as described herein is a F(ab')$_2$ fragment or may be a whole antibody. In certain embodiments, the antibody is conjugated to a drug or a toxin. Illustrative toxins include, but are not limited to, saporin.

In one embodiment, an isolated antibody, or an antigen-binding fragment thereof as described herein comprises a human IgG Fc domain. In certain embodiments, the human IgG Fc domain is modified to obtain a modified antibody that has enhanced ADCC activity as compared to the antibody in which the human IgG Fc domain has not been modified. In other embodiments there are provided compositions comprising a physiologically acceptable carrier and a therapeutically effective amount of one or more of the herein described isolated anti-FZD10 antibodies, or antigen-binding fragments thereof.

In another embodiment there is provided a method for treating a patient having a disease associated with FZD10 expression, comprising administering to the patient a composition comprising a physiologically acceptable carrier and a therapeutically effective amount of one or more isolated antibodies, or antigen-binding fragments thereof, as described herein, thereby treating the disease associated with FZD10 expression. In one embodiment, there is provided a method for treating or preventing metastasis of a cancer associated with FZD10 expression, comprising administering, to a patient having the cancer, a composition comprising a physiologically acceptable carrier and a therapeutically effective amount of one or more of the herein described isolated anti-FZD10 antibodies, or antigen-binding fragments thereof, thereby treating or preventing metastasis of the cancer associated with FZD10 expression. Illustrative cancers in this regard include synovial sarcoma, colorectal carcinoma, and gastric carcinoma.

Another embodiment provides a method of inhibiting the proliferation or survival of a cancer cell, wherein the cancer cell overexpresses a FZD10 protein in a Wnt/Fzd signaling pathway when compared to non-cancer cells, said method comprising contacting the cancer cells with the composition comprising a physiologically acceptable carrier and a therapeutically effective amount of one or more isolated antibodies, or antigen-binding fragments thereof, as described herein. In another embodiment, there is provided a method of inhibiting canonical Wnt pathway signaling in a cell expressing a FZD10 protein, comprising contacting the cell with an anti-FZD10 antibody, or antigen-binding fragment thereof, as described herein.

According to certain embodiments of the invention described herein, there is provided a method for altering (e.g., increasing or decreasing in a statistically significant manner, including in some embodiments inhibiting) at least one of (i) survival, (ii) replication, (iii) differentiation and (iv) epithelial-to-mesenchymal cell transition of an FZD10-overexpressing cell, comprising contacting the cell with an anti-FZD10 antibody under conditions and for a time sufficient for specific binding of the antibody to the cell, wherein the anti-FZD10 antibody is selected from: (1) an isolated antibody, or an antigen-binding fragment thereof, that binds to human FZD10, comprising a heavy chain variable domain comprising the VHCDR1, VHCDR2 and VHCDR3 amino acid sequences set forth in SEQ ID NOs:5, 6 and 7, respectively, and a light chain variable domain comprising the VLCDR1, VLCDR2 and VLCDR3 amino acid sequences set forth in: SEQ ID NOs:9, 11, 12, respectively, or SEQ ID NOs:10, 11, 12, respectively; (2) an isolated antibody, or an antigen-binding fragment thereof, that binds to human FZD10, comprising a heavy chain variable domain comprising the amino acid sequence set forth in SEQ ID NO:1; (3) an isolated antibody, or an antigen-binding fragment thereof, that binds to human FZD10, comprising a light chain variable domain comprising any one of the amino acid sequences set forth in SEQ ID NOs:2, 3, and 4; and (4) an isolated antibody that competes with the antibody of (1), (2) or (3) for binding to FZD10.

In certain other embodiments there is provided a method for inhibiting tumor propagation by an FZD10-overexpressing cell, comprising contacting an isolated FZD10-overexpressing tumor cell with an anti-FZD10 antibody under conditions and for a time sufficient for specific binding of the antibody to the cell, wherein said step of contacting takes place before, during or after transplantation of the tumor cell to an adoptive test host, wherein a level of tumor tissue that is established in the adoptive test host is decreased relative to the level of tumor tissue that is established in an adoptive control host into which the FZD10-overexpressing tumor cell is transplanted without being contacted with the anti-FZD10 antibody, and wherein the anti-FZD10 antibody is selected from: (1) an isolated antibody, or an antigen-binding fragment thereof, that binds to human FZD10, comprising a heavy chain variable domain comprising the VHCDR1, VHCDR2 and VHCDR3 amino acid sequences set forth in SEQ ID NOs:5, 6 and 7, respectively, and a light chain variable domain comprising the VLCDR1, VLCDR2 and VLCDR3 amino acid sequences set forth in: SEQ ID NOs:9, 11 and 12, respectively, or SEQ ID NOs:10, 11 and 12, respectively; (2) an isolated antibody, or an antigen-binding fragment thereof, that binds to human FZD10, comprising a heavy chain variable domain comprising the amino acid sequence set forth in SEQ ID NO:1; (3) an isolated antibody, or an antigen-binding fragment thereof, that binds to human FZD10, comprising a light chain variable domain comprising any one of the amino acid sequences set forth in SEQ ID NOs:2, 3, and 4; and (4) an isolated antibody that competes with the antibody of (1), (2) or (3) for binding to FZD10.

In certain further embodiments of the above described methods, the FZD10-overexpressing cell is substantially resistant to an antiproliferative agent. In certain embodiments the method comprises contacting the cell with at least a first agent and a second agent, wherein each of said first and second agents, respectively, substantially impairs a specific interaction between at least one Wnt ligand and a first and second receptor for the Wnt ligand, wherein said first agent comprises the anti-FZD10 antibody and said first receptor comprises FZD10. In a further embodiment, the second agent comprises one or a plurality of agents that substantially impairs a specific interaction between one or more of (i) a Wnt ligand that is selected from Dkk-1, Dkk-2, Dkk-4, sFRP-1, sFRP-2, sFRP-3, sFRP4, sFRP-5, WIF-1; Norrin; R-spondin; and DkkL1 and (ii) one or more of a second receptor for the Wnt ligand that is selected from FZD1, FZD2, FZD3, FZD4, FZD5, FZD6, FZD7, FZD8, FZD9, LRP5, LRP6, ROR1, ROR2, RYK, MuSK, and a glypican.

In certain other further embodiments of the above described methods the anti-FZD10 antibody of (1) is selected from: (a) the isolated antibody or an antigen-binding fragment thereof of (1), wherein the heavy chain variable domain comprises the VHCDR1, VHCDR2 and VHCDR3 amino acid sequences set forth in SEQ ID NOs:5, 6, and 7, respectively, and the light chain variable domain comprises the VLCDR1, VLCDR2 and VLCDR3 amino acid sequences set forth in SEQ ID NOs:9, 11, and 12, respectively, (b) the isolated antibody, or an antigen-binding fragment thereof, of (a), wherein the light chain variable domain comprises the amino acid sequence set forth in SEQ ID NO:3, (c) the isolated antibody, or an antigen-binding fragment thereof, of (a), wherein the heavy chain variable domain comprises the amino acid sequence set forth in SEQ ID NO:1, (d) the isolated antibody, or an antigen-binding fragment thereof, of (1), wherein the heavy chain variable domain comprises the VHCDR1, VHCDR2 and VHCDR3 amino acid sequences set forth in SEQ ID NOs:5, 6, and 7, respectively, and the light chain variable domain comprises the VLCDR1, VLCDR2 and VLCDR3 amino acid sequences set forth in SEQ ID NOs:10, 11, and 12, respectively, (e) the isolated antibody, or an antigen-binding fragment thereof, of (d), wherein the heavy chain variable domain comprises the amino acid sequence set forth in SEQ ID NO: 1, (f) the isolated antibody, or an antigen-binding fragment thereof, of (d), wherein the light chain variable domain comprises the amino acid sequence set forth in SEQ ID NO:4, (g) the isolated antibody, or an antigen-binding fragment thereof, of (1) wherein the antibody is humanized, (h) the isolated antibody, or an antigen-binding fragment thereof, of (1) or (g) wherein the antibody is selected from a single chain antibody, a ScFv, a univalent antibody lacking a hinge region, and a minibody, (i) the isolated antibody, or an antigen-binding fragment thereof, of (1) wherein the antibody is a Fab or a Fab' fragment, (j) the isolated antibody, or an antigen-binding fragment thereof, of (1) wherein the antibody is a F(ab')$_2$ fragment, (k) the isolated antibody, or an antigen-binding fragment thereof, of (1) wherein the antibody is a whole antibody, (l) the isolated antibody, or an antigen-binding fragment thereof, of (1) wherein the antibody is conjugated to a drug or a toxin, (m) the isolated antibody, or an antigen-binding fragment thereof, of (l) wherein the toxin is saporin, (n) the isolated antibody, or an antigen-binding fragment thereof, of (1) comprising a human IgG Fc domain, and (o) the isolated antibody, or an antigen-binding fragment thereof, of (n) wherein the human IgG Fc domain is modified to obtain a modified antibody that has enhanced ADCC activity as compared to the antibody in which the human IgG Fc domain has not been modified.

In certain other further embodiments of the above described methods, the anti-FZD10 antibody of (2) is selected from (a) the isolated antibody of (2) wherein the heavy chain variable domain comprises the amino acid sequence set forth in SEQ ID NO:1 and further comprising a light chain variable domain comprising an amino acid sequence having at least 95% identity to the amino acid sequence set forth in SEQ ID NO:3, (b) the isolated antibody of (a) wherein the light chain variable domain comprises the amino acid sequence set forth in SEQ ID NO:3, (c) the isolated antibody of (2), further comprising a light chain variable domain comprising an amino acid sequence having at least 95% identity to the amino acid sequence set forth in SEQ ID NO:4, (d) the isolated antibody of (c) wherein the light chain variable domain comprises the amino acid sequence set forth in SEQ ID NO:4, (e) the isolated antibody of (2) wherein the heavy chain variable domain comprises the amino acid sequence set forth in SEQ ID NO:1 and further comprising a light chain variable domain comprising an amino acid sequence having at least 95% identity to the amino acid sequence set forth in SEQ ID NO:2, (f) the isolated antibody of (e) wherein the light chain variable domain comprises the amino acid sequence set forth in SEQ ID NO:2, (g) the isolated antibody of (2) wherein the antibody is selected from a single chain antibody, a ScFv, a univalent antibody lacking a hinge region and a minibody, (h) the isolated antibody of (2) wherein the antibody is a Fab or Fab' fragment, (i) the isolated antibody of (2) wherein the antibody is a F(ab')$_2$ fragment, (j) the isolated antibody of (2) wherein the antibody is a whole antibody, (k) the isolated antibody of (2) wherein the antibody is conjugated to a drug or a toxin, (l) the isolated antibody of (k) wherein the toxin is saporin, (m) the isolated antibody of (2) comprising a human IgG Fc domain, and (n) the isolated antibody of (m) wherein the human IgG Fc domain is modified to obtain a modified antibody that has enhanced ADCC activity as compared to the antibody in which the human IgG Fc domain has not been modified.

In certain other further embodiments of the above described methods, the anti-FZD10 antibody of (3) is selected from: (a) the isolated antibody of (3) wherein the light chain variable domain comprises SEQ ID NO:2 and further comprising a heavy chain variable domain comprising an amino acid sequence having at least 95% identity to the amino acid sequence of SEQ ID NO:1, (b) the isolated antibody of (3) wherein the light chain variable domain comprises SEQ ID NO:3 and further comprising a heavy chain variable domain comprising an amino acid sequence having at least 95% identity to the amino acid sequence of SEQ ID NO:1, (c) the isolated antibody of (3) wherein the light chain variable domain comprises SEQ ID NO:4 and further comprising a heavy chain variable domain comprising an amino acid sequence having at least 95% identity to the amino acid sequence of SEQ ID NO:1, (d) the isolated antibody of (3) wherein the antibody is selected from of a single chain antibody, a ScFv, a univalent antibody lacking a hinge region and a minibody, (e) the isolated antibody of (3) wherein the antibody is a Fab or Fab' fragment, (f) the isolated antibody of (3) wherein the antibody is a F(ab')$_2$ fragment, (g) the isolated antibody of (3) wherein the antibody is a whole antibody, (h) the isolated antibody of (3) wherein the antibody is conjugated to a drug or a toxin, (i) the isolated antibody of (h) wherein the toxin is saporin, (j) the isolated antibody of (3) comprising a human IgG Fc domain, and (k) the isolated antibody of (j) wherein the human IgG Fc domain is modified to obtain a modified antibody that has enhanced ADCC activity as compared to the antibody in which the human IgG Fc domain has not been modified.

In certain further embodiments of the above-described methods the antiproliferative agent is selected from a chemotherapeutic agent and a source of ionizing radiation. In certain other further embodiments of the above-described methods the FZD10-overexpressing cell is selected from a colon cancer cell, a breast cancer cell, a skin cancer cell, and a hematopoietic cancer cell. In certain other further embodiments of the above-described methods the FZD10-overexpressing cell is a cancer stem cell. In certain further embodiments the cancer stem cell (CSC) is selected from an acute myeloid leukemia CSC, a breast CSC, a medulloblastoma CSC, a glioblastoma CSC, a head-and-neck squamous cell carcinoma CSC, a colon CSC, a melanoma CSC, a prostate CSC, a pancreatic CSC, a non-small cell lung CSC, a hepatocellular CSC, a B-cell lymphoblastic leukemia CSC, a T-cell lymphoblastic leukemia CSC and a myeloma CSC. In certain further embodiments of the above-described methods, the method comprises altering or inhibiting at least one of (i) growth of one or more of cancer, neural, mesenchymal, and hematopoietic tissues, and (ii) development of one or more of cancer, neural, mesenchymal, and hematopoietic tissues.

In certain other further embodiments of the above-described methods the FZD10-overexpressing cell is selected from a hepatocellular carcinoma cell, a teratocarcinoma cell, a breast cancer cell, a non-small cell lung cancer cell, a malignant melanoma cell, a Wilms' tumor cell, a synovial carcinoma cell, a colorectal carcinoma cell, a colon adenocarcinoma cell, and a gastric adenocarcinoma cell.

These and other aspects and embodiments of the herein described invention will be evident upon reference to the following detailed description and attached drawings. All of the U.S. patents, U.S. patent application publications, U.S. patent applications, foreign patents, foreign patent applications and non-patent publications referred to in this specification and/or listed in the Application Data Sheet are incorporated herein by reference in their entirety, as if each was incorporated individually. Aspects and embodiments of the invention can be modified, if necessary, to employ concepts of the various patents, applications and publications to provide yet further embodiments.

BRIEF DESCRIPTION OF THE DRAWINGS

FIG. 4 is an alignment of the heavy and light chain variable region amino acid sequences of the parent B9A5 anti-FZD10 antibody and two progeny clones, B9L32.2 and B9L9.3, against the parent DTLacO germline sequence. All three antibodies share a common heavy chain VDJ, designated B9, but each has a distinct light chain VJ, designated A5, L9.3, and L32.2. Complementarity determining regions (CDRs) are underlined. The heavy chain variable region amino acid sequences are as follows: DTLacO=SEQ ID NO:13; B9=SEQ ID NO:1. The light chain variable region amino acid sequences are as follows: DTLacO=SEQ ID NO:17; A5=SEQ ID NO: 2; L9.3=SEQ ID NO:3; and L32.2=SEQ ID NO:4.

FIG. 7A shows the experimental strategy using a TOP/FOPflash luciferase reporter system to test the effects of anti-FZD10 antibodies on the canonical Wnt signaling pathway. FIG. 7B shows the results of the experiment demonstrating that the B9L9.3 antibody effectively inhibited the canonical Wnt signaling pathway.

FIG. 8 shows alignment of the humanized B9L9.3 heavy and light chain variable region amino acid sequences (SEQ ID NOs: 39 and 37, respectively) with the corresponding chicken precursor sequences (SEQ ID NOs: 1 and 3) and the human Vλ and VH subgroup III consensus sequences (SEQ ID NOs: 38 and 40). Sequence numbering is according to Kabat (1991). CDRs are underlined. Asterisks indicate a gap in the alignment. Vernier zone positions in which the chicken residue was retained in the framework sequence are denoted by a double underline. hB9L9.3H and hB9L9.3L indicate humanized versions of B9L9.3 VH and VL, respectively. HIII: human VH subgroup III consensus sequence. LIII: human Vλ subgroup III consensus sequence.

BRIEF DESCRIPTION OF THE SEQUENCES

Figure 1:
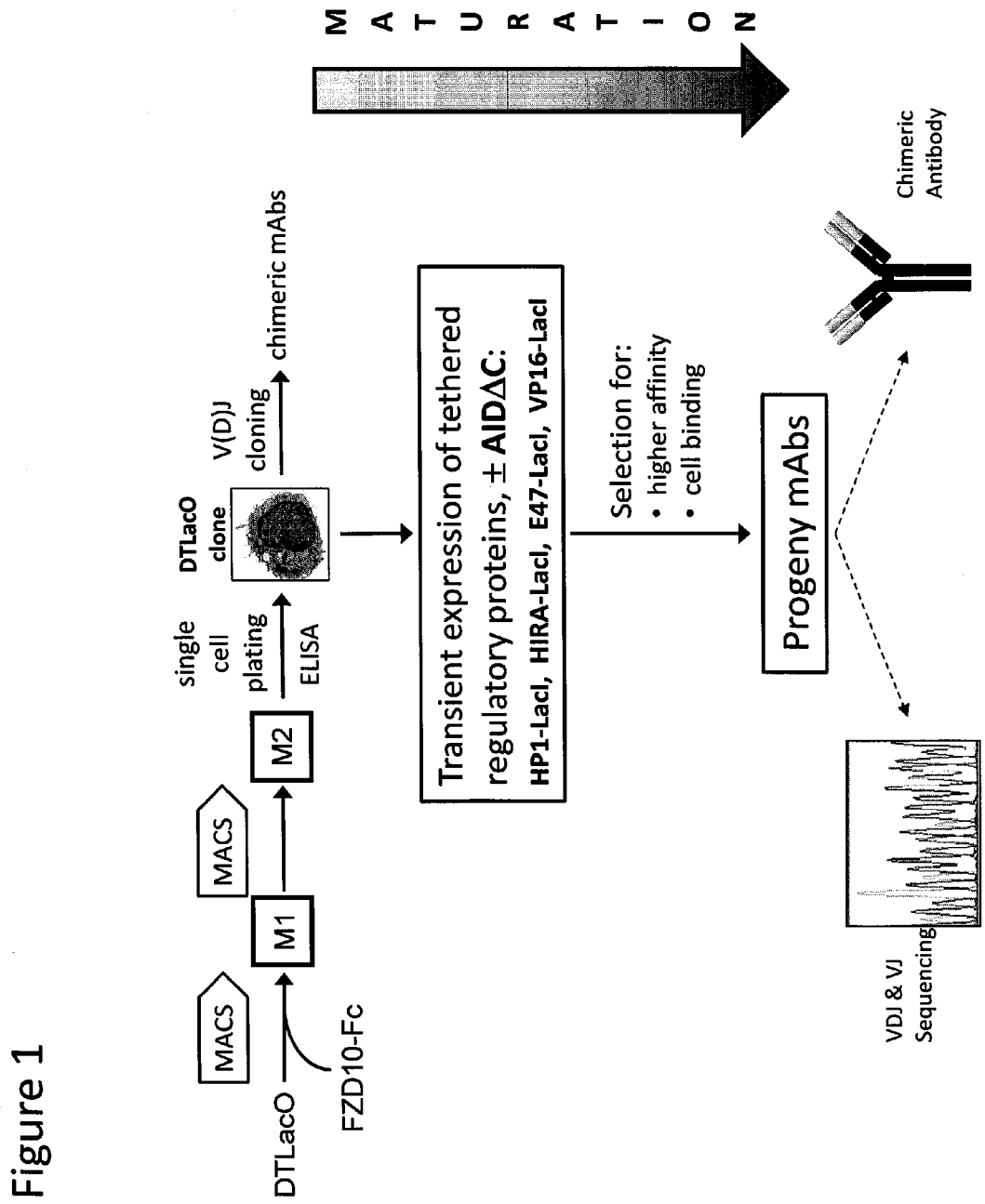
FIG. 1 is a schematic drawing of the FZD10 antibody selection and maturation process using DTLacO cells.

SEQ ID NO:1 is the amino acid sequence of the B9 heavy chain variable region of the B9A5 (parent), B9L9.3 and B9L32.2 (progeny), anti-FZD10 antibodies.

SEQ ID NO:2 is the amino acid sequence of the A5 light chain variable region of the B9A5 (parent) anti-FZD10 antibody.

SEQ ID NO:3 is the amino acid sequence of the L9.3 light chain variable region of the B9L9.3 anti-FZD10 antibody.

SEQ ID NO:4 is the amino acid sequence of the L32.2 light chain variable region of the B9L32.2 anti-FZD10 antibody.

SEQ ID NO:5 is the amino acid sequence of the B9 VHCDR1 of the B9A5 (parent), B9L9.3 and B9L32.2 (progeny), anti-FZD10 antibodies.

SEQ ID NO:6 is the amino acid sequence of the B9 VHCDR2 of the B9A5 (parent), B9L9.3 and B9L32.2 (progeny), anti-FZD10 antibodies.

SEQ ID NO:7 is the amino acid sequence of the B9 VHCDR3 of the B9A5 (parent), B9L9.3 and B9L32.2 (progeny), anti-FZD10 antibodies.

SEQ ID NO:8 is the amino acid sequence of the A5 VLCDR1 of the B9A5 parent anti-FZD10 antibody and also of the parent DTLacO VLCDR1.

SEQ ID NO:9 is the amino acid sequence of the L9.3 VLCDR1 of the B9L9.3 anti-FZD10 antibody.

SEQ ID NO:10 is the amino acid sequence of the L32.2 VLCDR1 of the B9L32.2 anti-FZD10 antibody.

SEQ ID NO:11 is the amino acid sequence of the A5, L9.3, and L32.2 VLCDR2 of the B9A5 (parent), B9L9.3 and B9L32.2 (progeny), anti-FZD10 antibodies.

SEQ ID NO:12 is the amino acid sequence of the A5, L9.3, and L32.2 VLCDR3 of the B9A5 (parent), B9L9.3 and B9L32.2 (progeny), anti-FZD10 antibodies and also for the parent DTLacO VLCDR3.

SEQ ID NO:13 is the amino acid sequence of the Parental DTLacO heavy chain variable region.

SEQ ID NO:14 is the amino acid sequence of the VHCDR1 of the parental DTLacO.

SEQ ID NO:15 is the amino acid sequence of the VHCDR2 of the parental DTLacO.

SEQ ID NO:16 is the amino acid sequence of the VHCDR3 of the parental DTLacO.

SEQ ID NO:17 is the amino acid sequence of the light chain variable region of the parental DTLacO.

SEQ ID NO:18 is the amino acid sequence of the VLCDR2 of the parental DTLacO.

SEQ ID NO:19 is the polynucleotide encoding the amino acid sequence of SEQ ID NO:1, encoding the B9 heavy chain variable region for the B9A5 (parent), B9L9.3 and B9L32.2 (progeny), anti-FZD10 antibodies.

SEQ ID NO:20 is the polynucleotide encoding the amino acid sequence of SEQ ID NO:2 (A5 light chain variable region for the B9A5 antibody).

SEQ ID NO:21 is the polynucleotide encoding the amino acid sequence of SEQ ID NO: 3 (L9.3 light chain variable region for the B9L9.3 antibody).

SEQ ID NO:22 is the polynucleotide encoding the amino acid sequence of SEQ ID NO:4 (L32.2 light chain variable region for the B9L32.2 antibody).

SEQ ID NO:23 is the polynucleotide encoding the amino acid sequence of the parent DTLacO heavy chain variable region.

SEQ ID NO:24 is the polynucleotide encoding the amino acid sequence of the parent DTLacO light chain variable region.

SEQ ID NOs 25, 26 and 27 are amino acid sequences of linkers.

SEQ ID NO:28 shows a human FZD10 amino acid sequence.

SEQ ID NO:29 is the amino acid sequence of humanized L9.3 light chain, including the human Ig lambda constant region.

SEQ ID NO:30 is the polynucleotide encoding the amino acid sequence of humanized L9.3 light chain (including signal sequence).

SEQ ID NO:31 is the amino acid sequence of humanized B9 heavy chain, including the human IgG1 constant region.

SEQ ID NO:32 is the polynucleotide encoding the amino acid sequence of humanized B9 heavy chain (including signal sequence).

SEQ ID NO:33: is the polynucleotide encoding the amino acid sequence of human IgG1 constant region (CH1-hinge-CH2-CH3).

SEQ ID NO:34: is the amino acid sequence for human IgG1 constant region (CH1-hinge-CH2-CH3).

SEQ ID NO:35: is the polynucleotide encoding the amino acid sequence of human lambda light chain constant region.

SEQ ID NO:36: is the amino acid sequence of human lambda light chain constant region.

SEQ ID NO:37: is the amino acid sequence of humanized L9.3 light chain VJ region.

SEQ ID NO:38: is the amino acid sequence of human Vλ subgroup III consensus sequence with CDRs denoted with "X".

SEQ ID NO:39: is the amino acid sequence of humanized B9 heavy chain VDJ region.

SEQ ID NO:40: is the amino acid sequence of human VH subgroup III consensus sequence with CDRs denoted with "X".

DETAILED DESCRIPTION

Embodiments of the present invention relate to antibodies that bind to FZD10, a Wnt family receptor protein (e.g., SEQ ID NO:28). In particular, the antibodies described herein specifically bind to FZD10 with unexpectedly high affinity and will in certain embodiments have therapeutic utility for the treatment of diseases associated with FZD10 expression, such as diseases associated with aberrant or altered FZD10 expression, and in particular FZD10 overexpression (e.g., detectable FZD10 expression at a level that is greater in magnitude than the level of expression that is detectable in and/or on a normal or disease-free cell). Such diseases include various forms of cancer and include, without limitation, synovial sarcoma, colorectal carcinoma, gastric carcinoma, chronic myeloid leukemia (CML) and acute myeloid leukemia (AML), and other cancers. Amino acid sequences of illustrative antibodies, or antigen-binding fragments thereof, or complementarity determining regions (CDRs) thereof, are set forth in SEQ ID NOs:1-12, encoded by the polynucleotide sequences set forth in SEQ ID NOs:19-22.

Certain embodiments of the present invention relate to methods of using antibodies that bind to FZD10, a Wnt family receptor protein (e.g., SEQ ID NO:28), to alter (e.g., increase or decrease in a statistically significant manner, including in some embodiments to inhibit) survival, replication, differentiation, or dedifferentiation (e.g., epithelial-to-mesenchymal cell transition) of FZD10-overexpressing cells or of FZD10$^+$ stem cells such as embryonic stem cells or their progeny, and/or to inhibit tumor propagation by FZD10-overexpressing cells. The methods described herein are useful for the treatment of diseases associated with expression (typically overexpression) of FZD10, such as a variety of cancers, and for the identification of treatment regimens that comprise administration of anti-FZD10 antibodies alone or in combination with other agents. Also described herein are methods in which the present anti-FZD10 antibodies may beneficially influence development of FZD10$^+$ stem cells such as embryonic stem cells or their progeny, for example, by introducing such cells in vivo before or after anti-FZD10 antibody induction to develop into cardiomyocytes to effect repair of infarction-damaged myocardium, or to develop into endothelial cells and/or smooth muscle cells to effect vascular repair in cardiovascular disease or cancer or other relevant conditions. Amino acid sequences of illustrative anti-FZD10 antibodies, or antigen-binding fragments thereof, or complementarity determining regions (CDRs) thereof, are set forth in SEQ ID NOs:1-12, and are encoded by the polynucleotide sequences set forth in SEQ ID NOs:20-23.

In certain embodiments and according to non-limiting theory, the herein described anti-FZD10 antibodies may be contacted with cancer stem cells (CSCs) alone or in combination with other agents, to inhibit tumor propagation. Further according to non-limiting theory, a cancer stem cell may be a cell of a solid tumor or of a hematopoietic cancer that is characterized by the ability to initiate formation of a new tumor, and by the ability to transfer cancer to an adoptive host. (Park et al., 2009 Molec. Therap. 17:219). For example, the cell surface marker phenotype of human CSCs from a particular type of donor tumor may be determined by transplanting xenografts of candidate CSCs that have been isolated on the basis of cell surface marker expression to immunodeficient mice, and determining whether establishment and growth of a recipient tumor of the same type as the donor tumor take place. Id. An "isolated" cell is one that has been removed from the natural environment in which it originally occurred, or progeny of such a cell that have been maintained, propagated or generated in vitro.

The ability of isolated tumor cells to initiate new tumors, and to do so via serial transplantation in vivo, has been demonstrated for a large variety of model systems. See, e.g., Park et al., 2009 Molec. Therap. 17:219; Curtin et al., 2010 Oncotarget 1:563; De Almeida et al., 2007 Canc. Res. 67:5371; Ettenberg et al., 2010 Proc. Nat. Acad. Sci. USA 107:15473; Fukukawa et al., 2009 Oncogene 28:1110; Fukukawa et al., 2008 Canc. Sci. 99:432; He et al., 2004 Neoplasia 6:7; Hu et al., 2009 Canc. Res. 69:6951; Nagayama et al., 2009 Canc. Sci. 100:405; Hagayama et al., 2005 Oncogene 24:6201; Nagayama et al., 2002 Canc. Res. 62:5859; Pode et al., 2011 Oncogene 30:1664; You et al., 2004 Canc. Res. 64:56385; and the like.

In these and related systems, transplanted tumor cells (including tumor fragments comprising a plurality of tumor cells) may be regarded as establishing a tumor in the adoptive host (e.g., a recipient multicellular organism, preferably a vertebrate and more preferably a mammal, such as a mouse, rat, rabbit, guinea pig, dog, cat, goat, sheep, etc.) when the transplanted cells are observed to replicate to produce a tumor in which measurable growth can be detected in a statistically significant manner. Typically, the tumor in the adoptive host will phenotypically resemble the tumor from which the adoptively transferred cells were obtained. Established solid tumors may often exhibit characteristic phenotypes such as cell surface marker expression, cytoskeletal component expression and organization, morphology, presence of a vascular network and/or basement membrane, and other features.

Accordingly, in certain embodiments the present invention provides a method for inhibiting tumor propagation by an FZD10-overexpressing cell, comprising contacting an isolated FZD10-overexpressing tumor cell with an anti-FZD10 antibody as described herein, under conditions and for a time sufficient for specific binding of the antibody to the cell, wherein the step of contacting takes place before, during or after transplantation of the tumor cell to an adoptive test host (e.g., the host organism that also receives the anti-FZD10 antibody), wherein a level of tumor tissue that is established in the adoptive test host is decreased relative to the level of tumor tissue that is established in an adoptive control host into which the FZD10-overexpressing tumor cell is transplanted without being contacted with the anti-FZD10 antibody.

There are thus expressly contemplated, according to certain of the herein described embodiments, methods by which these and/or related systems may be used to determine the inhibition by an anti-FZD10 antibody of tumor propagation by an FZD10-overexpressing cell, or to determine inhibition by an anti-FZD10 antibody of survival, replication, differentiation and/or dedifferentiation (e.g., epithelial-to-mesenchymal cell transition) of an FZD10-overexpressing cell.

The herein described anti-FZD10 antibody may be used alone as a first agent that substantially impairs a specific interaction between a first Wnt ligand (e.g., WNT7a and/or WNT7b) and a first receptor for the Wnt ligand (e.g., FZD10). Additionally or alternatively, the herein described anti-FZD10 antibody may be used in combination with one or more additional agents. In certain such embodiments the additional agent(s) may comprise a second agent that substantially impairs a specific interaction between at least one second Wnt ligand (e.g., a DKK family member such as Dkk-1, Dkk-2 or Dkk-4; a secreted Frizzled-related protein (sFRP) such as sFRP-1, sFRP-2, sFRP-3, sFRP4 or sFRP-5; Wnt Inhibitory Factor 1 (WIF-1); Norrin; R-spondin; DkkL1; etc.) and a second receptor for the Wnt ligand (e.g., FZD1, FZD2, FZD3, FZD4, FZD5, FZD6, FZD7, FZD8, FZD9, LRP5, LRP6, ROR1, ROR2, RYK, MuSK, and a glypican such as glypican3; see, e.g., Schulte 2010 *Pharmacol. Rev.* 62:632; Rao and Kühl, 2010 *Circ. Res.* 106:1798; Filmus et al., 2008 *Genome Biol.* 9:224; Chien and Moon, 2007 *Front. Biosci.* 12:448; see also Table 1.). Non-limiting examples of such a second agent that substantially impairs (e.g., inhibits in a statistically significant manner by at least about 50, 55, 60, 65, 70, 75, 80, 85, 90, 95 percent or more) a specific interaction between such a second Wnt ligand and such a second receptor for the Wnt ligand are presented in Table 1, where gene knockout models will be understood to identify targets for suppression of relevant gene expression, for example, using established siRNA technology (e.g., Wang et al., 2011 *Mini Rev. Med. Chem.* 11:114; Petrocca et al., 2011 *J. Clin. Oncol.* 29:747; Shi et al., 2011 *Expert Opin. Biol. Ther.* 11:5; Nijwening et al., 2010 *IDrugs* 13:772).

TABLE 1

"SECOND" WNT LIGANDS, "SECOND" RECEPTORS FOR "SECOND" WNT LIGANDS, AND "SECOND" AGENTS THAT IMPAIR INTERACTIONS THEREBETWEEN

| Wnt Ligand | Inhibitory Agent | Reference |
| --- | --- | --- |
| Dkk-1 | Dkk1-specific antibodies | Yaccoby et al., 2007 *Blood* 109: 2106 |
|  | Dkk1-specific antibody | Glantschnig et al., 2010 *J. Biol. Chem.* 285: 40135 |
| Dkk-2 | Dkk2-specific antibody | Olivares-Navarrete et al., 2010 *Biomat.* 31: 2015 |
| Dkk-4 | Dkk4-specific siRNA | Maehata et al., 2008 *World J. Gastroenterol.* 14: 2702 |
| sFRP-1 | WAY-316606 (trifluoromethyl analog) | Bodine et al., 2009 *Bone* 44: 1063 |
|  | sFRP1-specific antibody and siRNA | Haüsler et al., 2004 *J. Bone Miner. Res.* 19: 1873 |
| sFRP-2 | sFRP2-specific siRNA | Deb et al., 2008 *Stem Cells* 26: 35 |
| sFRP-3 | sFRP3-specific siRNA | Hirata et al., 2010 *Cancer Res.* 70: 1896 |
| sFRP-4 | sFRP4-specific siRNA | Park et al., 2008 *Cell Prolif.* 41: 859 |
| sFRP-5 | sFRP5 knockout in mice | Satoh et al., 2008 *Genesis* 46: 92 |
| WIF-1 | WIF1-specific antiserum | Hunter et al., 2004 *Mol. Cell Neurosci.* 27: 477 |
|  | WIF1-specific siRNA | Wu et al., 2011 *Toxicol.* 285: 97 |
| Norrin | norrin knockout in mice | Rehm et al., 2002 *J. Neurosci.* 22: 4286 |
|  |  | Luhmann et al., 2005 *Genesis* 42: 253 |
| R-spondin | R-spondin2 knockout in mice | Aoki et al., 2008 *Dev. Growth Differ.* 50: 85 |
|  | R-spondin1 knockout in mice | Chadi et al., 2009 *Biochem. Biophys. Res. Comm.* 390: 1040 |
| DkkL1 | DKKL1 knockout in mice | Dakhova et al., 2009 *Endocrinol.* 150: 404 |
| FZD1 | FZD1-specific shRNA | Flahaut et al., 2009 *Oncogene* 28: 2245 |
| FZD2 | FZD2-specific siRNA | Ortega-Paino et al., 2008 *Blood* 111: 1617 |
| FZD3 | FZD3-specific siRNA and antiserum | Endo et al., 2008 *Mol. Cell. Biol.* 28: 2368 |
|  | FZD3 knockout in mice | Stuebner et al., 2010 *Dev. Dynamics* 239: 246 |

TABLE 1-continued

"SECOND" WNT LIGANDS, "SECOND"
RECEPTORS FOR "SECOND" WNT LIGANDS,
AND "SECOND" AGENTS THAT IMPAIR INTERACTIONS THEREBETWEEN

| Wnt Ligand | Inhibitory Agent | Reference |
|---|---|---|
| FZD4 | FZD4-specific antibody | Paes et al., 2011 Invest. Ophthalmal. Vis. Sci. 52: 6452 |
| | FZD4 knockout in mice | Ye et al., 2011 Development 138, 1161 |
| | Tsukushi (TSKU) | Ohta et al., 2011 Proc. Nat. Acad. Sci. 108: 14962 |
| FZD5 | FZD5-specific antiserum | Sen et al., 2001 Arthritis Rheum. 44: 772 |
| | FZD5-specific siRNA | Snow et al., 2009 BMC Cancer 9: 383 |
| | FZD5 knockout in mice | Zhang et al., 2008 Invest. Ophthalmol. Vis. Sci. 49: 5561 |
| FZD6 | FZD6 knockout in mice | Guo et al., 2004 Proc. Nat. Acad. Sci. 101: 9277 |
| | | Stuebner et al., 2010 Dev. Dynamics 239: 246 |
| FZD7 | FZD7-specific antibody | Pode-Shakked et al., 2011 Oncogene 30: 1664 |
| | FZD7-specific siRNA | Snow et al., 2009 BMC Cancer 9: 383 |
| FZD8 | FZD8-specific siRNA | Yoshida et al., 2007 Am. J. Physiol. Gastrointest. Liver Physiol. 293: G1089 |
| | FZD8 knockout in mice | Ye et al., 2011 Development 138, 1161 |
| FZD9 | FZD9-specific siRNA | Fujimoto et al., 2009 Int. J. Oncol. 35: 861 |
| | FZD9 knockout in mice | Ranheim et al., 2005 Blood 105: 2487 |
| LRP5 | LRP5-specific antiserum | Björklund et al., 2009 PLoS ONE 4(1): e4243 |
| | LRP5-specific siRNA | Papathanasiou et al., 2010 J. Orthop. Res. 28: 348 |
| LRP6 | LRP6-specific antibody | Gong et al., 2010 PLoS ONE 5: e12682 |
| | LRP6-specific antibodies | Ettenberg et al., 2010. Proc. Nat. Acad. Sci. 107: 15473 |
| | SERPINA3K | Zhang et al., 2010 Proc. Nat. Acad. Sci. 107: 6900 |
| | pigment epithelium-derived factor (PEDF) | Park et al., 2011 Mol. Cell. Biol. 31: 3038 |
| ROR1 | ROR1-specific antibodies | Yang et al., 2011 PLoS ONE 6: e21018 |
| | ROR1-specific antibodies | Fukuda et al., 2008 Proc. Nat. Acad. Sci. 105: 3047 |
| | ROR1-specific siRNA | Choudhury et al., 2010 Br. J. Haematol. 151: 327 |
| ROR2 | ROR2-specific antiserum | Liu et al., 2007 Mol. Endocrinol. 21: 3050 |
| | ROR2-specific siRNA | O'Connell et al., 2010 Oncogene 29: 34 |
| RYK | RYK-specific antibody | Miyashita et al., 2009 J. Neurotrauma 26: 955 |
| | RYK-specific antiserum | Liu et al., 2008 J. Neurosci. 28: 8376 |
| | RYK-specific siRNA | Lu et al., 2004 Cell 119: 97 |
| MuSK | MuSK-specific antibodies | Jha et al., 2006 J. Neuroimmunol. 175: 107 |
| | MuSK knockout in mice | Banerjee et al., 2011 Development 138: 3287 |
| glypican | Glypican3-specific siRNA | Akutsu et al., 2010 World J. Gastroenterol. 16: 3521 |

Certain embodiments as presently disclosed thus contemplate a method for altering (e.g., increasing or decreasing in a statistically significant manner and in some embodiments inhibiting) at least one of survival, replication, differentiation and epithelial-to-mesenchymal cell transition of an FZD10-overexpressing cell, comprising contacting the cell with a herein-described anti-FZD10 antibody under conditions and for a time sufficient for specific binding of the antibody to the cell to take place. Criteria for determining cell survival, replication, differentiation and epithelial-to-mesenchymal cell transition are known and will be appreciated by those skilled in the art. Pathways for biological signal transduction, including those associated with cell division, cell survival, apoptosis, proliferation and differentiation, may in certain instances be referred to as "biological signal transduction pathways," or "inducible signaling pathways" and may include transient or stable associations or interactions among cellular and extracellular molecular components that are involved in the control of these and similar processes in cells. Depending on the particular pathway(s) of interest, one or more appropriate parameters for determining induction of such pathway(s) may be selected based on art-accepted criteria.

For example, for signaling pathways associated with cellular replication or proliferation, a variety of well known methodologies are available for quantifying replication or proliferation, including, for example, incorporation by proliferating cells of tritiated thymidine into cellular DNA, monitoring of detectable (e.g., fluorimetric or colorimetric) indicators of cellular respiratory activity (for example, conversion of the tetrazolium salts (yellow) 3-(4,5-dimethylthiazol-2-yl)-2,5-diphenyltetrazolium bromide (MTT) or 3-(4,5-dimethylthiazol-2-yl)-5-(3-carboxymethoxyphenyl)-2-(4-sulphophenyl)-2H-tetrazolium (MTS) to formazan dyes (purple) in metabolically active cells), or cell counting, or the like.

Similarly, in the cell biology arts, multiple techniques are known for assessing cell survival by any of a number of known methodologies including viability determination by microscopic, biochemical, spectrophotometric, spectroscopic, light-scattering, cytometric including flow cytometric and cytofluorimetric, or other techniques (e.g., vital dyes such as Trypan Blue, DNA-binding fluorophores such as propidium iodide, metabolic indicators, etc.) and for determining apoptosis (for example, annexin V binding, DNA fragmentation assays, caspase activation, marker analysis, e.g., poly (ADP-ribose) polymerase (PARP), etc.).

Other signaling pathways will be associated with particular cellular phenotypes, for example specific induction of gene expression (e.g., detectable as transcription or translation products, or by bioassays of such products, or as nuclear localization of cytoplasmic factors), altered (e.g., statistically significant increases or decreases) levels of intracellular mediators (e.g., activated kinases or phosphatases, altered levels of cyclic nucleotides or of physiologically active ionic species, altered levels of the degree of phosphorylation of one or more specific phosphorylation substrates, etc.), altered cell cycle profiles, or altered cellular morphology, and the like, such that cellular responsiveness to a particular stimulus as provided herein can be readily identified to determine whether a particular cell is undergoing or has undergone a survival, replication, differentiation or dedifferentiation event (e.g., epithelial-to-mesenchymal cell transition; see, for example, Hlubek et al., 2007 *Front. Biosci.* 12:458).

The presence of a malignant condition in a subject refers to the presence of dysplastic, cancerous and/or transformed cells in the subject, including, for example neoplastic, tumor, non-contact inhibited or oncogenically transformed cells, or the like (e.g., melanoma, carcinomas such as adenocarcinoma, squamous cell carcinoma, small cell carcinoma, oat cell carcinoma, etc., sarcomas such as chondrosarcoma, osteosarcoma, etc.) which are known to the art and for which criteria for diagnosis and classification are established (e.g., Hanahan and Weinberg, 2011 *Cell* 144:646; Hanahan and Weinberg 2000 *Cell* 100:57; Cavallo et al., 2011 *Canc. Immunol. Immunother.* 60:319; Kyrigideis et al., 2010 *J. Carcinog.* 9:3) In preferred embodiments contemplated by the present invention, for example, such cancer cells may be cells of acute myeloid leukemia, breast cancer, medulloblastoma, glioblastoma, head-and-neck squamous cell carcinoma, colon cancer, melanoma, prostate cancer, pancreatic cancer, non-small cell lung cancer, B-cell lymphoblastic leukemia, T-cell lymphoblastic leukemia, myeloma, hepatocellular carcinoma, teratocarcinoma, Wilms' tumor, synovial carcinoma, colorectal carcinoma, colon adenocarcinoma, or gastric adenocarcinoma, including cancer stem cells that are capable of initiating and serially transplanting any of these types of cancer (see, e.g., see Park et al. 2009 *Molec. Therap.* 17:219).

According to certain contemplated embodiments, anti-FZD10 mAbs as described herein may advantageously recruit desired immune effector cell function(s) in a therapeutic context, where it is well known that immune effector cells having different specialized immune functions can be distinguished from one another on the basis of their differential expression of a wide variety of cell surface antigens. Immune effector cells include any cell that is capable of directly mediating an activity which is a component of immune system function, including cells having such capability naturally or as a result of genetic engineering.

In certain embodiments an immune effector cell comprises a cell surface receptor for an immunoglobulin, such as a receptor for an immunoglobulin constant region and including the class of receptors commonly referred to as "Fc receptors" (FcR). A number of FcR have been structurally and/or functionally characterized and are well known in the art, including FcR having specific abilities to interact with a restricted subset of immunoglobulin heavy chain isotypes, or that interact with Fc domains with varying affinities, and/or which may be expressed on restricted subsets of immune effector cells under certain conditions (e.g., Kijimoto-Ochichai et al., 2002 *Cell Mol. Life Sci.* 59:648; Davis et al., 2002 *Curr. Top. Microbiol. Immunol.* 266:85; Pawankar, 2001 *Curr. Opin. Allerg. Clin. Immunol.* 1:3; Radaev et al., 2002 *Mol. Immunol.* 38:1073; Wurzburg et al., 2002 *Mol. Immunol.* 38:1063; Sulica et al., 2001 *Int. Rev. Immunol.* 20:371; Underhill et al., 2002 *Ann. Rev. Immunol.* 20:825; Coggeshall, 2002 *Curr. Dir. Autoimm.* 5:1; Mimura et al., 2001 *Adv. Exp. Med. Biol.* 495:49; Baumann et al., 2001 *Adv. Exp. Med. Biol.* 495:219; Santoso et al., 2001 *Ital. Heart J.* 2:811; Novak et al., 2001 *Curr. Opin. Immunol.* 13:721; Fossati et al., 2001 *Eur. J. Clin. Invest.* 31:821).

Cells that are capable of mediating antibody-dependent cell-mediated cytotoxicity (ADCC) are preferred examples of immune effector cells according to the present invention. Other preferred examples include natural killer (NK) cells, tumor-infiltrating T lymphocytes (TIL), cytotoxic T lymphocytes (CTL), and granulocytic cells such as cells that comprise allergic response mechanisms. Immune effector cells thus include, but are not limited to, cells of hematopoietic origin including cells at various stages of differentiation within myeloid and lymphoid lineages and which may (but need not) express one or more types of functional cell surface FcR, such as T lymphocytes, B lymphocytes, NK cells, monocytes, macrophages, dendritic cells, neutrophils, basophils, eosinophils, mast cells, platelets, erythrocytes, and precursors, progenitors (e.g., hematopoietic stem cells), quiescent, activated and mature forms of such cells. Other immune effector cells may include cells of non-hematopoietic origin that are capable of mediating immune functions, for example, endothelial cells, keratinocytes, fibroblasts, osteoclasts, epithelial cells and other cells. Immune effector cells may also include cells that mediate cytotoxic or cytostatic events, or endocytic, phagocytic, or pinocytotic events, or that effect induction of apoptosis, or that effect microbial immunity or neutralization of microbial infection, or cells that mediate allergic, inflammatory, hypersensitivity and/or autoimmune reactions.

Antibodies and Antigen-Binding Fragments Thereof

An "antibody" is an immunoglobulin molecule capable of specific binding to a target, such as a carbohydrate, polynucleotide, lipid, polypeptide, etc., through at least one epitope recognition site, located in the variable region (also referred to herein as the variable domain) of the immunoglobulin molecule. As used herein, the term "antibody" encompasses not only intact polyclonal or monoclonal antibodies, but also fragments thereof (such as a single variable region antibody (dAb), or other known antibody fragments such as Fab, Fab', F(ab')$_2$, Fv and the like, single chain (ScFv), synthetic variants thereof, naturally occurring variants, fusion proteins comprising an antibody portion with an antigen-binding fragment of the required specificity, humanized antibodies, chimeric antibodies, and any other engineered or modified configuration of the immunoglobulin molecule that comprises an antigen-binding site or fragment (epitope recognition site) of the required specificity. "Diabodies", multivalent or multispecific fragments constructed by gene fusion (WO94/13804; Holliger et al, *Proc. Natl. Acad. Sci. USA* 90 6444-6448, 1993) are also a particular form of antibody contemplated herein. Minibodies comprising a scFv joined to a CH3 domain are also included herein (Hu et al, *Cancer Res.*, 56, 3055-3061, 1996; see also e.g., Ward et al., *Nature* 341, 544-546 (1989); Bird et al, *Science* 242, 423-426, 1988; Huston et al, *PNAS USA*, 85, 5879-5883, 1988; PCT/US92/

09965; WO94/13804; Holliger et al., *Proc. Natl. Acad. Sci. USA* 90 6444-6448, 1993; Reiter et al., *Nature Biotech* 14, 1239-1245, 1996; Hu et al, *Cancer Res.* 56, 3055-3061, 1996). Nanobodies and maxibodies are also contemplated (see, e.g., U.S. Pat. Nos. 6,765,087; 6,838,254; WO 06/079372; WO 2010/037402).

The term "antigen-binding fragment" as used herein refers to a polypeptide fragment that contains at least one CDR of an immunoglobulin heavy and/or light chain that binds to the antigen of interest, which antigen in particularly preferred embodiments described herein is the FZD10 receptor. In this regard, an antigen-binding fragment of the herein described antibodies may comprise one, two, three, four, five or all six CDRs of a VH and/or VL sequence set forth herein from antibodies that bind FZD10. An antigen-binding fragment of the herein described FZD10-specific antibodies is capable of binding to FZD10. In certain embodiments, an antigen-binding fragment or an antibody comprising an antigen-binding fragment, mediates killing of a target cell expressing FZD10. In other embodiments, binding of an antigen-binding fragment prevents or inhibits binding of FZD10 ligand(s) (e.g., a Wnt protein) to the FZD10 receptor, interrupting the biological response that would otherwise result from ligand binding to the receptor. In certain embodiments, the antigen-binding fragment binds specifically to and/or inhibits or modulates the biological activity of human FZD10.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, preferably a polypeptide determinant, that is capable of specific binding to an immunoglobulin or T-cell receptor. An epitope is a region of an antigen that is bound by an antibody. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. In certain embodiments, an antibody is said to specifically bind an antigen when it preferentially recognizes its target antigen in a complex mixture of proteins and/or macromolecules. An antibody may according to certain embodiments be said to bind an antigen specifically when the equilibrium dissociation constant for antibody-antigen binding is less than or equal to $10^{-6}$ M, or less than or equal to $10^{-7}$ M, or less than or equal to $10^{-8}$ M. In some embodiments, the equilibrium dissociation constant may be less than or equal to $10^{-9}$ M or less than or equal to $10^{-10}$ M.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment which comprises both antigen-binding sites. An Fv fragment for use according to certain embodiments of the present invention can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent V$_H$::V$_L$ heterodimer including an antigen-binding site which retains much of the antigen recognition and binding capabilities of the native antibody molecule (Inbar et al. (1972) *Proc. Nat. Acad. Sci. USA* 69:2659-2662; Hochman et al. (1976) *Biochem* 15:2706-2710; and Ehrlich et al. (1980) *Biochem* 19:4091-4096).

In certain embodiments, single chain Fv or scFV antibodies are contemplated. For example, Kappa bodies (III et al., *Prot. Eng.* 10:949-57 (1997); minibodies (Martin et al., *EMBO J.* 13:5305-9 (1994); diabodies (Holliger et al., *PNAS* 90:6444-8 (1993)); or Janusins (Traunecker et al., *EMBO J.* 10:3655-59 (1991) and Traunecker et al. *Int. J. Cancer Suppl.* 7:51-52 (1992)), may be prepared using standard molecular biology techniques following the teachings of the present application with regard to selecting antibodies having the desired specificity. In still other embodiments, bispecific or chimeric antibodies may be made that encompass the ligands of the present disclosure. For example, a chimeric antibody may comprise CDRs and framework regions from different antibodies, while bispecific antibodies may be generated that bind specifically to FZD10 through one binding domain and to a second molecule through a second binding domain. These antibodies may be produced through recombinant molecular biological techniques or may be physically conjugated together.

A single chain Fv (sFv) polypeptide is a covalently linked V$_H$::V$_L$ heterodimer which is expressed from a gene fusion including V$_H$- and V$_L$-encoding genes linked by a peptide-encoding linker. Huston et al. (1988) *Proc. Nat. Acad. Sci. USA* 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

A dAb fragment of an antibody consists of a VH domain (Ward, E. S. et al., Nature 341, 544-546 (1989)).

In certain embodiments, an antibody as herein disclosed (e.g., an FZD10-specific antibody) is in the form of a diabody. Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site; antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Holliger, P. and Winter G. *Current Opinion Biotechnol.* 4, 446-449 (1993)), e.g. prepared chemically or from hybrid hybridomas, or may be any of the bispecific antibody fragments mentioned above. Diabodies and scFv can be constructed without an Fc region, using only variable regions, potentially reducing the likelihood or severity of an elicited immune response, such as an anti-idiotypic reaction, in a subject receiving an administration of such antibodies.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by knobs-into-holes engineering (Ridgeway et al, *Protein Eng.*, 9, 616-621, 1996).

In certain embodiments, the antibodies described herein may be provided in the form of a UniBody®. A UniBody® is an IgG4 antibody with the hinge region removed (see GenMab Utrecht, The Netherlands; see also, e.g., US20090226421). This proprietary antibody technology creates a stable, smaller antibody format with an anticipated longer therapeutic window than current small antibody formats. IgG4 antibodies are considered inert and thus do not interact with the immune system. Fully human IgG4 antibodies may be modified by eliminating the hinge region of the antibody to obtain half-molecule fragments having distinct stability properties relative to the corresponding intact IgG4 (GenMab, Utrecht). Halving the IgG4 molecule leaves only one area on the UniBody® that can bind to cognate antigens (e.g., disease targets) and the UniBody® therefore binds univalently to only one site on target cells. For certain cancer cell surface antigens, this univalent binding may not stimulate the cancer cells to grow as may be seen using bivalent antibodies having the same antigen specificity, and hence UniBody® technology may afford treatment options for some types of cancer that may be refractory to treatment with conventional antibodies. The UniBody® is about half the size of a regular IgG4 antibody. This small size can be a great benefit when treating some forms of cancer, allowing for better distribution of the molecule over larger solid tumors and potentially increasing efficacy.

In certain embodiments, the antibodies of the present disclosure may take the form of a nanobody. Nanobodies are encoded by single genes and are efficiently produced in almost all prokaryotic and eukaryotic hosts, e.g., *E. coli* (see e.g. U.S. Pat. No. 6,765,087), molds (for example *Aspergillus* or *Trichoderma*) and yeast (for example *Saccharomyces*, Kluyvermyces, *Hansenula* or *Pichia* (see e.g. U.S. Pat. No. 6,838,254)). The production process is scalable and multi-kilogram quantities of nanobodies have been produced. Nanobodies may be formulated as a ready-to-use solution having a long shelf life. The Nanoclone method (see, e.g., WO 06/079372) is a proprietary method for generating Nanobodies against a desired target, based on automated high-throughput selection of B-cells.

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

The structures and locations of immunoglobulin variable regions may be determined by reference to Kabat, E. A. et al, Sequences of Proteins of Immunological Interest, 4th Edition, US Department of Health and Human Services, 1987, and updates thereof, now available on the Internet (immuno.bme.nwu.edu).

A "monoclonal antibody" refers to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', $F(ab')_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals, etc.). The term includes whole immunoglobulins as well as the fragments etc. described above.

"Humanized" antibodies refer to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable regions fused onto constant domains or only the CDRs grafted onto appropriate framework regions in the variable domains. Epitope binding sites may be wild type or may be modified by one or more amino acid substitutions. This chimeric structure eliminates the constant region of non-human origin as an immunogen in human individuals, but the possibility of an immune response to the foreign variable region remains (LoBuglio, A. F. et al., (1989) *Proc Natl Acad Sci USA* 86:4220-4224; Queen et al., *PNAS* (1988) 86:10029-10033; Riechmann et al., *Nature* (1988) 332:323-327). Illustrative humanized antibodies according to certain embodiments of the present invention comprise the humanized sequences provided in SEQ ID NOs: 29, 31, 37, 39.

Another approach focuses not only on providing human-derived constant regions, but also on modifying the variable regions as well so as to reshape them as closely as possible to human form. As also noted above, it is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato, K., et al., (1993) *Cancer Res* 53:851-856; Riechmann, L., et al., (1988) *Nature* 332:323-327; Verhoeyen, M., et al., (1988) *Science* 239:1534-1536; Kettleborough, C. A., et al., (1991) *Protein Engineering* 4:773-3783; Maeda, H., et al., (1991) *Human Antibodies Hybridoma* 2:124-134; Gorman, S. D., et al., (1991) *Proc Natl Acad Sci USA* 88:4181-4185; Tempest, P. R., et al., (1991) *Bio/Technology* 9:266-271; Co, M. S., et al., (1991) *Proc Natl Acad Sci USA* 88:2869-2873; Carter, P., et al., (1992) *Proc Natl Acad Sci USA* 89:4285-4289; and Co, M. S. et al., (1992) *J Immunol* 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

In certain embodiments, the antibodies of the present disclosure may be chimeric antibodies. In this regard, a chimeric antibody is comprised of an antigen-binding fragment of an anti-FZD10 antibody operably linked or otherwise fused to a heterologous Fc portion of a different antibody. In certain embodiments, the heterologous Fc domain is of human origin. In other embodiments, the heterologous Fc domain may be from a different Ig class from the parent antibody, including IgA (including subclasses IgA1 and IgA2), IgD, IgE, IgG (including subclasses IgG1, IgG2, IgG3, and IgG4), and IgM. In further embodiments, the heterologous Fc domain may be comprised of CH2 and CH3 domains from one or more of the different Ig classes. As noted above with regard to humanized antibodies, the anti-FZD10 antigen-binding fragment of a chimeric antibody may comprise only one or more of the CDRs of the antibodies described herein (e.g., 1, 2, 3, 4, 5, or 6 CDRs of the antibodies described herein), or may comprise an entire variable domain (VL, VH or both).

In certain embodiments, an FZD10-binding antibody comprises one or more of the CDRs of the antibodies described herein. In this regard, it has been shown in some cases that the transfer of only the VHCDR3 of an antibody can be done while still retaining desired specific binding (Barbas et al., *PNAS* (1995) 92: 2529-2533). See also, McLane et al., *PNAS* (1995) 92:5214-5218, Barbas et al., *J. Am. Chem. Soc.* (1994) 116:2161-2162.

Marks et al (*Bio/Technology*, 1992, 10:779-783) describe methods of producing repertoires of antibody variable domains in which consensus primers directed at or adjacent to the 5' end of the variable domain area are used in conjunction with consensus primers to the third framework region of human VH genes, to provide a repertoire of VH variable domains lacking a CDR3. Marks et al further describe how this repertoire may be combined with a CDR3 of a particular antibody. Using analogous techniques, the CDR3-derived sequences of the presently described antibodies may be shuffled with repertoires of VH or VL domains lacking a CDR3, and the shuffled complete VH or VL domains combined with a cognate VL or VH domain to provide an antibody or antigen-binding fragment thereof that binds FZD10. The repertoire may then be displayed in a suitable host system such as the phage display system of WO92/01047 so that suitable antibodies or antigen-binding fragments thereof may be selected. A repertoire may consist of at least from about $10^4$ individual members and upwards by several orders of magnitude, for example, to about from $10^6$ to $10^8$ or $10^{10}$ or more members. Analogous shuffling or combinatorial techniques are also disclosed by Stemmer (Nature, 1994, 370: 389-391), who describes the technique in relation to a β-lactamase gene but observes that the approach may be used for the generation of antibodies.

A further alternative is to generate novel VH or VL regions carrying one or more CDR-derived sequences of the herein described invention embodiments using random mutagenesis of one or more selected VH and/or VL genes to generate mutations within the entire variable domain. Such a technique is described by Gram et al. (1992 *Proc. Natl. Acad. Sci. USA* 89:3576-3580), who used error-prone PCR. Another method which may be used is to direct mutagenesis to CDR regions of VH or VL genes. Such techniques are disclosed by Barbas et al. (1994 *Proc. Natl. Acad. Sci. USA* 91:3809-3813) and Schier et al. (1996 *J. Mol. Biol.* 263:551-567).

In certain embodiments, a specific VH and/or VL of the antibodies described herein may be used to screen a library of the complementary variable domain to identify antibodies with desirable properties, such as increased affinity for FZD10. Such methods are described, for example, in Portolano et al., J. Immunol. (1993) 150:880-887; Clarkson et al., Nature (1991) 352:624-628.

Other methods may also be used to mix and match CDRs to identify antibodies having desired binding activity, such as binding to FZD10. For example: Klimka et al., *British Journal of Cancer* (2000) 83: 252-260, describe a screening process using a mouse VL and a human VH library with CDR3 and FR4 retained from the mouse VH. After obtaining antibodies, the VH was screened against a human VL library to obtain antibodies that bound antigen. Beiboer et al., J. Mol. Biol. (2000) 296:833-849 describe a screening process using an entire mouse heavy chain and a human light chain library. After obtaining antibodies, one VL was combined with a human VH library with the CDR3 of the mouse retained. Antibodies capable of binding antigen were obtained. Rader et al., PNAS (1998) 95:8910-8915 describe a process similar to that of Beiboer et al above.

These just-described techniques are, in and of themselves, known as such in the art. Based on the present disclosure, the skilled person will, however, be able to use such techniques to obtain antibodies or antigen-binding fragments thereof according to several embodiments of the invention described herein, using routine methodology in the art.

Also disclosed herein is a method for obtaining an antibody antigen binding domain specific for FZD10 antigen, the method comprising providing, by way of addition, deletion, substitution or insertion of one or more amino acids in the amino acid sequence of a VH domain set forth herein, a VH domain which is an amino acid sequence variant of the VH domain. Optionally the VH domain thus provided may be combined with one or more VL domains. The VH domain, or VH/VL combination or combinations, may then be tested to identify a specific binding member or an antibody antigen binding domain specific for FZD10, and optionally further having one or more preferred properties, preferably including the ability to mediate cytotoxicity of cells expressing FZD10. Said VL domains may have an amino acid sequence which is substantially as set out herein. An analogous method may be employed in which one or more sequence variants of a VL domain disclosed herein are combined with one or more VH domains.

An epitope that "specifically binds" or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an FZD10 epitope is an antibody that binds one FZD10 epitope with greater affinity, avidity, more readily, and/or with greater duration than it binds to other FZD10 epitopes or non-FZD10 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) *Annual Rev. Biochem.* 59:439-473.

The term "immunologically active", with reference to an epitope being or "remaining immunologically active", refers to the ability of an antibody (e.g., anti-FZD10 antibody) to bind to the epitope under different conditions, for example, after the epitope has been subjected to reducing and denaturing conditions.

An antibody or antigen-binding fragment thereof according to certain preferred embodiments of the present application may be one that competes for binding to FZD10 with any antibody described herein which both (i) specifically binds to the antigen and (ii) comprises a VH and/or VL domain disclosed herein, or comprises a VH CDR3 disclosed herein, or a variant of any of these. Competition between binding members may be assayed easily in vitro, for example using ELISA and/or by tagging a specific reporter molecule to one binding member which can be detected in the presence of other untagged binding member(s), to enable identification of specific binding members which bind the same epitope or an overlapping epitope.

Thus, there is presently provided a specific antibody or antigen-binding fragment thereof, comprising an antibody antigen-binding site which competes with an antibody described herein that binds to FZD10, such as the antibodies described in the Examples herein (e.g., clones B9L9.3, B9L9.32.2).

The constant regions of immunoglobulins show less sequence diversity than the variable regions, and are responsible for binding a number of natural proteins to elicit important biochemical events. In humans there are five different classes of antibodies including IgA (which includes subclasses IgA1 and IgA2), IgD, IgE, IgG (which includes subclasses IgG1, IgG2, IgG3, and IgG4), and IgM. The distinguishing features between these antibody classes are their constant regions, although subtler differences may exist in the V region.

The Fc region of an antibody interacts with a number of Fc receptors and ligands, imparting an array of important functional capabilities referred to as effector functions. For IgG the Fc region comprises Ig domains CH2 and CH3 and the N-terminal hinge leading into CH2. An important family of Fc receptors for the IgG class are the Fc gamma receptors (FcγRs). These receptors mediate communication between antibodies and the cellular arm of the immune system (Raghavan et al., 1996, *Ann. Rev. Cell Dev. Biol.* 12:181-220; Ravetch et al., 2001, *Ann. Rev. Immunol.* 19:275-290). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, *Immunol Lett* 82:57-65). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack.

The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, *Ann. Rev. Cell Dev. Biol.* 12:181-220; Ghetie et al., 2000, *Ann. Rev. Immunol.* 18:739-766; Ravetch et al., 2001, *Ann. Rev. Immunol.* 19:275-290). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP). All FcγRs bind the same region on Fc, at the N-terminal end of the Cg2 (CH2) domain and the preceding hinge. This interaction is well characterized structurally (Sondermann et al., 2001, *J Mol Biol* 309: 737-749), and several structures of the human Fc bound to the extracellular domain of human FcγRIIIb have been solved (pdb accession code 1E4K)(Sondermann et al., 2000, *Nature* 406:267-273.) (pdb accession codes 1IIS and 1IIX)(Radaev et al., 2001, *J Biol Chem* 276:16469-16477.)

The different IgG subclasses have different affinities for the FcγR5, with IgG1 and IgG3 typically binding substantially better to the receptors than IgG2 and IgG4 (Jefferis et al., 2002, *Immunol Lett* 82:57-65). All FcγRs bind the same region on IgG Fc, yet with different affinities: the high affinity binder FcγRI has a Kd for IgG1 of $10^{-8}$ M$^{-1}$, whereas the low affinity receptors FcγRII and FcγRIII generally bind at $10^{-6}$ and $10^{-6}$ respectively. The extracellular domains of FcγRIIIa and FcγRIIIb are 96% identical, however FcγRIIIb does not have a intracellular signaling domain. Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. The receptors also differ in expression pattern and levels on different immune cells. Yet another level of complexity is the existence of a number of FcγR polymorphisms in the human proteome. A particularly relevant polymorphism with clinical significance is V158/F158 FcγRIIIa. Human IgG1 binds with greater affinity to the V158 allotype than to the F158 allotype. This difference in affinity, and presumably its effect on ADCC and/or ADCP, has been shown to be a significant determinant of the efficacy of the anti-CD20 antibody rituximab (Rituxan®, a registered trademark of IDEC Pharmaceuticals Corporation). Patients with the V158 allotype respond favorably to rituximab treatment; however, patients with the lower affinity F158 allotype respond poorly (Cartron et al., 2002 *Blood* 99:754-758). Approximately 10-20% of humans are V158N158 homozygous, 45% are V158/F158 heterozygous, and 35-45% of humans are F158/F158 homozygous (Lehrnbecher et al., 1999 *Blood* 94:4220-4232; Cartron et al., 2002 *Blood* 99:754-758). Thus 80-90% of humans are poor responders, that is they have at least one allele of the F158 FcγRIIIa.

The Fc region is also involved in activation of the complement cascade. In the classical complement pathway, C1 binds with its C1q subunits to Fc fragments of IgG or IgM, which has formed a complex with antigen(s). In certain embodiments of the invention, modifications to the Fc region comprise modifications that alter (either enhance or decrease) the ability of a herein described FZD10-specific antibody to activate the complement system (see e.g., U.S. Pat. No. 7,740,847). To assess complement activation, a complement-dependent cytotoxicity (CDC) assay may be performed (See, e.g., Gazzano-Santoro et al., *J. Immunol. Meth.* 202:163 (1996)). For example, various concentrations of the (Fc) variant polypeptide and human complement may be diluted with buffer. Mixtures of (Fc) variant antibodies, diluted human complement and cells expressing the antigen (FZD10) may be added to a flat bottom tissue culture 96 well plate and allowed to incubate for 2 hours at 37° C. and 5% $CO_2$ to facilitate complement mediated cell lysis. Fifty microliters of alamar blue (Accumed International) may then be added to each well and incubated overnight at 37° C. The absorbance may be measured using a 96-well fluorimeter with excitation at 530 nm and emission at 590 nm. The results may be expressed in relative fluorescence units (RFU). The sample concentrations may be computed from a standard curve and the percent activity as compared to nonvariant antibody may be reported for the variant antibody of interest.

Thus in certain embodiments, the present invention provides anti-FZD10 antibodies having a modified Fc region with altered functional properties, such as enhanced ADCC, ADCP, CDC, or enhanced binding affinity for a specific FcγR. Illustrative modifications of the Fc region include those described in, e.g., Stavenhagen et al., 2007 *Cancer Res.* 67:8882. Other modified Fc regions contemplated herein are described, for example, in issued U.S. Pat. Nos. 7,317,091; 7,657,380; 7,662,925; 6,538,124; 6,528,624; 7,297,775; 7,364,731; Published U.S. Applications US2009092599; US20080131435; US20080138344; and published International Applications WO2006/105338; WO2004/063351; WO2006/088494; WO2007/024249.

The desired functional properties of anti-FZD10 antibodies may be assessed using a variety of methods known to the skilled person, including but not limited to ADCC assays (see Example section), ADCP assays, affinity/binding assays (for example, surface plasmon resonance, competitive inhibition assays); cytotoxicity assays, cell viability assays (e.g., using dye exclusion such as Trypan Blue, propidium iodide, etc), cancer cell and/or tumor growth inhibition using in vitro or in vivo models (e.g., cell proliferation and/or colony formation assays; anchorage-dependent proliferation assays; standard human tumor xenograft models) (see, e.g., Culp P A, et al., *Clin. Cancer Res.* 16(2):497-508). Other assays may test the ability of antibodies described herein to block normal FZD10-mediated responses, such as cell proliferation, cell differentiation (e.g., stem and progenitor cell differentiation), and in certain cell types, immunoregulatory functions. Such assays may be performed using well-established protocols known to the skilled person (see e.g., Current Protocols in Molecular Biology (Greene Publ. Assoc. Inc. & John Wiley & Sons, Inc., NY, N.Y.); Current Protocols in Immunology (Edited by: John E. Coligan, Ada M. Kruisbeek, David H. Margulies, Ethan M. Shevach, Warren Strober 2001 John Wiley & Sons, NY, N.Y.); or commercially available kits.

In one embodiment, the anti-FZD10 antibodies described herein block binding of WNT7a and/or WNT7b, or any other ligand for FZD10, to the FZD10 receptor. Binding assays and competitive inhibition assays may be used to determine blocking activity of the antibodies described herein, or variants or antigen-binding fragments thereof.

In certain embodiments, the anti-FZD10 antibodies described herein bind to FZD10 and block or inhibit downstream signaling events in the canonical Wnt signalling pathway. In particular embodiments, a level of Wnt signaling inhibition provided by an anti-FZD10 antibody may be a statistically significant reduction in the level of signaling by Wnt7a and/or Wnt7b of at least about 10%, at least about 25%, at least about 50%, at least about 60%, 65%, 70%, 75%, 80%, 85%, at least about 90%, or at least about 95%, relative to the level of Wnt signaling in the absence of the herein disclosed anti-FZD10 antibody.

Thus, the present disclosure provides anti-FZD10 antibodies that modulate components of the canonical Wnt signalling pathway. By modulate it is meant to alter activity, protein level, gene expression level, or phosphorylation state of a component of the Wnt signalling pathway in a statistically significant manner (e.g., to inhibit in a statistically significant manner, or to increase in a statistically significant manner, as measured using appropriate controls). A component of the canonical Wnt signalling pathway includes, but is not limited to, LRPs (Low Density Lipoprotein Receptor-related Proteins such as LRP5, LRP6), axin, casein kinases (CK1, CK2), Frat/GBP family of glycogen synthase kinase 36 (Gsk3b)-binding oncoproteins, Microtubule affinity—regulating kinase (MARK; PAR-1), Dishevelled, glycogen synthase kinase 3b (GSK-3b), Adenomatous polyposis coli protein (APC; also referred to as deleted in polyposis 2.5 (DP2.5)), β-catenin, (T cell factor)/LEF-1 (lymphoid enhancer factor 1) family of DNA binding proteins (transcription factors), β-catenin-TCF, and genes regulated by β-catenin-TCF. β-catenin, in an active form, is a transcriptional activator for the TCF/LEF-1 (lymphoid enhancer factor 1) family of DNA binding proteins. Examples of TCF-responsive genes include c-myc and cyclin D1.

In certain embodiments, modulation of components of the Wnt signalling pathway may comprise modulation of the phosphorylation state of one or more components of the pathway. In certain embodiments, binding of the anti-FZD10 antibodies of the present invention to the FZD10 receptor may cause, in a statistically significant manner, one or more of decreased phosphorylation of Dishevelled, decreased phosphorylation of c-Jun, and increased phosphorylation of β-catenin.

In vivo and in vitro assays for determining whether an antibody inhibits Wnt signaling are known in the art. For example, cell-based, luciferase reporter assays utilizing a TCF/Luc reporter vector containing multiple copies of the TCF-binding domain upstream of a firefly luciferase reporter gene may be used to measure canonical Wnt signaling levels in vitro (Gazit et al., 1999, *Oncogene* 18; 5959-66). Such assays are also described herein in Example 4. The level of Wnt signaling in the presence of one or more Wnts (e.g., Wnt(s) expressed by transfected cells or provided by Wnt-conditioned media) with the FZD10-binding antibody present is compared to the level of signaling without the FZD10-binding antibody present. Non-limiting, specific examples of the use of such a luciferase reporter assay to assess inhibition of canonical Wnt signaling are provided in the Examples herein. In addition to the TCF/luc reporter assay, the effect of a FZD10-binding antibody on canonical Wnt signaling may be measured in vitro or in vivo by measuring the effect of the antibody on the level of expression of beta-catenin regulated genes, such as c-myc (He et al., *Science* 281:1509-12 (1998)), cyclin D1 (Tetsu et al., *Nature* 398:422-6 (1999)) and/or fibronectin (Gradl et al., *Mol. Cell Biol.* 19:5576-87 (1999)). In certain embodiments, the effect of an antibody described herein on Wnt signaling may also be assessed by measuring the effect of the antibody on the phosphorylation state of Dishevelled-1, Dishevelled-2, Dishevelled-3, LRP5, LRP6, and/or β-catenin. In other embodiments, the effect of a FZD-binding antibody on Wnt signaling is determined by assessing the effect of the FZD-binding antibody on the expression level of one or more genes in a Wnt signature. Other assays and commercially available systems for determining modulation of components of the canonical Wnt signalling pathway are known to the skilled person.

The present invention provides, in certain embodiments, an isolated nucleic acid encoding an antibody or antigen-binding fragment thereof as described herein, for instance, a nucleic acid which codes for a CDR or VH or VL domain. Nucleic acids include DNA and RNA. These and related embodiments may include polynucleotides encoding antibodies that bind FZD10 as described herein. The term "isolated polynucleotide" as used herein shall mean a polynucleotide of genomic, cDNA, or synthetic origin or some combination thereof, which by virtue of its origin the isolated polynucleotide (1) is not associated with all or a portion of a polynucleotide in which the isolated polynucleotide is found in nature, (2) is linked to a polynucleotide to which it is not linked in nature, or (3) does not occur in nature as part of a larger sequence.

The term "operably linked" means that the components to which the term is applied are in a relationship that allows them to carry out their inherent functions under suitable conditions. For example, a transcription control sequence "operably linked" to a protein coding sequence is ligated thereto so that expression of the protein coding sequence is achieved under conditions compatible with the transcriptional activity of the control sequences.

The term "control sequence" as used herein refers to polynucleotide sequences that can affect expression, processing or intracellular localization of coding sequences to which they are ligated or operably linked. The nature of such control sequences may depend upon the host organism. In particular embodiments, transcription control sequences for prokaryotes may include a promoter, ribosomal binding site, and transcription termination sequence. In other particular embodiments, transcription control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "polynucleotide" as referred to herein means single-stranded or double-stranded nucleic acid polymers. In certain embodiments, the nucleotides comprising the polynucleotide can be ribonucleotides or deoxyribonucleotides or a modified form of either type of nucleotide. Said modifications include base modifications such as bromouridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phosphoraniladate and phosphoroamidate. The term "polynucleotide" specifically includes single and double stranded forms of DNA.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotide linkages such as phosphorothioate, phosphorodithioate, phosphoroselenoate, phosphorodiselenoate, phosphoroanilothioate, phosphoraniladate, phosphoroamidate, and the like. See, e.g., LaPlanche et al., 1986, *Nucl. Acids Res.*, 14:9081; Stec et al., 1984, *J. Am. Chem. Soc.*, 106:6077; Stein et al., 1988, *Nucl. Acids Res.*, 16:3209; Zon et al., 1991, *Anti-Cancer Drug Design*, 6:539; Zon et al., 1991, Oligonucleotides and Analogues: A Practical Approach, pp. 87-108 (F. Eckstein, Ed.), Oxford University Press, Oxford England; Stec et al., U.S. Pat. No. 5,151,510; Uhlmann and Peyman, 1990, *Chemical Reviews*, 90:543, the disclosures of which are hereby incorporated by reference for any purpose. An oligonucleotide can include a detectable label to enable detection of the oligonucleotide or hybridization thereof.

The term "vector" is used to refer to any molecule (e.g., nucleic acid, plasmid, or virus) used to transfer coding information to a host cell. The term "expression vector" refers to a vector that is suitable for transformation of a host cell and contains nucleic acid sequences that direct and/or control expression of inserted heterologous nucleic acid sequences. Expression includes, but is not limited to, processes such as transcription, translation, and RNA splicing, if introns are present.

As will be understood by those skilled in the art, polynucleotides may include genomic sequences, extra-genomic and plasmid-encoded sequences and smaller engineered gene segments that express, or may be adapted to express, proteins, polypeptides, peptides and the like. Such segments may be naturally isolated, or modified synthetically by the skilled person.

As will also be recognized by the skilled artisan, polynucleotides may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide according to the present disclosure, and a polynucleotide may, but need not, be linked to other molecules and/or support materials. Polynucleotides may comprise a native sequence or may comprise a sequence that encodes a variant or derivative of such a sequence.

Therefore, according to these and related embodiments, polynucleotides are provided that comprise some or all of a polynucleotide sequence set forth in any one of SEQ ID NOs:19-22, complements of a polynucleotide sequence set forth in any one of SEQ ID NOs: 19-22, and degenerate variants of a polynucleotide sequence set forth in any one of SEQ ID NOs:19-22. In certain preferred embodiments, the polynucleotide sequences set forth herein encode antibodies, or antigen-binding fragments thereof, which bind the FZD10, as described elsewhere herein.

In other related embodiments, polynucleotide variants may have substantial identity to the sequences disclosed herein in SEQ ID NOs:19-22, for example those comprising at least 70% sequence identity, preferably at least 75%, 80%, 85%, 90%, 95%, 96%, 97%, 98%, or 99% or higher, sequence identity compared to a reference polynucleotide sequence such as the sequences disclosed herein, using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the binding affinity of the antibody encoded by the variant polynucleotide is not substantially diminished relative to an antibody encoded by a polynucleotide sequence specifically set forth herein.

In certain other related embodiments, polynucleotide fragments may comprise or consist essentially of various lengths of contiguous stretches of sequence identical to or complementary to one or more of the sequences disclosed herein. For example, polynucleotides are provided that comprise or consist essentially of at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 110, 120, 130, 140, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 50, 51, 52, 53, etc.; 100, 101, 102, 103, etc.; 150, 151, 152, 153, etc.; including all integers through 200-500; 500-1,000, and the like. A polynucleotide sequence as described here may be extended at one or both ends by additional nucleotides not found in the native sequence. This additional sequence may consist of 1, 2, 3, 4, 5, 6, 7, 8, 9, 10, 11, 12, 13, 14, 15, 16, 17, 18, 19, or 20 nucleotides at either end of the disclosed sequence or at both ends of the disclosed sequence.

In another embodiment, polynucleotides are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide as provided herein with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60-65° C. or 65-70° C.

In certain embodiments, the polynucleotides described above, e.g., polynucleotide variants, fragments and hybridizing sequences, encode antibodies that bind FZD10, or antigen-binding fragments thereof. In other embodiments, such polynucleotides encode antibodies or antigen-binding fragments, or CDRs thereof, that bind to FZD10 at least about 50%, preferably at least about 70%, and more preferably at least about 90% as well as an antibody sequence specifically set forth herein. In further embodiments, such polynucleotides encode antibodies or antigen-binding fragments, or CDRs thereof, that bind to FZD10 with greater affinity than the antibodies set forth herein, for example, that bind quantitatively at least about 105%, 106%, 107%, 108%, 109%, or 110% as well as an antibody sequence specifically set forth herein.

Determination of the three-dimensional structures of representative polypeptides (e.g., variant FZD10-specific antibodies as provided herein, for instance, an antibody protein having an antigen-binding fragment as provided herein) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. See, for instance, Donate et al., 1994 *Prot. Sci.* 3:2378; Bradley et al., *Science* 309: 1868-1871 (2005); Schueler-Furman et al., *Science* 310:638 (2005); Dietz et al., *Proc. Nat. Acad. Sci. USA* 103:1244 (2006); Dodson et al., *Nature* 450:176 (2007); Qian et al., *Nature* 450:259 (2007); Raman et al. *Science* 327:1014-1018 (2010). Some additional non-limiting examples of computer algorithms that may be used for these and related embodiments, such as for rational design of FZD10-specific antibodies antigen-binding domains thereof as provided herein, include NAMD, a parallel molecular dynamics code designed for high-performance simulation of large biomolecular systems, and VMD which is a molecular visualization program for displaying, animating, and analyzing large biomolecular systems using 3-D graphics and built-in scripting (see Phillips, et al., *Journal of Computational Chemistry,* 26:1781-1802, 2005; Humphrey, et al., "VMD—Visual Molecular Dynamics", *J. Molec. Graphics,* 1996, vol. 14, pp. 33-38; see also the website for the Theoretical and Computational Biophysics Group, University of Illinois at Urbana-Champagne, at ks.uiuc.edu/Research/vmd/). Many other computer programs are known in the art and available to the skilled person and which allow for determining atomic dimensions from space-filling models (van der Waals radii) of energy-minimized conformations; GRID, which seeks to determine regions of high affinity for different chemical groups, thereby enhancing binding, Monte Carlo searches, which calculate mathematical alignment, and CHARMM (Brooks et al. (1983) *J. Comput. Chem.* 4:187-217) and AMBER (Weiner et al (1981) *J. Comput. Chem.* 106: 765), which assess force field calculations, and analysis (see also, Eisenfield et al. (1991) *Am. J. Physiol.* 261:C376-386; Lybrand (1991) *J. Pharm. Belg.* 46:49-54; Froimowitz (1990) *Biotechniques* 8:640-644; Burbam et al. (1990) *Proteins* 7:99-111; Pedersen (1985) *Environ. Health Perspect.* 61:185-190; and Kini et al. (1991) *J. Biomol. Struct. Dyn.* 9:475-488). A variety of appropriate computational computer programs are also commercially available, such as from Schrödinger (Munich, Germany).

The polynucleotides described herein, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) *Atlas of Protein Sequence and Structure*, National Biomedical Research Foundation, Washington D.C. Vol. 5, Suppl. 3, pp. 345-358; Hein J., *Unified Approach to Alignment and Phylogenes*, pp. 626-645 (1990); *Methods in Enzymology* vol. 183, Academic Press, Inc., San Diego, Calif.; Higgins, D. G. and Sharp, P. M., *CABIOS* 5:151-153 (1989); Myers, E. W. and Muller W., *CABIOS* 4:11-17 (1988); Robinson, E. D., *Comb. Theor* 11:105 (1971); Santou, N. Nes, M., *Mol. Biol. Evol.* 4:406-425 (1987); Sneath, P. H. A. and Sokal, R. R., *Numerical Taxonomy—the Principles and Practice of Numerical Taxonomy*, Freeman Press, San Francisco, Calif. (1973); Wilbur, W. J. and Lipman, D. J., *Proc. Natl. Acad., Sci. USA* 80:726-730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389-3402 (1977), and Altschul et al., *J. Mol. Biol.* 215:403-410 (1990), respectively. BLAST and BLAST 2.0 can be used, for example with the parameters described herein, to determine percent sequence identity among two or more the polynucleotides. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff, *Proc. Natl. Acad. Sci. USA* 89:10915 (1989)) alignments, (B) of 50, expectation (E) of 10, M=5, N=−4 and a comparison of both strands.

In certain embodiments, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode an antibody as described herein. Some of these polynucleotides bear minimal sequence identity to the nucleotide sequence of the native or original polynucleotide sequence, such as those described herein that encode antibodies that bind to FZD10. Nonetheless, polynucleotides that vary due to differences in codon usage are expressly contemplated by the present disclosure. In certain embodiments, sequences that have been codon-optimized for mammalian expression are specifically contemplated.

Therefore, in another embodiment of the invention, a mutagenesis approach, such as site-specific mutagenesis, may be employed for the preparation of variants and/or derivatives of the antibodies described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments, the inventors contemplate the mutagenesis of the disclosed polynucleotide sequences to alter one or more properties of the encoded polypeptide, such as the binding affinity of the antibody or the antigen-binding fragment thereof, or the ADCC function of a particular Fc region, or the affinity of the Fc region for a particular FcγR. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as $E.$ $coli$ polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as $E.$ $coli$ cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants, recursive sequence recombination, as described in U.S. Pat. No. 5,837,458, may be employed. In this approach, iterative cycles of recombination and screening or selection are performed to "evolve" individual polynucleotide variants having, for example, increased binding affinity. Certain embodiments also provide constructs in the form of plasmids, vectors, transcription or expression cassettes which comprise at least one polynucleotide as described herein.

According to certain related embodiments there is provided a recombinant host cell which comprises one or more constructs as described herein; a nucleic acid encoding any antibody, CDR, VH or VL domain, or antigen-binding fragment thereof; and a method of production of the encoded product, which method comprises expression from encoding nucleic acid therefor. Expression may conveniently be achieved by culturing under appropriate conditions recombinant host cells containing the nucleic acid. Following production by expression, an antibody or antigen-binding fragment thereof, may be isolated and/or purified using any suitable technique, and then used as desired.

Antibodies or antigen-binding fragments thereof as provided herein, and encoding nucleic acid molecules and vectors, may be isolated and/or purified, e.g. from their natural environment, in substantially pure or homogeneous form, or, in the case of nucleic acid, free or substantially free of nucleic acid or genes of origin other than the sequence encoding a polypeptide with the desired function. Nucleic acid may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is *E. coli*.

The expression of antibodies and antigen-binding fragments in prokaryotic cells such as *E. coli* is well established in the art. For a review, see for example Pluckthun, A. Bio/Technology 9: 545-551 (1991). Expression in eukaryotic cells in culture is also available to those skilled in the art as an option for production of antibodies or antigen-binding fragments thereof, see recent reviews, for example Ref, M. E. (1993) Curr. Opinion Biotech. 4: 573-576; Trill J. J. et al. (1995) Curr. Opinion Biotech 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press; see also the additional references cited below pertaining to molecular biology methods. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992, or subsequent updates thereto.

The term "host cell" is used to refer to a cell into which has been introduced, or which is capable of having introduced into it, a nucleic acid sequence encoding one or more of the herein described antibodies, and which further expresses or is capable of expressing a selected gene of interest, such as a gene encoding any herein described antibody. The term includes the progeny of the parent cell, whether or not the progeny are identical in morphology or in genetic make-up to the original parent, so long as the selected gene is present. Accordingly there is also contemplated a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene. In one embodiment, the nucleic acid is integrated into the genome (e.g. chromosome) of the host cell. Integration may be promoted by inclusion of sequences which promote recombination with the genome, in accordance-with standard techniques.

The present invention also provides, in certain embodiments, a method which comprises using a construct as stated above in an expression system in order to express a particular polypeptide such as an FZD10-specific antibody as described herein. The term "transduction" is used to refer to the transfer of genes from one bacterium to another, usually by a phage. "Transduction" also refers to the acquisition and transfer of eukaryotic cellular sequences by retroviruses. The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, MOLECULAR CLONING, A LABORATORY MANUAL, Cold Spring Harbor Laboratories; Davis et al., 1986, BASIC METHODS 1N MOLECULAR BIOLOGY, Elsevier; and Chu et al., 1981, Gene 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell. The term "naturally occurring" or "native" when used in connection with biological materials such as nucleic acid molecules, polypeptides, host cells, and the like, refers to materials which are found in nature and are not manipulated by a human. Similarly, "non-naturally occurring" or "non-native" as used herein refers to a material that is not found in nature or that has been structurally modified or synthesized by a human.

The terms "polypeptide" "protein" and "peptide" and "glycoprotein" are used interchangeably and mean a polymer of amino acids not limited to any particular length. The term does not exclude modifications such as myristylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the antibodies that bind to FZD10 of the present disclosure, or sequences that have deletions from, additions to, and/or substitutions of one or more amino acid of an anti-FZD10 antibody. Thus, a "polypeptide" or a "protein" can comprise one (termed "a monomer") or a plurality (termed "a multimer") of amino acid chains.

The term "isolated" with respect to a protein referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

The term "polypeptide fragment" refers to a polypeptide, which can be monomeric or multimeric, that has an amino-terminal deletion, a carboxyl-terminal deletion, and/or an internal deletion or substitution of a naturally-occurring or recombinantly-produced polypeptide. In certain embodiments, a polypeptide fragment can comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long. Particularly useful polypeptide fragments include functional domains, including antigen-binding domains or fragments of antibodies. In the case of an anti-FZD10 antibody, useful fragments include, but are not limited to: a CDR region, especially a CDR3 region of the heavy or light chain; a variable domain of a heavy or light chain; a portion of an antibody chain or just its variable region including two CDRs; and the like.

Methods for Generating FZD10-Specific Antibodies

The antibodies according to certain embodiments of the present invention may be generated using an in vitro system based on the DT40 chicken B cell lymphoma line. The DT40 chicken B cell lymphoma line has been used for antibody evolution ex vivo (Cumbers, S. J. et al. *Nat Biotechnol* 20:1129-1134 (2002); Seo, H. et al. *Nat Biotechnol* 23:731-735 (2005).). DT40 cells command enormous potential V region sequence diversity, as they can access two distinct physiological pathways for diversification, gene conversion and somatic hypermutation, which create templated and non-templated mutations, respectively (Maizels, N., Immunoglobulin gene diversification. Ann. Rev. Genet. 39:23-46 (2005)). However, the utility of DT40 cells for antibody evolution has been limited in practice because—as in other transformed B cell lines—diversification occurs at less than 1% the physiological rate. Diversification can be accelerated several-fold by disabling the homologous recombination pathway (Cumbers et al., supra), but cells thus engineered lose the ability to carry out efficient gene targeting. Diversification can also be accelerated by treatment of cells with the histone deacetylase inhibitor, trichostatin A (Seo et al., supra), but resulting mutations are exclusively templated, which limits potential diversity and may not produce antibodies of required affinity or specificity.

The DT40 cells used herein to generate antibodies are modified to accelerate the rate of Ig gene diversification without sacrificing the capacity for further genetic modification or the potential for both gene conversion and somatic hypermutation to contribute to mutagenesis. This was accomplished by putting immunoglobulin (Ig) gene diversification under control of the potent *E. coli* lactose operator/repressor regulatory network. Multimers consisting of approximately 100 polymerized repeats of the potent *E. coli* lactose operator (PolyLacO) were inserted upstream of the rearranged and expressed Igλ and IgH genes by homologous gene targeting. Regulatory factors fused to lactose repressor protein (LacI) can then be tethered to the LacO regulatory elements to regulate diversification, taking advantage of the high affinity ($K_D=10^{-14}$ M) of lactose repressor for operator DNA. DT40 PolyLacO-$\lambda_R$ cells, in which PolyLacO was integrated only at Igλ, exhibited a 5-fold increase in Ig gene diversification rate relative to the parental DT40 cells prior to any engineering (Cummings, W. J. et al. *PLoS Biol* 5, e246 (2007)). Diversification was further elevated in cells engineered to carry PolyLacO targeted to both the Igλ and the IgH genes ("DTLacO").

The engineered DTLacO line, which carries PolyLacO at both the heavy and light chain genes, may be used as the starting point for antibody discovery ex vivo. For instance, as described in the Examples, starting with a diversified population of between $10^7$-$10^{10}$ DTLacO LacI-HP1 cells, cells that bind to FZD10 were enriched by rounds of selection on FZD10-bearing solid matrices (Dynal magnetic beads) and by FACS. As would be recognized by the skilled artisan, other methods of selection (e.g., based on antibody binding specificity for FZD10) may also be used. Recombinant chimeric monoclonal antibodies having desired binding characteristics are then generated using standard techniques as described herein.

In certain embodiments, (e.g., for generating variants of the anti-FZD10 antibodies described herein; for generating antibodies that block binding of the anti-FZD10 antibodies described herein) selection of antigen-specific DTLacO cells can then be tested using any of a variety of high throughput approaches including, but not limited to, panning and cell:target cell binding. For example, panning can be carried out by incubating a diverse DTLacO population that contains a low percentage of FZD10-specific cells with an array of multiple soluble antigen targets bound to a plastic matrix. Panning significantly enriches FZD10-specific DTLacO cells. DTLacO:target cell selection can be carried out by co-incubating a diverse DTLacO population that contained a low percentage of CFSE-labeled DTLacO FZD10-binding cells or unselected DTLacO with target cells expressing the antigen of interest, e.g., FZD10-expressing cells, which constitutively or transiently express either native or recombinant FZD10 on the cell surface, then quantifying DTLacO cells bound to the target cells by flow cytometry. DTLacO interactions with target cells are evident as CFSE-positive events on a dot plot, with the signal from much smaller free DTLacO cells eliminated based on forward scatter.

In certain embodiments, (e.g., for generating antibodies that block binding of the anti-FZD10 antibodies described herein) antibodies may similarly be prepared using an in vitro system for generating diversity of a particular polypeptide, as further described in WO2009029315 and US2010093033. In particular, these applications generally relate to the modified B cell, such as the DT40 cell line described herein above, that permits reversible induction of diversification of a target gene. The illustrative B cell is the DT40 B cell line, however the use of other B cells, including human B cells, is contemplated. DT40 is a chicken B cell line that is known to constitutively mutate its heavy and light chain immunoglobulin (Ig) genes in culture. Like other B cells, this constitutive mutagenesis targets mutations to the V region of Ig genes, and thus, the CDRs of the expressed antibody molecules. Constitutive mutagenesis in DT40 cells takes place by gene conversion using as donor sequences an array of non-functional V gene segments (pseudo-V genes; ψV) situated upstream of each functional V region. Deletion of the ψV region was previously shown to cause a switch in the mechanism of diversification from gene conversion to somatic hypermutation, the mechanism commonly observed in human B cells. DT40 has also been shown to support efficient homologous recombination which enables the creation of modified cells in which specific genes are modified, deleted or inserted or where specific genes of interest replace an endogenous gene, in particular an endogenous rearranged Ig gene.

The system described in WO2009029315 and US2010093033 takes advantage of these and other properties to create a platform for diversifying target sequences. More specifically, in its broadest form, therein is described a modified B cell that permits reversible induction of diversification of a target gene. The cells are modified to include a "cis-regulatory element" operably linked to a target gene of interest. The cell is further modified to include a "diversification factor" that is fused to a "tethering factor". The function of the tethering factor is to bind to the cis-regulatory element, thereby bringing the diversification factor to the region that controls expression of the target gene. The role of the diversification factor is to accelerate or regulate diversification (mutation) of the target sequence. Since the target gene is inserted into an Ig locus, mutations are targeted to its coding region and controlled by the use of the diversification factor-tethering factor fusion protein. Generally, the cis-regulatory element may be any DNA sequence that allows binding of a tethering factor thereto in a sequence-specific manner and is positioned in a region that controls expression or diversification of a gene (the gene of interest). The cis-regulatory elements include a polymerized Lactose operator (PolyLacO) comprising approximately 100 repeats of the 20 base pair LacO binding site. The cis-regulatory element is positioned within the ψV region of the Igλ light chain and the IgH loci. The tethering factor includes the Lac repressor (LacI) that binds with high affinity to the LacO. This insertion of the cis-regulatory element does not affect the normal process of templated mutagenesis (gene conversion) in the modified DT40 cell line.

The inducible aspect of the system of WO2009029315 and US2010093033 occurs through expression of tethering factor (LacI)-diversification factor fusion proteins and the use of IPTG, a small molecule which causes release of LacI from LacO. Culture of the modified DT40 cells with as little as 10 µM IPTG causes release of LacI from the PolyLacO and does not affect cell proliferation. Many different diversification factors are contemplated and include factors that affect chromatin structure, transcriptional activators and other gene regulators, deaminases, proteins involved in DNA repair and replication, resolvases and helicases, cell cycle regulators, proteins of the nuclear pore complex, and proteins involved in ubiquitylation. Different tethering factor-diversification factor constructs include: 1) LacI-HP1: The heterochromatin protein, HP1, promotes a closed chromatin structure of neighboring genes. Thus, when LacI was bound to the PolyLacO in the modified DT40 cells, the tethered HP1 protein caused a transition of the donor ψV sequences from an open to a nonpermissive chromatin state. This was functionally equivalent to the deletion of the ψV region and similarly resulted in the switch from a templated mutagenesis of the downstream Ig Vλ locus to a somatic hypermutation of this targeted region. 2) LacI-VP16: VP16 is a strong transcriptional activator which functions by recruiting histone acetyltransferase complexes. Binding of the LacI-VP16 fusion to the PolyLacO tract resulted in a permissive chromatin structure and an increase in mutagenesis of the Vλ targeted region by gene conversion. 3) LacI-Nup153: Nup153 is a nuclear pore protein and the LacI-Nup153 fusion protein functioned to tether the IgH locus in the modified DT40 cells to the nuclear pore. Since diversification of Ig genes was shown to initiate at the nuclear periphery, mediated by Activation Induced Deaminase (AID) which carries a nuclear export signal, the effect of binding of the LacI-Nup153 fusion protein to the PolyLacO tract was to accelerate diversification by increasing gene proximity to the nuclear pore. The experiments described show that the clonal diversification rate accelerated by 5.7-fold. 4) E47-LacI: E47 is an isoform of E2A, which is a regulator of many aspects of lymphocyte development. This protein is induced in activated murine B cells where it regulates class switch recombination as well as expression of the AID gene. Inactivation of the E2A gene impairs Igλ gene diversification. Similarly, ectopic expression of E47 promotes Igλ gene diversification. Thus, binding of the E47-LacI fusion protein to the PolyLacO cis-regulatory element in the modified DT40 cells resulted in an increase in the diversification of the downstream targeted gene. 5) HIRA-LacI: HIRA is a histone chaperone. One of its functions is to assemble nucleosomes containing the H3.3 histone variant. Expression of the HIRA-LacI fusion protein in the PolyLacO modified DT40 cells increased diversification 11-fold. This acceleration was shown to be due to increased levels of templated mutation (gene conversion).

The modified B cells described in WO2009029315 and US2010093033 may be used to generate mutated proteins, and in certain embodiments may be used to generate anti-FZD10 antibodies, such as antibodies that block specific binding of the antibodies described herein to their cognate antigens, for instance, by competitive inhibition.

FZD10-binding antibodies or antigen-binding fragments thereof as described herein which are modulators, agonists or antagonists of FZD10 function are expressly included within the contemplated embodiments. These agonists, antagonists and modulator antibodies or antigen-binding fragments thereof interact with one or more of the antigenic determinant sites of FZD10, or epitope fragments or variants of FZD10. In certain embodiments, the FZD10-binding antibodies described herein bind to an epitope in the extracellular domain (ECD) of FZD10. In certain embodiments, the antibodies herein do not cross-react with other members of the frizzled receptor family (e.g., in certain embodiments the antibodies described herein do not bind to FZD9, FZD8, FZD7, FZD6, FZD5, FZD4, FZD3, FZD2, or FZD1). In other embodiments, the anti-FZD10 antibodies described herein may cross-react with one or more other frizzled receptor family proteins.

As would be recognized by the skilled person, there are many known methods for making antibodies that bind to a particular antigen, such as FZD10, including standard technologies, see, e.g., Harlow and Lane, *Antibodies: A Laboratory Manual*, Cold Spring Harbor Laboratory, 1988. In general, antibodies, such as antibodies that specifically block binding of the FZD10-binding antibodies expressly disclosed herein to their cognate antigens, can be produced by cell culture techniques, including the generation of monoclonal antibodies as described herein, or via transfection of antibody genes into suitable bacterial or mammalian cell hosts, in order to allow for the production of recombinant antibodies. In certain embodiments, an immunogen comprising a polypeptide antigen (e.g., human FZD10 protein comprising amino acid sequence as set forth in SEQ ID NO:28) is initially injected into any of a wide variety of mammals (e.g., mice, rats, rabbits, sheep or goats). In this step, the polypeptide may serve as the immunogen without modification. Alternatively, particularly for relatively short polypeptides, a superior immune response may in some cases be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

In certain embodiments, monoclonal antibodies specific for an antigenic polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides may be used in the purification process in, for example, an affinity chromatography step.

Methods of Use and Pharmaceutical Compositions

Provided herein are methods of treatment using the antibodies that bind FZD10. In one embodiment, an antibody of the present invention is administered to a patient having a disease involving inappropriate expression of FZD10, which is meant in the context of the present disclosure to include diseases and disorders characterized by aberrant FZD10, due for example to alterations (e.g., statistically significant increases or decreases) in the amount of a protein present, or the presence of a mutant protein, or both. An overabundance may be due to any cause, including but not limited to overexpression at the molecular level, prolonged or accumulated appearance at the site of action, or increased (e.g., in a statistically significant manner) activity of FZD10 relative to that which is normally detectable. Such an overabundance of FZD10 can be measured relative to normal expression, appearance, or activity of FZD10, and said measurement may play an important role in the development and/or clinical testing of the antibodies described herein.

In particular, the present antibodies are useful for the treatment of a variety of cancers associated with the expression of FZD10. For example, one embodiment of the invention provides a method for the treatment of a cancer including, but not limited to, synovial sarcoma, colorectal carcinoma, gastric carcinoma, chronic myeloid leukemia (CML), acute myeloid leukemia (AML), melanoma, salivary carcinomas, breast cancer, hepatocellular carcinoma, ovarian cancer, cervical cancer, non-small cell lung cancer (NSCLC; both adenocarcinoma and squamous cell carcinoma), renal cancer, head and neck cancer, bladder cancer, uterine cancer, esophageal cancer, pancreatic cancer, and glioblastoma multiforme, by administering to a cancer patient a therapeutically effective amount of a herein disclosed FZD10-specific antibody. An amount that, following administration, inhibits, prevents or delays the progression and/or metastasis of a cancer in a statistically significant manner (i.e., relative to an appropriate control as will be known to those skilled in the art) is considered effective.

In certain embodiments, the antibodies described herein bind to FZD10 and block binding of its ligand and subsequent signalling events. Thus, in certain embodiments, the antibodies described herein are useful for the treatment of diseases associated with aberrant expression of ligands for FZD10, such as WNT7a and WNT7b.

Another embodiment provides a method for preventing metastasis of a cancer including, but not limited to, synovial sarcoma, colorectal carcinoma, gastric carcinoma, chronic myeloid leukemia (CML), acute myeloid leukemia (AML), melanoma, salivary carcinomas, breast cancer, hepatocellular carcinoma, ovarian cancer, cervical cancer, colorectal cancers, non-small cell lung cancer (NSCLC; both adenocarcinoma and squamous cell carcinoma), renal cancer, head and neck cancer, bladder cancer, uterine cancer, stomach cancer, esophageal cancer, pancreatic cancer, and glioblastoma multiforme, by administering to a cancer patient a therapeutically effective amount of a herein disclosed FZD10-specific antibody (e.g., an amount that, following administration, inhibits, prevents or delays metastasis of a cancer in a statistically significant manner, i.e., relative to an appropriate control as will be known to those skilled in the art).

Another embodiment provides a method for preventing a cancer including, but not limited to, synovial sarcoma, colorectal carcinoma, gastric carcinoma, melanoma, salivary carcinomas, breast cancer, hepatocellular carcinoma, ovarian cancer, cervical cancer, colorectal cancers, non-small cell lung cancer (NSCLC; both adenocarcinoma and squamous cell carcinoma), renal cancer, head and neck cancer, bladder cancer, uterine cancer, stomach cancer, esophageal cancer, pancreatic cancer, and glioblastoma multiforme, by administering to a cancer patient a therapeutically effective amount of a herein disclosed FZD10-specific antibody.

Another embodiment provides a method for inhibiting canonical Wnt pathway signalling in a cell expressing FZD10 by contacting the cell with an amount of a herein disclosed FZD10-specific antibody sufficient to inhibit signalling via the canonical Wnt pathway.

In certain contemplated embodiments, an FZD10-specific antibody as disclosed herein is the only therapeutically active agent administered to a patient. Alternatively, in certain other embodiments the presently disclosed antibody is administered in combination with one or more other therapeutic agents, including but not limited to cytotoxic agents, chemotherapeutic agents, cytokines, growth inhibitory agents, anti-hormonal agents, anti-inflammatory agents, kinase inhibitors, anti-angiogenic agents, cardioprotectants, or other therapeutic agents. Such molecules are suitably present in combination, in amounts that are effective for the purpose intended. The skilled medical practitioner can determine empirically the appropriate dose or doses of other therapeutic agents useful herein. The antibodies may be administered concomitantly with one or more other therapeutic regimens. For example, an antibody may be administered to the patient along with chemotherapy, radiation therapy, or both chemotherapy and radiation therapy. In one embodiment, the antibody may be administered in conjunction with one or more other antibodies known in the art to provide therapeutic benefit.

In certain contemplated embodiments, the presently described anti-FZD10 antibodies may be administered, simultaneously or sequentially and in any order, with one or more additional WNT inhibitor agent(s). Known antagonists of Wnt signaling include Dickkopf proteins (Dkk-1, -2, and -4), secreted Frizzled-related proteins (sFRP; sFRP-1, 2, and 5, and sFRP-3 and 4), Wnt Inhibitory Factor 1 (WIF-1), Norrin, R-spondin, and DKKL1. Accordingly and as also noted above, in certain such embodiments the additional agent(s) may comprise a second agent that substantially impairs a specific interaction between at least one second Wnt ligand (e.g., a DKK family member such as Dkk-1, Dkk-2 or Dkk-4; a secreted Frizzled-related protein (sFRP) such as sFRP-1, sFRP-2, sFRP-3, sFRP4 or sFRP-5; Wnt Inhibitory Factor 1 (WIF-1); Norrin; R-spondin; DkkL1; etc.) and a second receptor for the Wnt ligand (e.g., FZD1, FZD2, FZD3, FZD4, FZD5, FZD6, FZD7, FZD8, FZD9, LRP5, LRP6, ROR1, ROR2, RYK, MuSK, and a glypican such as glypican3; see, e.g., Schulte 2010 *Pharmacol. Rev.* 62:632; Rao and Kuhl, 2010 *Circ. Res.* 106:1798; Filmus et al., 2008 *Genome Biol.* 9:224; Chien and Moon, 2007 *Front. Biosci.* 12:448; see also Table 1.).

In one embodiment, the presently described antibodies may be administered with a chemotherapeutic agent. By "chemotherapeutic agent" is meant a chemical compound useful in the treatment of cancer. Examples of chemotherapeutic agents include but are not limited to alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.RTM.; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; thymidylate synthase inhibitor (such as Tomudex); cox-2 inhibitors, such as celicoxib (CELEBREX®.) or MK-0966 (VIOXX®); and pharmaceutically acceptable salts, acids or derivatives of any of the above. Also included are anti-hormonal agents that act to regulate or inhibit hormone action on tumors such as anti estrogens including, for example, tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

A chemotherapeutic or other cytotoxic agent may be administered as a prodrug. By "prodrug" as used herein is meant a precursor or derivative form of a pharmaceutically active substance that is less cytotoxic to tumor cells compared to the parent drug and is capable of being enzymatically activated or converted into the more active parent form. See, for example, Wilman, 1986, *Biochem. Soc. Trans.*, 615th Meeting Belfast, 14:375-382; and Stella et al., "Prodrugs: A Chemical Approach to Targeted Drug Delivery," Directed Drug Delivery, Borchardt et al., (ed.): 247-267, Humana Press, 1985. The prodrugs that may find use, along with the herein described FZD10-specific antibodies, in certain presently contemplated embodiments may include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use with the present FZD10-specific antibodies include but are not limited to any of the aforementioned chemotherapeutic agents.

The present FZD10-specific antibodies may be combined with other therapeutic regimens. For example, in one embodiment, the patient to be treated with the antibody may also receive radiation therapy. Radiation therapy can be administered according to protocols commonly employed in the art and known to the skilled artisan. Such therapy includes but is not limited to irradiating exposure to art accepted radioisotopes of cesium, iridium, iodine, or cobalt. The radiation therapy may be whole body irradiation, or may be directed locally to a specific site or tissue in or on the body, such as the lung, bladder, or prostate. Typically, radiation therapy is administered in pulses over a period of time from about 1 to 2 weeks. The radiation therapy may, however, be administered over longer periods of time. For instance, radiation therapy may be administered to patients having head and neck cancer for about 6 to about 7 weeks. Optionally, the radiation therapy may be administered as a single dose or as multiple, sequential doses. The skilled medical practitioner can determine empirically the appropriate dose or doses of radiation therapy useful herein. In accordance with another embodiment, the present FZD10-specific antibodies and one or more other anti-cancer therapies may be employed to treat cancer cells ex vivo. It is contemplated that such ex vivo treatment may be useful in bone marrow transplantation and particularly, autologous bone marrow transplantation. For instance, treatment of cells or tissue(s) containing cancer cells with antibody and one or more other anti-cancer therapies, such as described above, can be employed to deplete or substantially deplete the cancer cells prior to transplantation in a recipient patient. It is of course contemplated that the antibodies described herein can be employed in combination with still other therapeutic techniques such as surgery.

In an alternate embodiment, the herein described antibodies may be administered with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1 alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

A variety of other therapeutic agents may find use for administration with the FZD10-specific antibodies described herein. In one embodiment, the antibody is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, immune selective anti-inlammatory derivatives (imSAIDS) (see e.g., Bao et al. *Neurosci.* 2006 Jul. 7; 140(3):1011-22; Mathison et al. *BMC Immunol.* 2003 Mar. 4; 4:3), methotrexate, sulfasalazine, leflunomide, anti-TNF medications, cyclophosphamide and mycophenolate.

A variety of other therapeutic agents may find use for administration with the FZD10-specific antibodies described herein. In one embodiment, the antibody is administered with an anti-angiogenic agent. By "anti-angiogenic agent" as used herein is meant a compound that blocks, or interferes to some degree, the development of blood vessels. The anti-angiogenic factor may, for instance, be a small molecule or a protein, for example an antibody, or cytokine, that binds to a growth factor or growth factor receptor involved in promoting angiogenesis. The preferred anti-angiogenic factor herein is an antibody that binds to Vascular Endothelial Growth Factor (VEGF). In an alternate embodiment, the antibody is administered with a therapeutic agent that induces or enhances adaptive immune response, for example an antibody that targets CTLA-4. In an alternate embodiment, the antibody is administered with a tyrosine kinase inhibitor. By "tyrosine kinase inhibitor" as used herein is meant a molecule that inhibits to some extent tyrosine kinase activity of a tyrosine kinase. Examples of such inhibitors include but are not limited to quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo [2,3-d]pyrimidines; curcumin (diferuloyl methane, 4,5-bis(4-fluoroanilino)phthalimide); tyrphostines containing nitrothiophene moieties; PD-0183805 (Warner-Lambert); antisense molecules (e.g. those that bind to ErbB-encoding nucleic acid); quinoxalines (U.S. Pat. No. 5,804,396); tryphostins (U.S. Pat. No. 5,804,396); ZD6474 (Astra Zeneca); PTK-787 (Novartis/Schering A G); pan-ErbB inhibitors such as C1-1033 (Pfizer); Affinitac (ISIS 3521; Isis/Lilly); Imatinib mesylate (ST1571, Gleevec®); Novartis); PKI 166 (Novartis); GW2016 (Glaxo SmithKline); C1-1033 (Pfizer); EKB-569 (Wyeth); Semaxinib (Sugen); ZD6474 (AstraZeneca); PTK-787 (Novartis/Schering AG); INC-1-C11 (Imclone); or as described in any of the following patent publications: U.S. Pat. No. 5,804,396; PCT WO 99/09016 (American Cyanimid); PCT WO 98/43960 (American Cyanamid); PCT WO 97/38983 (Warner-Lambert); PCT WO 99/06378 (Warner-Lambert); PCT WO 99/06396 (Warner-Lambert); PCT WO 96/30347 (Pfizer, Inc); PCT WO 96/33978 (AstraZeneca); PCT WO96/3397 (AstraZeneca); PCT WO 96/33980 (AstraZeneca), gefitinib (IRESSA™, ZD1839, AstraZeneca), and OSI-774 (Tarceva®, OSI Pharmaceuticals/Genentech).

In another contemplated embodiment, an FZD10-specific antibody as described herein may be conjugated or operably linked to another therapeutic compound, referred to herein as a conjugate. The conjugate may be a cytotoxic agent, a chemotherapeutic agent, a cytokine, an anti-angiogenic agent, a tyrosine kinase inhibitor, a toxin, a radioisotope, or other therapeutically active agent. Chemotherapeutic agents, cytokines, anti-angiogenic agents, tyrosine kinase inhibitors, and other therapeutic agents have been described above, and all of these aforementioned therapeutic agents may find use as antibody conjugates.

In an alternate embodiment, the antibody is conjugated or operably linked to a toxin, including but not limited to small molecule toxins and enzymatically active toxins of bacterial, fungal, plant or animal origin, including fragments and/or variants thereof. Small molecule toxins include but are not limited to saporin (Kuroda et al., *The Prostate* 70:1286-1294 (2010); Lip et al., 2007 *Molecular Pharmaceutics* 4:241-251; Quadros et al., 2010 *Mol Cancer Ther;* 9(11); 3033-40; Polito L., et al. 2009 *Brit. JI Haematol,* 147, 710-718), calicheamicin, maytansine (U.S. Pat. No. 5,208,020), trichothene, and CC1065. Toxins include but are not limited to RNase, gelonin, enediynes, ricin, abrin, diptheria toxin, cholera toxin, *Pseudomonas* exotoxin (PE40), *Shigella* toxin, *Clostridium perfringens* toxin, and pokeweed antiviral protein.

In certain related embodiments, the antibody may be conjugated to one or more maytansine molecules (e.g., about 1 to about 10 maytansine molecules per antibody molecule). Maytansine may, for example, be converted to May-SS-Me which may be reduced to May-SH3 and reacted with modified antibody (Chari et al., 1992, *Cancer Research* 52: 127-131) to generate a maytansinoid-antibody conjugate. Another conjugate of interest comprises an antibody conjugated to one or more calicheamicin molecules. The calicheamicin family of antibiotics are capable of producing double-stranded DNA breaks at sub-picomolar concentrations. Structural analogues of calicheamicin that may also be used (Hinman et al., 1993, *Cancer Research* 53:3336-3342; Lode et al., 1998, *Cancer Research* 58:2925-2928) (U.S. Pat. Nos. 5,714,586; 5,712,374; 5,264,586; 5,773,001). Dolastatin 10 analogs such as auristatin E (AE) and monomethylauristatin E (MMAE) may find use as conjugates for the presently disclosed antibodies, or variants thereof (Doronina et al., 2003, *Nat Biotechnol* 21(7):778-84; Francisco et al., 2003 *Blood* 102(4):1458-65). Useful enzymatically active toxins include but are not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, PCT WO 93/21232. The present disclosure further contemplates embodiments in which a conjugate or fusion is formed between an FZD10-specific antibody as described herein and a compound with nucleolytic activity, for example a ribonuclease or DNA endonuclease such as a deoxyribonuclease (DNase).

In an alternate embodiment, a herein-disclosed antibody may be conjugated or operably linked to a radioisotope to form a radioconjugate. A variety of radioactive isotopes are available for the production of radioconjugate antibodies. Examples include, but are not limited to $^{90}Y$, $^{123}I$, $^{125}I$, $^{131}Re$, $^{186}Re$, $^{188}Re$, $^{211}At$, and $^{212}Bi$.

Antibodies described herein may in certain other embodiments be conjugated to a therapeutic moiety such as a cytotoxin (e.g., a cytostatic or cytocidal agent), a therapeutic agent or a radioactive element (e.g., alpha-emitters, gamma-emitters, etc.). Cytotoxins or cytotoxic agents include any agent that is detrimental to cells. Examples include paclitaxel/paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. One preferred exemplary cytotoxin is saporin (available from Advanced Targeting Systems, San Diego, Calif.). Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine).

Moreover, an FZD10-specific antibody (including a functional fragment thereof as provided herein such as an antigen-binding fragment) may in certain embodiments be conjugated to therapeutic moieties such as a radioactive materials or macrocyclic chelators useful for conjugating radiometal ions. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4:2483-90; Peterson et al., 1999, Bioconjug. Chem. 10:553; and Zimmerman et al., 1999, Nucl. Med. Biol. 26:943-50.

In yet another embodiment, an antibody may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the antibody is conjugated or operably linked to an enzyme in order to employ Antibody Dependent Enzyme Mediated Prodrug Therapy (ADEPT). ADEPT may be used by conjugating or operably linking the antibody to a prodrug-activating enzyme that converts a prodrug (e.g., a peptidyl chemotherapeutic agent, see PCT WO 81/01145) to an active anti-cancer drug. See, for example, PCT WO 88/07378 and U.S. Pat. No. 4,975,278. The enzyme component of the immunoconjugate useful for ADEPT includes any enzyme capable of acting on a prodrug in such a way so as to convert it into its more active, cytotoxic form. Enzymes that are useful in the method of these and related embodiments include but are not limited to alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuramimidase useful for converting glycosylated prodrugs into free drugs; beta-lactamase useful for converting drugs derivatized with α-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", may be used to convert prodrugs into free active drugs (see, for example, Massey, 1987, *Nature* 328: 457-458). Antibody-abzyme conjugates can be prepared for delivery of the abzyme to a tumor cell population.

Other modifications of the FZD10-specific antibodies described herein are also contemplated. For example, the antibody may be linked to one of a variety of nonproteinaceous polymers, e.g., polyethylene glycol (PEG), polypropylene glycol, polyoxyalkylenes, or copolymers of polyethylene glycol and polypropylene glycol. In another embodiment, the antibodies may be coupled to differentiation inducers or drugs, and derivatives thereof. Exemplary drugs may include, but are not limited to methotrexate, and pyrimidine and purine analogs. Exemplary differentiation inducers may include but are not limited to phorbol esters and butyric acid.

A variety of linkers may find use in certain embodiments of the present invention to generate antibody conjugates. By "linker", "linker sequence", "spacer", "tethering sequence" or grammatical equivalents thereof, herein is meant a molecule or group of molecules (such as a monomer or polymer) that connects two molecules and often serves to place the two molecules in a preferred configuration. A number of strategies may be used to covalently link molecules together. These include, but are not limited to polypeptide linkages between N- and C-termini of proteins or protein domains, linkage via disulfide bonds, and linkage via chemical cross-linking reagents.

In one such embodiment, the linker is a peptide bond, generated by recombinant techniques or peptide synthesis. Choosing a suitable linker for a specific case where two polypeptide chains are to be connected may depend on one or more various parameters, including but not limited to the nature of the two polypeptide chains (e.g., whether they naturally oligomerize), the distance between the N- and the C-termini to be connected if known, and/or the stability of the linker towards proteolysis and oxidation. Furthermore, the linker may contain amino acid residues that provide flexibility. Thus, the linker peptide may predominantly include one or more of the following amino acid residues: Gly, Ser, Ala, or Thr. The linker peptide should have a length that is adequate to link two molecules in such a way that they assume the correct conformation relative to one another so that they retain the desired activity. Suitable lengths for this purpose include at least one and not more than 30 amino acid residues. Preferably, the linker is from about 1 to 30 amino acids in length, with linkers of 1, 2, 3, 4, 5, 6, 7, 8, 9, 10, 11, 12, 13, 14, 15, 16, 17, 18 19 and 20 amino acids in length being preferred.

The amino acid residues selected for inclusion in the linker peptide may desirably exhibit properties that do not interfere significantly with the activity of the polypeptide. Thus, the linker peptide on the whole should not exhibit a charge that would be inconsistent with the activity of the polypeptide, or interfere with internal folding, or form bonds or other interactions with amino acid residues in one or more of the monomers that would seriously impede the binding of receptor monomer domains. Useful linkers include glycine-serine polymers (including, for example, (GS)n, (GSGGS)n (SEQ ID NO:25), (GGGGS)n (SEQ ID NO:26) and (GGGS)n (SEQ ID NO:27), where n is an integer of at least one), glycine-alanine polymers, alanine-serine polymers, and other flexible linkers such as the tether for the shaker potassium channel, and a large variety of other flexible linkers, as will be appreciated by those in the art.

Glycine-serine polymers are preferred in some embodiments, since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies. Suitable linkers may also be identified by screening databases of known three-dimensional structures for naturally occurring motifs that can bridge the gap between two polypeptide chains.

In a preferred embodiment, the linker is not immunogenic when administered in a human patient. Thus linkers may be chosen such that they have low immunogenicity or are thought to have low immunogenicity. For example, a linker may be chosen that exists naturally in a human. In a preferred embodiment the linker has the sequence of the hinge region of an antibody, that is the sequence that links the antibody Fab and Fc regions; alternatively the linker has a sequence that comprises part of the hinge region, or a sequence that is substantially similar to the hinge region of an antibody. Another way of obtaining a suitable linker is by optimizing a simple linker, e.g., (Gly4Ser)n (SEQ ID NO:26), through random mutagenesis. Alternatively, once a suitable polypeptide linker is defined, additional linker polypeptides can be created to select amino acids that more optimally interact with the domains being linked.

Other types of linkers that may be used include artificial polypeptide linkers and inteins. In another embodiment, disulfide bonds are designed to link the two molecules. In another embodiment, linkers are chemical cross-linking agents. For example, a variety of bifunctional protein coupling agents may be used, including but not limited to N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., 1971, *Science* 238:1098.

Chemical linkers may permit chelation of an isotope. For example, Carbon-14-labeled 1-isothiocyanatobenzyl-3-methyldiethylene triaminepentaacetic acid (MX-DTPA) is an exemplary chelating agent for conjugation of radionuclide to the antibody (see PCT WO 94/11026). The linker may be cleavable, facilitating release of the cytotoxic drug in the cell. For example, an acid-labile linker, peptidase-sensitive linker, dimethyl linker or disulfide-containing linker (Chari et al., 1992, *Cancer Research* 52: 127-131) may be used. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use to link the antibodies disclosed herein to a fusion partner, or to link the antibodies to a desired conjugate moiety to form an immunoconjugate.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al. Where a therapeutic agent is more potent when free from the antibody portion of the immunoconjugate, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A therapeutic agent such as a toxin or drug may be coupled (e.g., covalently bonded) to an antibody either directly or indirectly (e.g., via a linker group as disclosed herein). For example, in one embodiment, the therapeutic agent is coupled indirectly via the avidin-biotin system or other similar systems. A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Techniques for conjugating therapeutic moieties to antibodies are well known; see, e.g., Amon et al., "Monoclonal Antibodies For Immunotargeting Of Drugs In Cancer Therapy", in Monoclonal Antibodies And Cancer Therapy, Reisfeld et al. (eds.), 1985, pp. 243-56, Alan R. Liss, Inc.; Hellstrom et al., "Antibodies For Drug Delivery", in Controlled Drug Delivery (2nd Ed.), Robinson et al. (eds.), 1987, pp. 623-53, Marcel Dekker, Inc.; Thorpe, "Antibody Carriers Of Cytotoxic Agents In Cancer Therapy: A Review", in Monoclonal Antibodies '84: Biological And Clinical Applications, Pinchera et al. (eds.), 1985, pp. 475-506; "Analysis, Results, And Future Prospective Of The Therapeutic Use Of Radiolabeled Antibody In Cancer Therapy", in Monoclonal Antibodies For Cancer Detection And Therapy, Baldwin et al. (eds.), 1985, pp. 303-16, Academic Press; and Thorpe et al., *Immunol. Rev.* 62:119-58, 1982.

Administration of the FZD10-specific antibodies described herein, in pure form or in an appropriate pharmaceutical composition, can be carried out via any of the accepted modes of administration of agents for serving similar utilities. The pharmaceutical compositions can be prepared by combining an antibody or antibody-containing composition (e.g., an immunoconjugate such as an FZD10-specific antibody-saporin immunotoxin) with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other anti-cancer agents as described elsewhere herein) and/or suitable excipients such as salts, buffers and stabilizers may, but need not, be present within the composition. Administration may be achieved by a variety of different routes, including oral, parenteral, nasal, intravenous, intradermal, subcutaneous or topical. Preferred modes of administration depend upon the nature of the condition to be treated or prevented. An amount that, following administration, reduces, inhibits, prevents or delays the progression and/or metastasis of a cancer is considered effective.

In certain embodiments, the amount administered is sufficient to result in tumor regression, as indicated by a statistically significant decrease in the amount of viable tumor, for example, at least a 50% decrease in tumor mass, or by altered (e.g., decreased with statistical significance) scan dimensions. The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

The FZD10-specific antibody-containing compositions may be administered alone or in combination with other known cancer treatments, such as radiation therapy, chemotherapy, transplantation, immunotherapy, hormone therapy, photodynamic therapy, etc. The compositions may also be administered in combination with antibiotics used to treat bacterial infections, in particular intracellular bacterial infections.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described FZD10-specific antibody in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of an antibody of the present disclosure, for treatment of a disease or condition of interest in accordance with teachings herein.

A pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of an FZD10-specific antibody as herein disclosed such that a suitable dosage will be obtained. Typically, this amount is at least 0.01% of the antibody in the composition. When intended for oral administration, this amount may be varied to be between 0.1 and about 70% of the weight of the composition. Certain oral pharmaceutical compositions contain between about 4% and about 75% of the antibody. In certain embodiments, pharmaceutical compositions and preparations according to the present invention are prepared so that a parenteral dosage unit contains between 0.01 to 10% by weight of the antibody prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to the antibody of the invention and thereby assists in the delivery of the compound. Suitable agents that may act in this capacity include other monoclonal or polyclonal antibodies, one or more proteins or a liposome. The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions may be prepared by methodology well known in the pharmaceutical art. For example, a pharmaceutical composition intended to be administered by injection can be prepared by combining a composition that comprises a herein-described FZD10-specific antibody and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the antibody composition so as to facilitate dissolution or homogeneous suspension of the antibody in the aqueous delivery system.

The compositions may be administered in a therapeutically effective amount, which will vary depending upon a variety of factors including the activity of the specific compound (e.g., FZD10-specific antibody) employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.07 mg) to about 100 mg/kg (i.e., 7.0 g); preferably a therapeutically effective dose is (for a 70 kg mammal) from about 0.01 mg/kg (i.e., 0.7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g).

Compositions comprising the herein described FZD10-specific antibody may also be administered simultaneously with, prior to, or after administration of one or more other therapeutic agents. Such combination therapy may include administration of a single pharmaceutical dosage formulation which contains a compound of the invention and one or more additional active agents, as well as administration of compositions comprising antibodies of the invention and each active agent in its own separate pharmaceutical dosage formulation. For example, an antibody as described herein and the other active agent can be administered to the patient together in a single oral dosage composition such as a tablet or capsule, or each agent administered in separate oral dosage formulations. Where separate dosage formulations are used, the compositions comprising antibodies and one or more additional active agents can be administered at essentially the same time, i.e., concurrently, or at separately staggered times, i.e., sequentially and in any order; combination therapy is understood to include all these regimens.

The compositions comprising herein described FZD10-specific antibodies may be administered to an individual afflicted with a disease as described herein, such as a cancer. For in vivo use for the treatment of human disease, the antibodies described herein are generally incorporated into a pharmaceutical composition prior to administration. A pharmaceutical composition comprises one or more of the antibodies described herein in combination with a physiologically acceptable carrier or excipient as described elsewhere herein. To prepare a pharmaceutical composition, an effective amount of one or more of the compounds is mixed with any pharmaceutical carrier(s) or excipient known to those skilled in the art to be suitable for the particular mode of administration. A pharmaceutical carrier may be liquid, semi-liquid or solid. Solutions or suspensions used for parenteral, intradermal, subcutaneous or topical application may include, for example, a sterile diluent (such as water), saline solution, fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously, suitable carriers include physiological saline or phosphate buffered saline (PBS), and solutions containing thickening and solubilizing agents, such as glucose, polyethylene glycol, polypropylene glycol and mixtures thereof.

The compositions comprising FZD10-specific antibodies as described herein may be prepared with carriers that protect the antibody against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

Various other embodiments of the present invention relate, in part, to diagnostic applications for detecting the presence of cells or tissues expressing FZD10. Thus, the present disclosure provides methods of detecting FZD10 in a sample, such as detection of cells or tissues expressing FZD10. Such methods can be applied in a variety of known detection formats, including, but not limited to immunohistochemistry (IHC), immunocytochemistry (ICC), in situ hybridization (ISH), whole-mount in situ hybridization (WISH), fluorescent DNA in situ hybridization (FISH), flow cytometry, enzyme immuno-assay (EIA), and enzyme linked immunoassay (ELISA).

ISH is a type of hybridization that uses a labeled complementary DNA or RNA strand (i.e., primary binding agent) to localize a specific DNA or RNA sequence in a portion or section of a cell or tissue (in situ), or if the tissue is small enough, the entire tissue (whole mount ISH). One having ordinary skill in the art would appreciate that this is distinct from immunohistochemistry, which localizes proteins in tissue sections using an antibody as a primary binding agent. DNA ISH can be used on genomic DNA to determine the structure of chromosomes. Fluorescent DNA ISH (FISH) can, for example, be used in medical diagnostics to assess chromosomal integrity. RNA ISH (hybridization histochemistry) is used to measure and localize mRNAs and other transcripts within tissue sections or whole mounts.

In various embodiments, the antibodies described herein are conjugated to a detectable label that may be detected directly or indirectly. In this regard, an antibody "conjugate" refers to an anti-FZD10 antibody that is covalently linked to a detectable label. In the present invention, DNA probes, RNA probes, monoclonal antibodies, antigen-binding fragments thereof, and antibody derivatives thereof, such as a single-chain-variable-fragment antibody or an epitope tagged antibody, may all be covalently linked to a detectable label. In "direct detection", only one detectable antibody is used, i.e., a primary detectable antibody. Thus, direct detection means that the antibody that is conjugated to a detectable label may be detected, per se, without the need for the addition of a second antibody (secondary antibody).

A "detectable label" is a molecule or material that can produce a detectable (such as visually, electronically or otherwise) signal that indicates the presence and/or concentration of the label in a sample. When conjugated to a antibody, the detectable label can be used to locate and/or quantify the target to which the specific antibody is directed. Thereby, the presence and/or concentration of the target in a sample can be detected by detecting the signal produced by the detectable label. A detectable label can be detected directly or indirectly, and several different detectable labels conjugated to different specific-antibodies can be used in combination to detect one or more targets.

Examples of detectable labels, which may be detected directly, include fluorescent dyes and radioactive substances and metal particles. In contrast, indirect detection requires the application of one or more additional antibodies, i.e., secondary antibodies, after application of the primary antibody. Thus, the detection is performed by the detection of the binding of the secondary antibody or binding agent to the primary detectable antibody. Examples of primary detectable binding agents or antibodies requiring addition of a secondary binding agent or antibody include enzymatic detectable binding agents and hapten detectable binding agents or antibodies.

In some embodiments, the detectable label is conjugated to a nucleic acid polymer which comprises the first binding agent (e.g., in an ISH, WISH, or FISH process). In other embodiments, the detectable label is conjugated to an antibody which comprises the first binding agent (e.g., in an IHC process).

Examples of detectable labels which may be conjugated to antibodies used in the methods of the present disclosure include fluorescent labels, enzyme labels, radioisotopes, chemiluminescent labels, electrochemiluminescent labels, bioluminescent labels, polymers, polymer particles, metal particles, haptens, and dyes.

Examples of fluorescent labels include 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeton Red, green fluorescent protein (GFP) and analogues thereof, and conjugates of R-phycoerythrin or allophycoerythrin, inorganic fluorescent labels such as particles based on semiconductor material like coated CdSe nanocrystallites.

Examples of polymer particle labels include micro particles or latex particles of polystyrene, PMMA or silica, which can be embedded with fluorescent dyes, or polymer micelles or capsules which contain dyes, enzymes or substrates.

Examples of metal particle labels include gold particles and coated gold particles, which can be converted by silver stains. Examples of haptens include DNP, fluorescein isothiocyanate (FITC), biotin, and digoxigenin. Examples of enzymatic labels include horseradish peroxidase (HRP), alkaline phosphatase (ALP or AP), β-galactosidase (GAL), glucose-6-phosphate dehydrogenase, β-N-acetylglucosamimidase, β-glucuronidase, invertase, Xanthine Oxidase, firefly luciferase and glucose oxidase (GO). Examples of commonly used substrates for horseradishperoxidase include 3,3'-diaminobenzidine (DAB), diaminobenzidine with nickel enhancement, 3-amino-9-ethylcarbazole (AEC), Benzidine dihydrochloride (BDHC), Hanker-Yates reagent (HYR), Indophane blue (IB), tetramethylbenzidine (TMB), 4-chloro-1-naphtol (CN), .alpha.-naphtol pyronin (.alpha.-NP), o-dianisidine (OD), 5-bromo-4-chloro-3-indolylphosp-hate (BLIP), Nitro blue tetrazolium (NBT), 2-(p-iodophenyl)-3-p-nitropheny-I-5-phenyl tetrazolium chloride (INT), tetranitro blue tetrazolium (TNBT), 5-bromo-4-chloro-3-indoxyl-beta-D-galactoside/ferro-ferricyanide (BCIG/FF).

Examples of commonly used substrates for Alkaline Phosphatase include Naphthol-AS-B 1-phosphate/fast red TR (NABP/FR), Naphthol-AS-MX-phosphate/fast red TR (NAMP/FR), Naphthol-AS-B1-phosphate/-fast red TR (NABP/FR), Naphthol-AS-MX-phosphate/fast red TR(NAMP/FR), Naphthol-AS-B1-phosphate/new fuschin (NABP/NF), bromochloroindolyl phosphate/nitroblue tetrazolium (BCIP/NBT), 5-Bromo-4-chloro-3-indolyl-b-d-galactopyranoside (BCIG).

Examples of luminescent labels include luminol, isoluminol, acridinium esters, 1,2-dioxetanes and pyridopyridazines. Examples of electrochemiluminescent labels include ruthenium derivatives. Examples of radioactive labels include radioactive isotopes of iodide, cobalt, selenium, tritium, carbon, sulfur and phosphorous.

Detectable labels may be linked to the antibodies described herein or to any other molecule that specifically binds to a biological marker of interest, e.g., an antibody, a nucleic acid probe, or a polymer. Furthermore, one of ordinary skill in the art would appreciate that detectable labels can also be conjugated to second, and/or third, and/or fourth, and/or fifth binding agents or antibodies, etc. Moreover, the skilled artisan would appreciate that each additional binding agent or antibody used to characterize a biological marker of interest may serve as a signal amplification step. The biological marker may be detected visually using, e.g., light microscopy, fluorescent microscopy, electron microscopy where the detectable substance is for example a dye, a colloidal gold particle, a luminescent reagent. Visually detectable substances bound to a biological marker may also be detected using a spectrophotometer. Where the detectable substance is a radioactive isotope detection can be visually by autoradiography, or non-visually using a scintillation counter. See, e.g., Larsson, 1988, Immunocytochemistry: Theory and Practice, (CRC Press, Boca Raton, Fla.); Methods in Molecular Biology, vol. 80 1998, John D. Pound (ed.) (Humana Press, Totowa, N.J.).

Certain embodiments provide kits for detecting FZD10 or cells or tissues expressing FZD10 in a sample, wherein the kits contain at least one antibody, polypeptide, polynucleotide, vector or host cell as described herein. In certain embodiments, a kit may comprise buffers, enzymes, labels, substrates, beads or other surfaces to which the antibodies of the invention are attached, and the like, and instructions for use.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

As used herein the singular forms "a", "an" and "the" include plural aspects unless the context clearly dictates otherwise. Thus, for example, reference to "a cell" includes a single cell, as well as two or more cells; reference to "an agent" includes one agent, as well as two or more agents; and so forth.

Each embodiment described in this specification is to be applied mutatis mutandis to every other embodiment unless expressly stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references in microbiology, molecular biology, biochemistry, molecular genetics, cell biology, virology and immunology techniques that are cited and discussed throughout the present specification. See, e.g., Sambrook, et al., *Molecular Cloning: A Laboratory Manual*, 3d ed., 2001, Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, N.Y.); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid Hybridization* (B. Flames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols (Methods in Molecular Biology)* (Park, Ed., 3$^{rd}$ Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and CC Blackwell, eds., 1986); Riott, *Essential Immunology*, 6th Edition, (Blackwell Scientific Publications, Oxford, 1988); *Embryonic Stem Cells: Methods and Protocols (Methods in Molecular Biology)* (Kurstad Turksen, Ed., 2002); *Embryonic Stem Cell Protocols: Volume I: Isolation and Characterization* (Methods in Molecular Biology) (Kurstad Turksen, Ed., 2006); *Embryonic Stem Cell Protocols: Volume II: Differentiation Models* (Methods in Molecular Biology) (Kurstad Turksen, Ed., 2006); *Human Embryonic Stem Cell Protocols* (Methods in Molecular Biology) (Kursad Turksen Ed., 2006); *Mesenchymal Stem Cells: Methods and Protocols* (Methods in Molecular Biology) (Darwin J. Prockop, Donald G. Phinney, and Bruce A. Bunnell Eds., 2008); *Hematopoietic Stem Cell Protocols* (Methods in Molecular Medicine) (Christopher A. Klug, and Craig T. Jordan Eds., 2001); *Hematopoietic Stem Cell Protocols* (Methods in Molecular Biology) (Kevin D. Bunting Ed., 2008) *Neural Stem Cells: Methods and Protocols* (Methods in Molecular Biology) (Leslie P. Weiner Ed., 2008).

Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

Unless the context requires otherwise, throughout the present specification and claims, the word "comprise" and variations thereof, such as, "comprises" and "comprising" are to be construed in an open, inclusive sense, that is, as "including, but not limited to". By "consisting of is meant including, and typically limited to, whatever follows the phrase "consisting of:" By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are required and may or may not be present depending upon whether or not they affect the activity or action of the listed elements.

In this specification and the appended claims, the singular forms "a," "an" and "the" include plural references unless the content clearly dictates otherwise. As used herein, in particular embodiments, the terms "about" or "approximately" when preceding a numerical value indicates the value plus or minus a range of 5%, 6%, 7%, 8% or 9%. In other embodiments, the terms "about" or "approximately" when preceding a numerical value indicates the value plus or minus a range of 10%, 11%, 12%, 13% or 14%. In yet other embodiments, the terms "about" or "approximately" when preceding a numerical value indicates the value plus or minus a range of 15%, 16%, 17%, 18%, 19% or 20%.

Reference throughout this specification to "one embodiment" or "an embodiment" or "an aspect" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

EXAMPLES

Example 1

Generation of FZD10-Specific Antibodies Using Ex Vivo Diversification System

The DT40 chicken B cell lymphoma line has been shown to be a promising starting point for antibody evolution ex vivo (Cumbers, S. J. et al. *Nat Biotechnol* 20, 1129-1134 (2002); Seo, H. et al. *Nat Biotechnol* 23, 731-735 (2005)). DT40 cells proliferate robustly in culture, with an 8-10 hour doubling time (compared to 20-24 hr for human B cell lines), and they support very efficient homologous gene targeting (Buerstedde, J. M. et al. *Embo J* 9, 921-927 (1990)). DT40 cells command enormous potential V region sequence diversity, as they can access two distinct physiological pathways for diversification, gene conversion and somatic hypermutation, which create templated and nontemplated mutations, respectively (Maizels, N. *Annu Rev Genet* 39, 23-46 (2005)). However, utility of DT40 cells for antibody evolution has been limited in practice because—as in other transformed B cell lines—diversification occurs at less than 1% the physiological rate. Diversification can be accelerated several-fold by disabling the homologous recombination pathway (Cumbers, S. J. et al. Supra), but cells thus engineered have lost ability to carry out efficient gene targeting. Diversification can also be accelerated by treatment of cells with the histone deacetylase inhibitor, trichostatin A (Seo et al., Supra), but resulting mutations are exclusively templated, which limits potential diversity and may not produce antibodies of required affinity or specificity.

In this Example, DT40 cells were engineered to create a highly diverse primary repertoire and to accelerate the rate of Ig gene diversification within the cell without sacrificing the capacity for further genetic modification or the potential for both gene conversion and somatic hypermutation to contribute to mutagenesis. This was accomplished by putting Ig gene diversification under control of the potent *E. coli* lactose operator/repressor regulatory network. As demonstrated here, these engineered cells not only accelerated diversification, but allowed for the experimental regulation of diversification pathways to control diverging mutations from the primary repertoire and affinity/functional antibody maturation.

Multimers consisting of approximately 100 polymerized repeats of the potent *E. coli* lactose operator (PolyLacO) were inserted upstream of the rearranged and expressed Igλ and IgH genes by homologous gene targeting. Regulatory factors fused to lactose repressor protein (LacI) can then be tethered to the LacO regulatory elements to regulate diversification, taking advantage of the high affinity ($k_D = 10^{-14}$ M) of lactose repressor for operator DNA. DT40 PolyLacO-$\lambda_R$ cells, in which PolyLacO was integrated only at Igλ, exhibited a 5-fold increase in Ig gene diversification rate relative to the parental DT40 cells prior to any engineering (Cummings, W. J. et al. *PLoS Biol* 5, e246 (2007)). Diversification was predicted to be further elevated in cells engineered to carry PolyLacO targeted to both the Igλ and the IgH genes ("DTLacO"). This was confirmed for candidate engineered lines by assaying the fraction of sIgM⁻ cells 3 weeks post-transfection with the LacI-HP1 regulatory factor, which showed that diversification rates were 2.5- to 9.2-fold elevated relative to the 2.8% characteristic of the parental DT40 PolyLacO-$\lambda_R$ LacI-HP1 line. Acceleration was reconfirmed for one line by fluctuation assay of individual transfectants. Percentages of sIgM⁻ cells ranged from 2.5% to 52.5%, with a median of 13.0% in the DTLacO cells. This median value is 4.7-fold higher than in DT40 PolyLacO-$\lambda_R$ LacI-HP1 transfectants (2.8%), and 21.7-fold higher than in control cells (DT40 PolyLacO-$\lambda_R$ GFP-LacI (0.6%), comparable to the DT40 parental line (Cummings, W. J. et al. *PLoS Biol* 5, e246 (2007)). Some individual clones exhibited diversification rates considerably different than the median, as predicted because this fluctuation assay measures accumulated sIgM-loss variants (Luria, S. E. & Delbruck, M. *Genetics* 28, 492-511 (1943)). Thus, targeting PolyLacO elements to both the heavy and light chain genes accelerated diversification 21.7-fold relative to the DT40 parental cell line.

The cell surface receptor FZD10 is a G protein-coupled receptor for WNT7a and WNT7b. There is 93% amino acid sequence identity between mouse and human FZD10 polypeptides. In normal tissues, the expression of this protein is very low or absent in vital organs; it is present at low levels in superficial mucosa of stomach and colon, proximal and distal tubules of kidney, endometrial stroma, and placenta. It has been shown to be expressed in various cancers, such as synovial sarcoma (92%; Nagayama et al., 2002 *Cancer Res.* 62:5859), gastric carcinoma (40%; Kirikoshi et al., 2001 *Int. J. Oncol.* 19:767) and colorectal carcinoma (25%; Nagayama et al., 2009 *Cancer Sci.* 100:405). Specific siRNA knockdown of FZD10 expression resulted in synovial sarcoma cell growth inhibition in vitro, and polyclonal anti-FZD10 antibodies were shown to mediate ADCC against FZD10-overexpressing synovial sarcoma cells in vitro, and to inhibit synovial sarcoma xenograft tumor growth in vivo. (Nagayama et al., 2005 *Oncogene* 24:6201). A radiolabeled anti-FZD10 monoclonal antibody was internalized by antigen-bearing tumor cells and dramatically suppressed synovial sarcoma xenograft tumor growth in vivo. (Fukukawa et al., 2008 *Cancer Sci.* 99:437).

The engineered DTLacO line, which carried PolyLacO at both the heavy and light chain genes, had the capacity to rapidly diversify the heavy and light chain V regions when transfected with various LacI-regulatory fusion proteins. This diverse DTLacO population was then used as the starting point for antibody discovery ex vivo. A schematic showing the anti-FZD10 antibody selection and maturation strategy is shown in FIG. 1. The extracellular N-terminal domain of FZD10 fused to human IgG Fc (R&D Systems) was used to interrogate the DTLacO cells for FZD10-specific binding.

The following methods were used in this Example.

Cell Culture and Gene Targeting. Cell lines were purchased from ATCC unless otherwise indicated. DT40-derived cell lines were maintained and transfected as previously described (Yabuki, M., Fujii, M. M. & Maizels, N. *Nat Immunol* 6, 730-736 (2005)), and other cell lines as specified by the source of origin. The PolyLacO regulatory element (Robinett, C. C. et al. *J Cell Biol* 135, 1685-1700 (1996)), consisting of approximately 100 repeats of the lactose operator (LacO), was targeted to the rearranged and expressed heavy chain allele of DT40 PolyLacO-$\lambda_R$ cells, previously engineered to carry PolyLacO at the rearranged and expressed light chain allele (Cummings, W. J. et al. *PLoS Biol* 5, e246 (2007).; Yabuki, M., Ordinario, E. C., Cummings, W. J., Fujii, M. M. & Maizels, N. *J Immunol* 182, 408-415 (2009); Cummings, W. J., Bednarski, D. W. & Maizels, N. *PLoS ONE* 3, e4075 (2008)). Gene targeting was carried out as described (Yabuki et al., Supra), using the targeting construct, pPolyLacO-$\phi V_H$. To generate this construct, a 4-kb fragment from the $\phi V_H$ array was amplified from DT40 genomic DNA, cloned into the BglII-BamHI site of pSV40/Zeo2 vector (Invitrogen), and PolyLacO and histidinol-resistance marker fragments were inserted into the $\phi V_H$ fragment. The construct was verified by restriction analyses, PCR, and partial sequencing, and propagated in recombination-deficient *E. coli* strains Stbl2 (Invitrogen) to maintain repeat stability. Following transfection of DT40 PolyLacO-$\lambda_R$ cells, stable transfectants were selected and screened by PCR and Southern blotting. The loxP-flanked selection marker was deleted by transient expression of Cre recombinase, and accelerated diversification was tested in cells stably transfected with LacI-HP1 (Cummings, et al. 2007 Supra). DTLacO cells stably expressing LacI-HP1 or E47-LacI (Yabuki et al., Supra) were used for selection of antigen-specific lineages.

Antigens and Selection for Antigen Binding. Initial selections were performed by binding diversified DTLacO populations to beads complexed with antigen; and subsequent selections by FACS, using fluorescence-labeled soluble antigen (Cumbers et al. and Seo et al., supra). To select cells that recognized FZD10, the antigen used was recombinant human FZD10-Fc fusion protein bound to Dynal magnetic Protein G beads or detected with PECy5-labeled anti-human IgG(Fc).

Binding, Affinity and Functionality Assays. Recombinant antibodies were generated by cloning PCR-amplified V regions (Cummings et al., 2007 Supra) into a vector that supported expression of human IgG1 in 293F cells. Saturation binding kinetics were determined by either staining FZD10-specific DTLacO cells with various concentrations of fluorescent-labeled soluble antigen, or by staining FZD10-transfected cells or cancer cell lines intrinsically expressing FZD10 with various concentrations of the recombinant chimeric anti-FZD10 mAbs. To assay cell surface FZD10 binding, cells were stained with chimeric mAb clones B9A5 (parent), B9L32.2 and B9L9.3 (progeny) or secondary antibody alone, all at concentrations ranging from 3 µM to 800 nM, and analyzed by immunocytofluorimetry.

Figure 2:
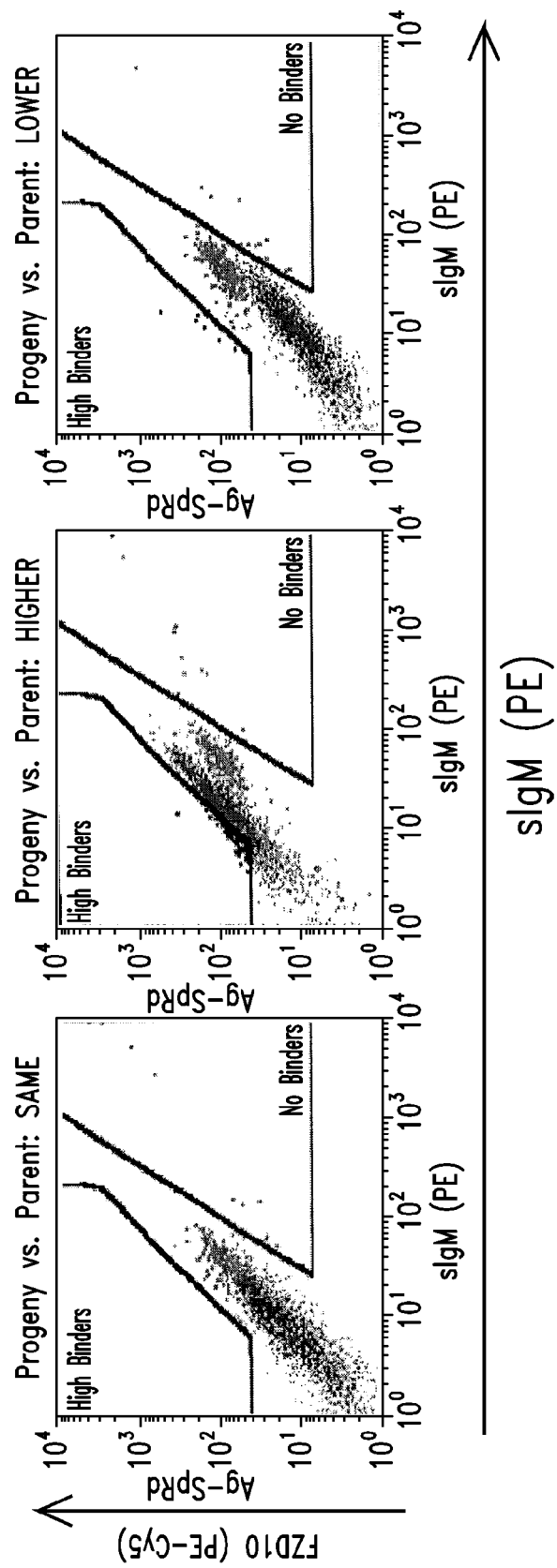
FIG. 2 is a series of dot plots showing the selection strategy for high affinity anti-FZD10 antibody progeny clones during the affinity maturation process.

In the antibody discovery scheme as shown in FIG. 1, diversified DTLacO clones were identified that had greater affinity than that of the parent clone. Keeping in mind that elevated surface IgM in any given clone can be misleading by implying higher affinity binding, the strategy to identify clones with greater affinity than the parent clone was to double stain with labeled target and anti-IgM, and select clones with higher target staining relative to starting parental DTLacO; clones with higher surface IgM staining were avoided. This selection strategy is shown in FIG. 2.

Figures 3A, 3B, 3C:
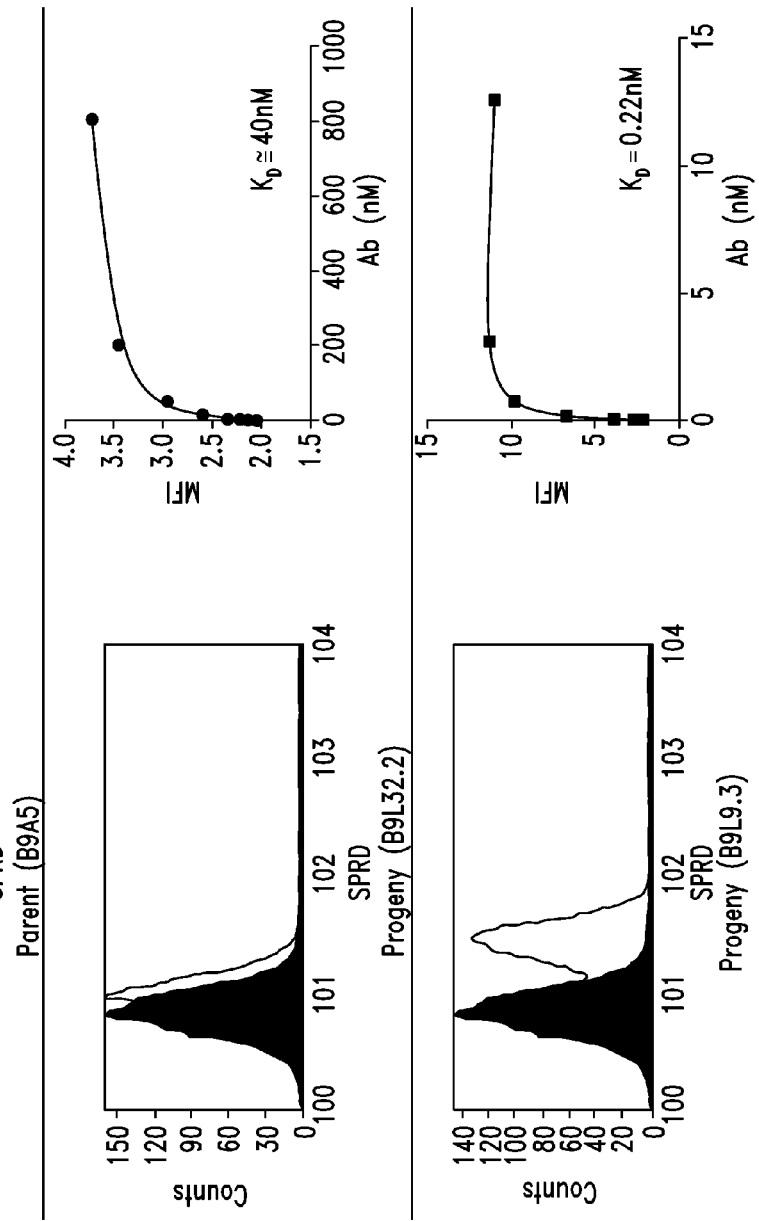
FIG. 3, panels A, B and C, are histograms showing high affinity anti-FZD10 antibody binding to synovial sarcoma cells expressing FZD10. The histograms show binding by anti-FZD10 antibodies produced by two progeny clones as compared to the antibody produced by the related parent clone. Panel A: parent antibody B9A5; panel B: progeny clone B9L32.2 with $K_D$ of 40 nM; panel C: progeny clone B9L9.3 with $K_D$ of 0.22 nM.

The DTLacO screening and selection strategy identified the parent clone, B9A5, and 2 high affinity binding progeny clones, B9L32.2 and B9L9.3. Both progeny clones demonstrated higher affinity binding to the FZD10+ synovial sarcoma cell line, SYO-1. The $K_D$ of B9L32.2 and B9L9.3 binding to the SYO-1 cells was 40 nM and 0.22 nm, respectively (see FIG. 3).

B9A5, B9L32.2 and B9L9.3 clones were sequenced and cloned to generate chimeric antibodies used for further functional characterization. The amino acid sequence for B9A5 heavy and light chain are provided in SEQ ID NOs:1 and 2, respectively. The amino acid sequence for B9L9.3 heavy and light chain are provided in SEQ ID NOs:1 and 3, respectively. The amino acid sequence for B9L32.2 heavy and light chain are provided in SEQ ID NOs:1 and 4, respectively.

The alignment of the heavy and light chain sequences of the B9 parent and progeny clones in FIG. 4 showed that all three antibodies had the same heavy chain sequence but had distinct light chain CDR1 region sequences.

Example 2

Anti-FZD10 mAb-Toxin Conjugates are Lethal to Cells Expressing FZD10

The ribosome-inactivating protein, saporin (molecular weight 30 kDa), is toxic to tumor cells when delivered by an antibody that is internalized (see e.g., Flavell, D. J. et al. *British J Cancer* 83, 1755-1761 (2000); Yip, W. L. et al. *Mol Pharmaceutics* 4, 241-251 (2007); Daniels, T. R. et al. *Mol Cancer Ther* 6, 2995-3008 (2007); Kuroda, K et al. *Prostate* 70, 1286-1294 (2010)). A chemical conjugate of streptavidin and saporin (Streptavidin-ZAP) was purchased from Advanced Targeting Systems (San Diego, Calif.). A B9L9.3-saporin conjugate was generated by the following procedure: B9L9.3 was biotinylated using EZ-Link Sulfo-NHS-LC-Biotinylation Kit (Thermo Fisher Scientific, Rockford, Ill.) in accordance with the manufacturer's instruction. Streptavidin-ZAP was linked to biotinylated B9L9.3 by incubating the components at room temperature for 30 min at a 1:1 molar ratio. As a negative isotype control, a chimeric antibody specific for human VEGFR2 was similarly conjugated with streptavidin-ZAP and applied to the assays described below.

Figure 5:
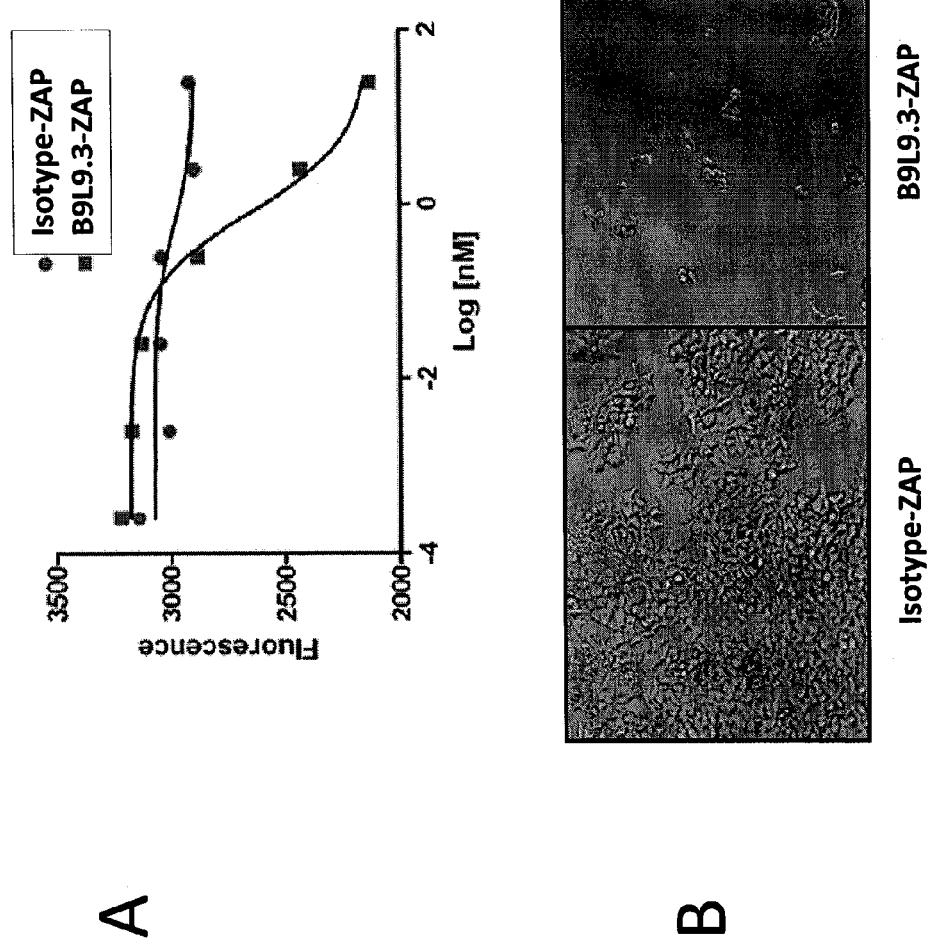
FIG. 5, panels A and B show that anti-FZD10 B9L9.3 mAb-saporin conjugates were lethal to cells expressing FZD10. Panel A is a graph showing cell viability following exposure to increasing concentrations of conjugated antibody. Panel B is a photomicrograph showing the cells exposed to the B9L9.3 mAb-saporin conjugate (right) compared to cells exposed to an isotype-matched control mAb saporin conjugate (left) of irrelevant antibody specificity.

To test the targeted toxicity of B9L9.3-saporin, the conjugate was added to 293-FZD10 expressing cells at varying concentrations and cell viability determined. Briefly, cells were seeded into each well of a 96-well tissue culture plate. After an overnight incubation, the cells were washed twice with culture medium. Subsequently, varying concentrations of B9L9.3-Saporin or the isotype control in culture medium were added into triplicate wells and the plate was incubated for 72 hours at 37° C., 5% $CO_2$. For a quantitative assessment of cell survival, relative viability was assayed with a MultiTox Glo kit (Promega). As shown in FIG. 5, the B9L9.3-saporin conjugated antibody effectively killed cells expressing FZD10, with an $IC_{50}$ of 0.8 nM.

Example 3

Anti-FZD10 mAb Kills Tumor Cells by ADCC

Figure 6:
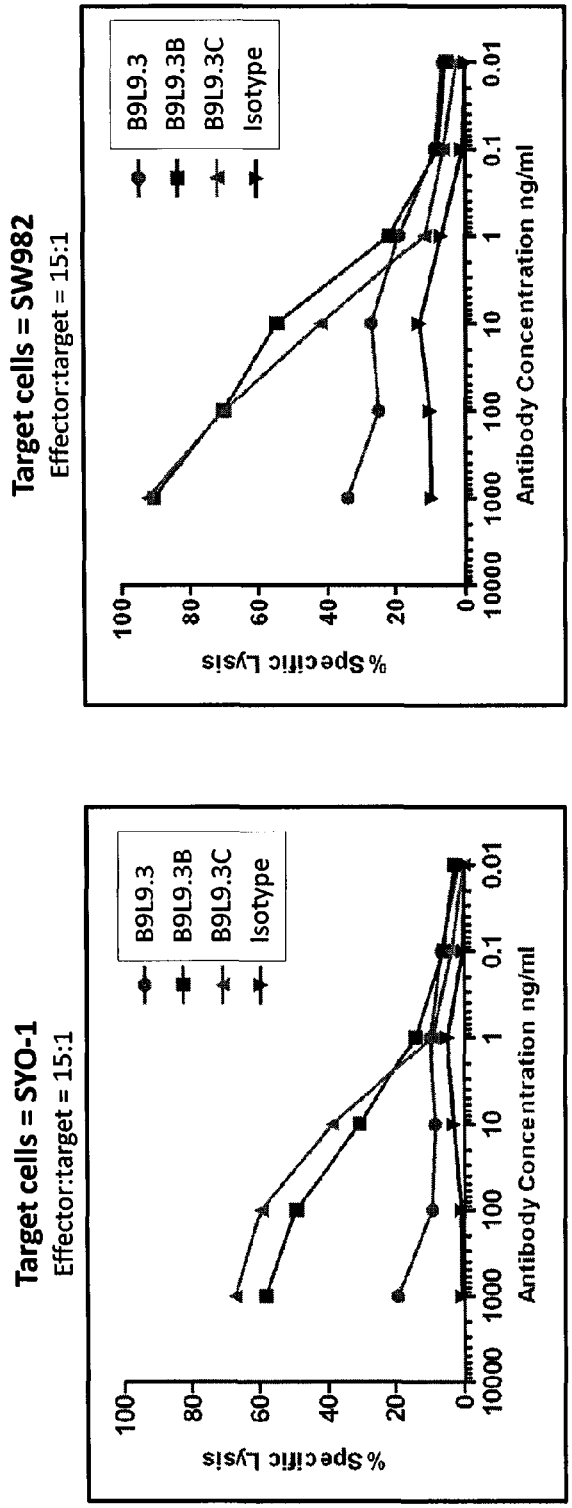
FIG. 6 shows cell lysis curves demonstrating that the B9L9.3 anti-FZD10 mAb killed two synovial sarcoma cell lines by ADCC. Additionally, B9L9.3 anti-FZD10 mAb with an optimized Fc domain demonstrated enhanced killing.

Further experiments showed that the B9L9.3 FZD10-specific antibody killed cancer cells via ADCC. Two synovial sarcoma cell lines were tested. SYO-1 cells were a kind gift of Dr. Akira Kawai (National Cancer Center, Tokyo, Japan). A small subset of the SW982 cell population purchased from ATCC (HTB-93) expressed FZD10, as determined by staining of the cells with B9L9.3 and detecting by flow cytofluorimetry. The FZD10$^+$ population was isolated by FACS, propagated in vitro, and used in subsequent experiments. To assay ADCC, the SYO-1 and FZD10$^+$ SW982 cells as noted in FIG. 6 were incubated with indicated concentrations of mAb B9L9.3 or the isotype control antibody, followed by incubation with total peripheral blood mononuclear cells (effector:target ratio 15:1), and the percent specific lysis was determined by BATDA (bis(acetoxymethyl) 2,2':6'2"-terpyridine-6,6"-dicarboxylate) release (Delfia EuTDA; Perkin Elmer) from the cancer cells. Two variants of the antibody, having either two (see Lazar et al., 2006. *PNAS* 103:4005) or five (see Stavenhagen et al., 2007. *Cancer Res.* 67:8882) amino acid substitutions in the Fc region of the antibody, were found to enhance ADCC.

Example 4

Anti-FZD10 mAb B9L9.3 Inhibits Canonical Wnt Pathway Signaling

Experiments were conducted to determine the effects of the B9L9.3 anti-FZD10 mAb on the canonical Wnt pathway signaling (see e.g., Katoh, 2007 *Stem Cell Rev.* 3:30 for review of the Wnt pathway signaling). The experimental strategy using the TOP/FOPflash luciferase system is outlined in FIG. 7A. 293 FreeStyle cells (Invitrogen) stably expressing FZD10 were transiently transfected with the FZD10 ligand, WNT7b, the coreceptor LRP5, and either the TOPflash or FOPflash TCF reporter plasmid (Millipore). Recombinant mAbs were then added to a final concentration of 20 μg/mL. After 24 hours at 37° C., luciferase activity was assayed in triplicate with the Bright-Glo Luciferase Assay System (Promega). As shown in FIG. 7B, mAb B9L9.3 effectively blocked canonical Wnt pathway signaling.

Example 5

Humanization of Anti-FZD10 mAb B9L9.3

The B9L9.3 chimeric antibody was humanized using the CDR grafting approach first described for humanization of a mouse antibody (Queen C, et al. *Proc Natl Acad Sci USA*. (1989) December; 86(24):10029-33) and recently reviewed by Tsurushita and Vasquez (2004) and Almagro and Fransson (2008) (Tsurushita N, et al., *J Immunol Methods*. 2004 December; 295(1-2):9-19; Almagro J C, and Fransson J. *Front Biosci*. (2008) 13:1619-33).

Consensus human framework sequences were chosen for both the VH and VL of B9L9.3, and in both cases were the subgroup consensus sequence with the highest level of identity to the corresponding B9L9.3 variable region sequence. To humanize the VH of B9L9.3, a consensus sequence of human subgroup III VH sequences (Kabat E A, et al. (1991)) *Sequences of Proteins of Immunological Interest*, Fifth Edition. NIH Publication No. 91-3242) was chosen as the acceptor framework sequence. To humanize the VL of B9L9.3, a consensus sequence of human subgroup III lambda variable sequences (Kabat et al., supra) was chosen as the acceptor framework. However, a simple grafting of CDRs into an acceptor framework usually results in reduced affinity for ligand, suggesting the desirability of replacing one or more residues in the framework sequence with the amino acid found at that position in the original antibody. In particular, residues within the framework sequence that potentially contact antigen or alter the conformation of a neighboring CDR ("Vernier zone" residues) often may be beneficially reverted to the original residue to retain full affinity for ligand (Foote, J and Winter, G. *J Mol Biol*. (1992) 224:487-99). Accordingly, all residues comprising the Vernier zone residues in the B9L9.3 were made identical to those residues found in the original B9L9.3 antibody. Thus, the human residue at each of positions 49, 67, and 94 in humanized VH was changed to the residue found in B9L9.3, while similar human-to-chicken replacements were also made at positions 46, 47, 66, 69 and 71 in humanized VL (Kabat numbering system, Kabat et al., supra).

Figure 9:
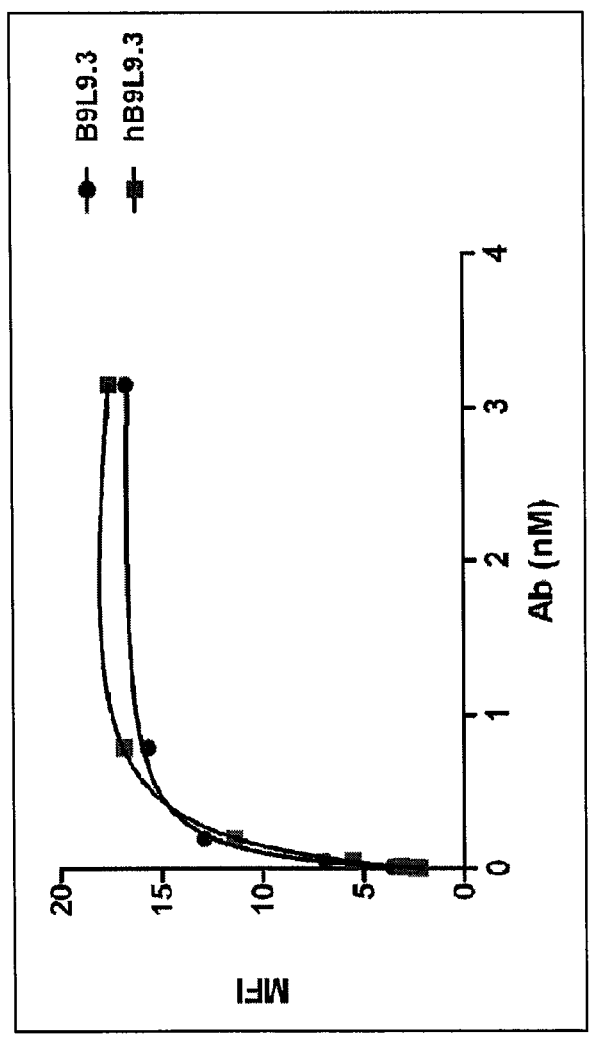
FIG. 9 shows a graph of binding affinity for B9L9.3 and the humanized B9L9.3 antibody hB9L9.3. Affinity was determined by measuring saturation binding kinetics of the recombinant antibodies on SYO-1 cells.

Chicken lambda light chains lack the two amino-terminal residues found in human lambda light chains at positions 1 and 2 (Kabat numbering). Furthermore, the N-terminus of light chains in mammalian antibodies is proximal to L-CDR1. Thus, it seemed possible that the additional two residues at the N-terminus of humanized VL might interfere with antigen binding through steric interference. Therefore, these two amino acids were deleted in the humanized light chain. As shown in Table 2, the resulting humanized antibody had an affinity very close to that of the original chimeric antibody B9L9.3 (also see FIG. 9).

TABLE 2

| Binding affinity of humanized B9L9.3 antibodies | |
|---|---|
| Antibody | Affinity ($K_D$) |
| Chimeric B9L9.3 | 0.16 nM |
| Humanized B9L9.3 | 0.22 nM |

Figure 10:
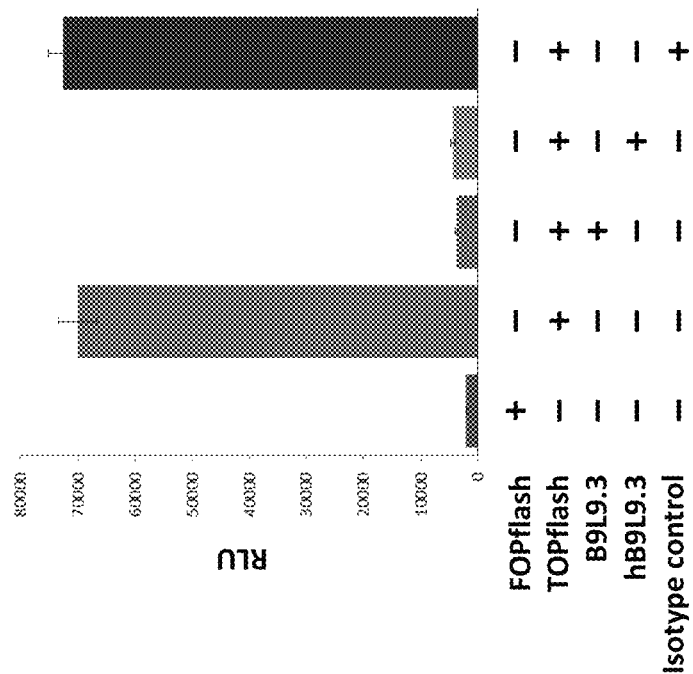
FIG. 10 shows the results of an experiment demonstrating that the humanized B9L9.3 (hB9L9.3) antibody inhibited the canonical Wnt signaling pathway as effectively as the chimeric B9L9.3 antibody.

The capacity of the humanized B9L9.3 mAb to inhibit canonical Wnt pathway signaling was compared with that of the chimeric B9L9.3 mAb. Experimental methods were as described in Example 4, except that the Dual-Glo™ rather than the Bright-Glo™ Luciferase Assay System (Promega) was used to measure luciferase activity. As shown in FIG. 10, the humanized mAb was as effective as its chimeric precursor in blocking the canonical Wnt pathway.

The polynucleotide sequence for humanized heavy chain of B9L9.3 (including the leader sequence) is provided in SEQ ID NO:32, and encoded the mature amino acid sequence provided in SEQ ID NO:31. The polynucleotide sequence encoding humanized light chain of B9L9.3 is provided in SEQ ID NO:30 (including the leader sequence), and encoded the mature amino acid sequence provided in SEQ ID NO:29. The framework sequence of humanized B9L9.3 light chain is 94% human. The framework sequence of humanized B9L9.3 heavy chain is 96% human (see FIG. 8).

In summary, the results from the experiments described in Examples 1-5 demonstrated that the anti-FZD10 mAbs exemplified the dramatic effectiveness of antibody affinity and functional maturation in DTLacO cells. The process allowed affinity maturation from no cell binding to 0.22 nM in two months, a significant improvement over other known methods for generating therapeutic antibodies; the B9L9.3 mAb bound the synovial sarcoma cell lines, SYO-1 and SW-982. The B9L9.3 mAb killed target cells by ADCC and as an antibody-toxin conjugate; the mAb B9L9.3 also blocked canonical Wnt pathway signaling. Additional experiments showed that the B9L32.2 mAb also bound to the synovial sarcoma cell lines, SYO-1 and SW-982. Thus, these antibodies exhibited therapeutic utility for the treatment of diseases associated with aberrant expression of FZD10.

Example 6

Anti-FZD10-Mediated Inhibition of Cancer

The herein described anti-FZD10 antibodies are tested for their ability to inhibit one or more of survival, replication, differentiation, and dedifferentiation (epithelial-to-mesenchymal cell transition) of an FZD10-overexpressing cell, and to inhibit tumor propagation by an isolated FZD10-overexpressing cell, according to established methodologies. See, e.g., Park et al., 2009 *Molec. Therap.* 17:219; Curtin et al., 2010 *Oncotarget* 1:563; De Almeida et al., 2007 *Canc. Res.* 67:5371; Ettenberg et al., 2010 *Proc. Nat. Acad. Sci. USA* 107:15473; Fukukawa et al., 2009 *Oncogene* 28:1110; Fukukawa et al., 2008 *Canc. Sci.* 99:432; He et al., 2004 *Neoplasia* 6:7; Hu et al., 2009 *Canc. Res.* 69:6951; Nagayama et al., 2009 *Canc. Sci.* 100:405; Hagayama et al., 2005 *Oncogene* 24:6201; Nagayama et al., 2002 *Canc. Res.* 62:5859; Pode et al., 2011 *Oncogene* 30:1664; You et al., 2004 *Canc. Res.* 64:56385

Inhibition of FZD10+ Cell Tumor Propagation and Cell Replication in a Xenograft Model: Typically, and depending on the particular FZD10-overexpressing cells being used, xenografts of about $10^2$ to $10^7$ FZD10+ cells are introduced into immunocompromised adoptive hosts and the effects of anti-FZD10 antibody therapy are determined.

In one example, $5\times10^6$ SYO-1 human synovial sarcoma FZD10$^+$ cells (Fukukawa 2008; Hanaoka et al., 2009 *Ann. Nucl. Med.* 23:479; Kawai et al., 2004 *Canc. Lett.* 204:105) or human FZD10$^+$ teratoma cells (PA-1, NTera-2, Tera-2, De Almeida et al., 2007 *Canc. Res.* 67:5371; Snow et al., 2009 *BMC Canc.* 9:383) or FZD10$^+$ non-small cell lung carcinoma cells (NSCLC, Gugger et al., 2008 *Dis. Markers* 24:41) or FZD10$^+$ colorectal cancer cells (SW480, Nagayama et al., 2009 *Cancer Sci.* 100:405) or FZD10$^+$ gastric cancer cells (TMK1, MKN74. Kirikoshi et al., 2001 *Int. J. Oncol.* 19:767) are engrafted by subcutaneous injection into immunodeficient mice (Balb/c nu/nu) and tumor diameters are measured daily with engineer's calipers; the measurements are used to calculate tumor volume (Nagayama et al., 2005 *Oncogene* 24:6201).

Animals having established tumors (volumes of 0.016-1.3 cm$^3$) are randomly assigned to treatment groups that receive a single intravenous injection of anti-FZD10 antibody (15 mg/kg), $^{90}$Y-conjugated anti-FZD10 antibody, or an isotype-matched control antibody having irrelevant binding specificity (anti-CD20). Other experimental groups of animals receive unlabeled anti-FZD10 antibody and an unlabeled anti-LRP6 antibody (Ettenberg et al., 2010 *Proc. Nat. Acad. Sci. USA* 107:15473). The effects on tumor volume are determined by daily measurement of tumor diameters for 60 days.

Inhibition of FZD10$^+$ Cell Survival. The ability of the herein described anti-FZD10 antibodies to induce apoptosis in FZD10$^+$ cells is tested using the procedures essentially as described by He et al. (2004 *Neoplasia* 6:7), Pode-Shakked et al. (2011 *Oncogene* 30:1664) and You et al. (2004 *Canc. Res.* 64:5385). Test cells include SYO-1 human synovial sarcoma FZD10$^+$ cells (Fukukawa 2008; Hanaoka et al., 2009 *Ann. Nucl. Med.* 23:479; Kawai et al., 2004 *Canc. Lett.* 204:105), human FZD10$^+$ teratoma cells (PA-1, NTera-2, Tera-2, De Almeida et al., 2007 *Canc. Res.* 67:5371; Snow et al., 2009 *BMC Canc.* 9:383), FZD10+ non-small cell lung carcinoma cells (NSCLC, Gugger et al., 2008 *Dis. Markers* 24:41), FZD10$^+$ colorectal cancer cells (SW480, Nagayama et al., 2009 *Cancer Sci.* 100:405) and FZD10$^+$ gastric cancer cells (TMK1, MKN74. Kirikoshi et al., 2001 *Int. J. Oncol.* 19:767. Test conditions include contacting the FZD10$^+$ cells with anti-FZD10 antibodies alone or in combination with inhibitors of other Wnt ligand-receptor interactions (e.g., anti-LRP6; Ettenberg et al. 2010); control conditions include contacting the cells with an isotype-matched control antibody of irrelevant specificity or with no antibody.

Dedifferentiation/Epithelial-to-Mesenchymal Transition: The transcriptional activator beta-catenin accumulates in the nuclei of tumor cells undergoing the dedifferentiative process of epithelial-to-mesenchymal transition (EMT; Hlubek et al., 2007 *Front. Biosci.* 12:458). FZD10$^+$ cells are exposed to Wnt ligands WNT7a and/or WNT7b in the absence or presence of the anti-FZD10 antibodies described herein and translocation of beta-catenin to the cell nuclei is characterized by any of a number of known methodologies (e.g., transcription factor Tcf activation according to Uematsu et al., 2003 *Canc. Res.* 63:4547; or activation of c-myc, cyclin D or survivin transcription, see, e.g., Curtin et al. 2010 *Oncotarget* 1:563).

Example 7

Anti-FZD10 Antibody-Mediated Effects on Progenitor Cell Growth and Differentiation This example describes the use of the herein described anti-FZD10 antibodies to alter (e.g., increase or decrease in a statistically significant manner) cell growth and/or differentiation events in embryonic stem cells and other tissue progenitor cells, including in art-accepted in vitro and in vivo models. These and related methods will find uses in contexts where it is desirable to control human tissue growth and differentiation, including methodologies for tissue regeneration and repair, and for tissue or organ transplantation.

As a brief background, FZD10 is expressed in multiple developing tissues in embryonic stages of a variety of vertebrates including humans, but expression of FZD10 becomes highly restricted in normal tissues in the postnatal organism. In the embryonic mouse, for example, Fzd10 is expressed in limb buds, the Mullerian duct, and the neural tube (Nunnally et al., 2004 *Dev. Genes Evol.* 214:144; Kemp et al., 2007 *Dev. Dynam.* 236:2011). At embryonic day 7, Fzd10 is expressed in the primitive streak of the gastrula but not in migrating mesoderm, suggesting a role in mesoderm induction (Kemp et al., 2007). As the mouse matures, expression becomes limited to very specific neural structures until, by postnatal day 20 through adulthood, Fzd10 is found only in the internal capsule (Yan et al., 2009 *Gene Expression Patterns* 9:173). In the uterus, Fzd10 appears to be involved in endometrial development (Hayashi et al., 2011 *Biol. Reprod.* 84:308).

A developmental role for FZD10 is also observed in non-mammalian vertebrates, lending significance to the evolutionary conservation of this receptor. Fzd10 is expressed in embryonic chicken limb bud mesenchyme (Kawakami et al., 2000 *Develop. Growth Differ.* 42:561). In addition, Fzd10 is expressed along with several other Fzds in various craniofacial structures of the developing bird (Geetha-Loganathan et al., 2009 *Dev. Dynam.* 238:1150). In *Xenopus* development, Fzd10 is expressed in the developing frog in regions of the dorsal neural ectoderm where primary sensory neurons develop. Overexpression of Fzd10 resulted in an increase in the number of sensory neurons in this area, while Fzd10 knockdown inhibited their development (Garcia-Morales et al., 2009 *Dev. Biol.* 335:143), demonstrating the importance of Fzd10 in neural development. In zebrafish, Nasevicius et al. (2000 *Mechs. Develop.* 92:311) used RT-PCR to demonstrate that Fzd10 is expressed during early development in the posterior tail, dorsal neural tube, and brain, while expression is confined to the brain in late embryogenesis.

To assess alteration (e.g., statistically significant increases or decreases) of cell growth and/or differentiation by anti-FZD10 antibodies as described herein, differentiation of human embryonic stem cells is selectively effected in the presence or absence of the herein described anti-FZD10 antibodies, along endothelial cell (e.g., Li et al., 2009 *PLoS One* 4(12):e8443), smooth muscle cell (e.g., Xie et al., 2011 *Arterioscelr. Thromb. Vasc. Biol.* 31(7):1485; Ramkisoensing et al., 2011 *PLoS One* 6(9):e24164) or cardiomyocytic (e.g., Cao et al., 2008 *PLoS One* 3(10):e3474) lineages using the described differentiation-inducing methodologies. In the context of endothelial lineage cellular differentiation, alteration by the herein described anti-FZD10 antibodies of induction of endothelial cell tube formation by induced FZD10$^+$ human embryonic stem cells or their progeny is effected, according to the methodologies described in Hu et al. (2009 *Canc. Res.* 69:6951). In separate studies, FZD10$^+$ human embryonic stem cells or their progeny are introduced and induced to develop into cardiomyocytes to effect in vivo repair of infarction-damaged myocardium, according to methodologies modeled by Hu et al. (2009 *Chin. Med. J. (Engl)* 122:548; 2009 *Clin. Exp. Pharmacol. Physiol.* (December 2009 Epub) PMID 20039910).

In preliminary studies, expression of FZD10 by the cells undergoing induced differentiation is monitored using the herein described anti-FZD10 antibodies to monitor cell surface expression by immunofluorescent methodologies including immunofluorescence microscopy and flow immunocytofluorimetry. FZD10 expression over developmental time is also optionally monitored by quantitative RT-PCR, Western immunoblotting, and/or specific antibody staining of cells with the herein described anti-FZD10 antibody (e.g., the herein described B9L9.3 antibody).

Cell growth and differentiation studies are then conducted by modifying the described procedures (Li et al., 2009; Xie et al., 2011; Ramkisoensing et al., 2011; Cao et al., 2008) to include contacting the cells with subsaturating or saturating concentrations of anti-FZD10 antibodies (e.g., the herein described B9L9.3 antibody) prior to and/or during periods of FZD10 expression. The effects of the anti-FZD10 antibodies on cell growth and differentiation parameters (e.g., growth rate, rate of differentiation, and viability) are observed in vivo and in vitro, and compared to observations made in control groups that are treated with isotype-matched antibodies of irrelevant binding specificity.

For example, human H9 embryonic stem cells (WiCell Research institute, Madison, Wis.) are grown as described by Li et al. (2009) on Matrigel-coated surfaces in mTeSRI medium (Stem Cell Technologies, Vancouver, BC, Canada) and differentiation is induced by transferring cells to ultra-low attachment culture plates (Corning, Inc., Corning, N.Y.) in medium supplemented with basic FGF (bFGF, 20 ng/mL, R&D Systems, Inc., Minneapolis, Minn.) and VEGF (50 ng/mL, R&D Systems), to form suspended embryoid bodies. At day 12 after induction of differentiation, cells are suspended in medium containing 1.5 mg/mL type I rat tail collagen and incubated for 30 minutes at 37° C. to permit collagen gel polymerization, to obtain three-dimensional extracellular matrix cultures. The cultures are supplemented with medium containing bFGF (20 ng/mL) and VEGF (50 ng/mL), in which embryoid body sprouting takes place, and maintained in culture in the absence or presence of anti-FZD10 antibodies over the ensuing three-days. At various time points, samples of the matrix cultures are taken for characterization of the (endothelial) cell surface marker expression phenotype of the cells by flow immunocytofluorimetry, Dil-ac-LDL uptake, and RNA analysis as described (Li et al., 2009). Matrix culture cell samples are also implanted in vivo into the skin of immunocompromised (SCID) test mice, or by direct intramyocardial injection, as described (Li et al., 2009), followed by in vivo imaging and conductance measurements, and histological work-ups of explants, as described (Li et al., 2009). The effects of anti-FZD10 antibodies, including effects on the growth rate, rate of differentiation, and viability, of embryonic stem cell cultures and on the transplanted cells, are noted.

In a similar manner, embryonic stem cells exposed in vitro or in vivo to the herein described anti-FZD10 antibodies (e.g., the herein described B9L9.3 antibody) or to control, isotype-matched antibodies of irrelevant binding specificity are induced to differentiate along smooth muscle cell (e.g., Xie et al., 2011 *Arterioscelr. Thromb. Vasc. Biol.* 31(7):1485; Ramkisoensing et al., 2011 *PLoS One* 6(9):e24164) or cardiomyocytic (e.g., Cao et al., 2008 *PLoS One* 3(10):e3474) lineages and the effects of the antibodies on cell growth rate, rate of differentiation, and viability, such as smooth muscle cell or cardiomyocyte growth and differentiation markers, are determined according to established methodologies described therein (e.g., Xie et al., 2011 *Arterioscelr. Thromb. Vasc. Biol.* 31(7):1485; Ramkisoensing et al., 2011 *PLoS One* 6(9):e24164; Cao et al., 2008 *PLoS One* 3(10):e3474). For instance, measurements of electrophysiological properties, cytosolic calcium cation concentrations, and transplant characteristics as described by Cao et al. (2008) are compared for cells that are contacted with the anti-FZD10 antibody (e.g., B9L9.3) and for cells contacted with an isotype-matched control antibody of irrelevant specificity.

The various embodiments described above can be combined to provide further embodiments. All of the U.S. patents, U.S. patent application publications, U.S. patent application, foreign patents, foreign patent application and non-patent publications referred to in this specification and/or listed in

What is claimed is:

1. A composition comprising an isolated anti-FZD10 antibody that is selected from the group consisting of:

(a) an isolated antibody, or an antigen-binding fragment thereof, that binds to human FZD10, comprising a heavy chain variable region comprising the VHCDR1, VHCDR2 and VHCDR3 amino acid sequences set forth in SEQ ID NOs:5, 6 and 7, respectively, and a light chain variable region comprising the VLCDR1, VLCDR2 and VLCDR3 amino acid sequences set forth in: SEQ ID NOs:9, 11, 12, respectively, or SEQ ID NOs:10, 11, 12, respectively;

(b) the isolated antibody, or an antigen-binding fragment thereof, of (a), wherein the heavy chain variable region comprises the VHCDR1, VHCDR2 and VHCDR3 amino acid sequences set forth in SEQ ID NOs:5, 6, and 7, respectively, and the light chain variable region comprises the VLCDR1, VLCDR2 and VLCDR3 amino acid sequences set forth in SEQ ID NOs:9, 11, and 12, respectively;

(c) the isolated antibody, or an antigen-binding fragment thereof, of (b), wherein he light chain variable region comprises the amino acid sequence set forth in SEQ ID NO:3;

(d) the isolated antibody, or an antigen-binding fragment thereof, of (b), wherein the heavy chain variable region comprises the amino acid sequence set forth in SEQ ID NO:1;

(e) the isolated antibody, or an antigen-binding fragment thereof, of (a), wherein the heavy chain variable region comprises the VHCDR1, VHCDR2 and VHCDR3 amino acid sequences set forth in SEQ ID) NOs:5, 6, and 7, respectively, and the light chain variable region comprises the VLCDR1, VLCDR2 and VLCDR3 amino acid sequences set forth in SEQ ID NOs:10, 11, and 12, respectively;

(f) the isolated antibody, or an antigen-binding fragment thereof, of (e), wherein the heavy chain variable region comprises the amino acid sequence set forth in SEQ ID NO:1;

(g) the isolated antibody, or an antigen-binding fragment thereof, of (e), wherein the light chain variable region comprises the amino acid sequence set forth in SEQ ID NO:4;

(h) the isolated antibody, or an antigen-binding fragment thereof, of (a) wherein the antibody is humanized;

(i) the isolated antibody, or antigen-binding fragment thereof, of (h) wherein the light chain variable region comprises the amino acid sequence set forth in SEQ ID NO:37;

(j) the isolated antibody, or antigen-binding fragment thereof, of (i), further comprising a heavy chain variable region that comprises an amino acid sequence having at least 95% identity to the amino acid sequence of SEQ NO:39;

(k) the isolated antibody, or antigen-binding fragment thereof, of (i), further comprising a heavy chain variable region that comprises the amino acid sequence set forth in SEQ ID NO:39;

(l) the isolated antibody, or antigen-binding fragment thereof, of (k), further comprising a human lambda light chain constant region comprising the amino acid sequence set forth in SEQ ID NO:36;

(m) the isolated antibody, or antigen-binding fragment thereof, of (l), further comprising a human IgG1 constant region comprising the amino acid sequence set forth in SEQ ID NO:34; and (n) the isolated antibody, or antigen-binding fragment thereof, of (h), wherein the isolated antibody comprises a light chain comprising the amino acid sequence set forth in SEQ ID NO:29 and a heavy chain comprising the amino acid sequence set forth in SEQ ID NO:31, 2. The composition of claim 1 wherein the isolated anti-FZD10 antibody is selected from the group consisting of (i) a single chain antibody, a ScFv, a univalent antibody lacking a hinge region, or a minibody; (ii) a Fab, Fab' or F(ab')$_2$ fragment; (iii) a whole antibody; (iv) an antibody that comprises a human IgG Fc domain; and (v) the antibody of (iv) wherein the human IgG Fc domain is modified to obtain a modified antibody that has enhanced ADCC activity as compared to the antibody in which the human IgG Fc domain has not been modified.

3. The composition of claim 1 wherein the isolated anti-FZD10 antibody is conjugated to a drug or a toxin.

4. The composition of claim 3 wherein the toxin is saporin.

5. The composition of claim 1 in which the isolated anti-FZD10 antibody, or an antigen-binding fragment thereof, that binds to human FZD10, comprises a heavy chain variable region comprising the amino acid sequence set forth in SEQ ID NO:1.

6. The composition of claim 5 in which the anti-FZD10 antibody further comprises (i) a light chain variable region comprising an amino acid sequence having at least 95% identity to the amino acid sequence set forth in SEQ ID NO:3; (ii) a light chain variable region comprising the amino acid sequence set forth in SEQ ID NO:3; (iii) a light chain variable region comprising an amino acid sequence having at least 95% identity to the amino acid sequence set forth in SEQ ID NO:4; or (iv) a light chain variable region comprising the amino acid sequence set forth in SEQ ID NO:4.

7. The composition of claim 5 wherein the anti-FZD10 antibody further comprises (i) a light chain variable region comprising an amino acid sequence having at least 95% identity to the amino acid sequence set forth in SEQ ID NO:2; or (ii) a light chain variable region that comprises the amino acid sequence set forth in SEQ ID NO:2.

8. The composition of claim 5 wherein the isolated anti-FZD10 antibody is selected from the group consisting of: (i) a single chain antibody, a ScFv, a univalent antibody lacking a hinge region or a minibody; (ii) a Fab, Fab' or F(ab')$_2$ fragment; (iii) a whole antibody; (iv) an antibody that comprises a human IgG Fc domain; and (v) the antibody of (iv) wherein the human IgG Fc domain is modified to obtain a modified antibody that has enhanced ADCC activity as compared to the antibody in which the human IgG Fc domain has not been modified.

9. An isolated anti-FZD10 antibody, or an antigen-binding fragment thereof, that binds to human FZD-10, comprising
    (a) a light chain variable region comprising the VLCDR1, VLCDR2 and VLCDR3 amino acid sequences set forth in SEQ ID NO:s 9, 11, 12, respectively, or SEQ. ID) NOs:10, 11, 12 respectively; and
    (b) a heavy chain variable region comprises the VHCDR1, VHCDR2 and VHCDR3 amino acid sequences set forth in SEQ ID NO:s 5, 6 and 7, respectively.

10. The anti-FZD10 antibody of claim 9, wherein said antibody is selected from the group consisting of: (i) a single chain antibody, a ScFv, a univalent antibody lacking a hinge region or a minibody, (ii) a Fab, Fab' or F(ab'), fragment; (iii) a whole antibody; (iv) an antibody that comprises a human IgG Fc domain; and (v) the antibody of (iv) wherein the human IgG Fc domain is modified to obtain a modified antibody that has enhanced ADCC activity as compared to the antibody in which the human IgG Fc domain has not been modified.

11. The antibody of claim 9 wherein the isolated anti-FZD10 antibody is conjugated to a drug or a toxin.

12. The antibody of claim 11 wherein the toxin is saporin.

13. The composition of claim 1 which further comprises a physiologically acceptable carrier.

14. The composition of claim 1, wherein the isolated anti-FZD10 antibody, or antigen-binding fragment thereof, is conjugated to a detectable moiety.

15. The isolated anti-FZD10 antibody, or antigen-binding fragment thereof, of claim 9, wherein the antibody or antibody-binding fragment is conjugated to a detectable moiety.

16. The isolated antibody or antigen-binding fragment thereof of claim 9, wherein the antibody or antigen-binding fragment thereof is humanized.

17. The isolated antibody or antigen-binding fragment thereof of claim 16, wherein the antibody or antigen-binding fragment thereof comprises a light chain variable region comprising the amino acid sequence set forth in SEQ ID NO:37.

18. The isolated antibody or antigen-binding fragment thereof of claim 16, wherein the antibody or antigen-binding fragment thereof comprises a heavy chain variable region comprising the amino acid sequence set forth in SEQ ID NO:39.

19. The isolated antibody of claim 16, wherein the antibody comprises a light chain comprising the amino acid sequence set forth in SEQ ID NO:29 and a heavy chain comprising the amino acid sequence set forth in SEQ ID NO:31.

* * * * *